(12) United States Patent
Augereau et al.

(10) Patent No.: US 7,423,030 B2
(45) Date of Patent: Sep. 9, 2008

(54) 1-AMINO-PHTHALAZINE DERIVATIVES, THE PREPARATION AND THE THERAPEUTIC USE THEREOF

(75) Inventors: Jean Michel Augereau, Toulouse (FR); Michel Geslin, Villeneuve Tolosane (FR); Gilles Courtemanche, Saubens (FR)

(73) Assignee: Sanofi-Aventis, Paris (FR)

( * ) Notice: Subject to any disclaimer, the term of this patent is extended or adjusted under 35 U.S.C. 154(b) by 0 days.

(21) Appl. No.: 11/548,545

(22) Filed: Oct. 11, 2006

(65) Prior Publication Data

US 2007/0099895 A1    May 3, 2007

Related U.S. Application Data

(63) Continuation of application No. PCT/FR2005/000889, filed on Apr. 13, 2005.

(30) Foreign Application Priority Data

Apr. 13, 2004    (FR)    .................................. 04 03806

(51) Int. Cl.
| | |
|---|---|
| A61K 31/335 | (2006.01) |
| A61K 31/397 | (2006.01) |
| A61K 31/4025 | (2006.01) |
| A61K 31/4427 | (2006.01) |
| A61K 31/496 | (2006.01) |
| C07D 401/12 | (2006.01) |
| C07D 413/12 | (2006.01) |
| C07D 417/12 | (2006.01) |
| C07D 419/12 | (2006.01) |
| C07D 237/34 | (2006.01) |
| C07C 65/21 | (2006.01) |
| C07D 221/22 | (2006.01) |
| C07D 211/74 | (2006.01) |
| C07D 211/86 | (2006.01) |
| C07D 213/55 | (2006.01) |
| C07D 333/22 | (2006.01) |

(52) U.S. Cl. ............................ 514/210.21; 514/217.05; 514/248; 540/481; 540/599; 544/237; 562/460; 562/473; 546/112; 546/342; 549/70; 564/443

(58) Field of Classification Search ............ 514/210.21, 514/217.05, 248; 540/481, 599; 544/237
See application file for complete search history.

(56) References Cited

U.S. PATENT DOCUMENTS

| 2,484,029 A | 10/1949 | Hartmann et al. |
| 6,258,812 B1 | 7/2001 | Bold et al. |
| 6,589,951 B1 | 7/2003 | Napoletano et al. |

FOREIGN PATENT DOCUMENTS

| DE | 1005072 | 3/1957 |
| WO | WO 03/106452 | 12/2003 |

OTHER PUBLICATIONS

Gomori, et al., Brit. J. Pharmacol., 2007, 151, 900-908.*
Mashiko, et al., Endocrinology, 2005, 146 (7), 3080-3086.*
Shimazaki, et al., CNS Drugs, vol. 20, No. 10, 2006, pp. 801-881.*
DeNino, et al., Curr. Opin. Endocrinol. Diabetes 10:330-333, 2003.*
Amstutz, E.D., et al., The Synthesis of Benzene Derivatives Structural Similar to Penicillic Acid, Journal of the American Chemical Society vol. 68, No. 3 (1968).
Badr, M.Z.A., et al., Substitution and Ring Closure Reactions of Phthalazine Derivatives, Journal of Heterocyclic Chemistry, vol. 21, (1984) pp. 471-475.
Hill, J.M., et al., Nucleophilic Heteroaromatic Substitution II. Phthalazines, J. Org. Chem., vol. 36, No. 21, (1971).
Mustafa, A., et al., Reactions with 1(2H)-Phthalazinones, 4,5-Dihydro-3(2H)-Pyridazinones and 3-Pyrazolin-5-Ones, Tetrahedron, (1964) vol. 20, pp. 531-544.
Newman, M.S., et. al., o-Carbonyl-Assisted Hydrolyses of Methyl Benzoates. Journal of the American Chemical Society vol. 90, No. 16, (1968).
Tyman, J.H.P., et al., The Structure of 2-Keto and 2-Aldehydobenzoic Acids (Spectroscopic Studies), Spectrochimica Acta vol. 33A, pp. 479-485 (1977).
Ullyot, G.E., et al., Analgesics. II. A New Synthesis of Aminophthalidylalkanes, Journal of the American Society vol. 70, No. 2, 1948 pp. 542-545.
Vaughan, W.R., et al., The Preparation of Some Phthalazines and Related Substances, Journal of American Chemical Society, vol. 68, No. 7, (1946) pp. 1314-1316.
Wheeler, D.D., et al., Reactions of Phthalaldehydic Acid, Journal of Organic Chemistry, vol. 22, No. 5, (1957) pp. 547-556.
1-Phthalazinamine, 4-Phenyl-N-[1-(Phenylmethyl)-4-Piperidinyl]-, Ambinter Screening Library (2004) XP002296138 Database Accession No. 2003:902721 abstract compound CAS registry No. 379238-00-3.

(Continued)

*Primary Examiner*—Mark L. Berch
*Assistant Examiner*—Cecilia M Jaisle
(74) *Attorney, Agent, or Firm*—Balaram Gupta

(57) ABSTRACT

A 1-amino-phthalazine derivative of general formula (I)

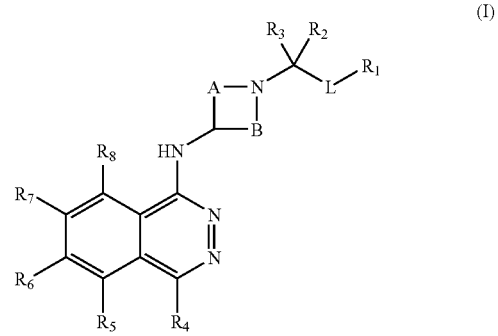

wherein the substituents are as defined herein. Also disclosed are a method for preparing such compounds, intermediates for use in such method and medical treatments using the compounds of formula (I).

6 Claims, No Drawings

OTHER PUBLICATIONS

1-Phthalazinamine, 4-Phenyl-N-[1-(Phenylmethyl)-4-Piperidinyl]-, Interchim Intermediates (2002) XP002296137 Database accession No. 2002:2783954 abstract compound CAS registry No. 379238-00-3.

1-Phthalazinamine, 4-Phenyl-N-[1-(Phenylmethyl)-4-Piperidinyl]-, Otava Stock Chemicals (2003) XP002296136 Database accession No. 2002:775677 abstract compound CAS registry No. 379238-00-3.

* cited by examiner

1-AMINO-PHTHALAZINE DERIVATIVES, THE PREPARATION AND THE THERAPEUTIC USE THEREOF

CROSS-REFERENCE TO RELATED APPLICATIONS

This application is a continuation of PCT/FR2005/000889, filed Apr. 13, 2005, which claims priority from French Patent Application No. 04/03,806, filed Apr. 13, 2004.

SUMMARY OF THE INVENTION

The present invention relates to 1-aminophthalazine derivatives, to their preparation and to their therapeutic application.

BACKGROUND OF THE INVENTION

The search for antagonists of the MCH (Melatonin-Concentrating Hormone) receptor 1, the $MCH_1$ receptor, has aroused the interest of many pharmaceutical companies. A certain number of patent applications have been filed, among which mention may be made of WO 01/21577 (Takeda), WO 02/06245 (Synaptic) and WO 03/106452 (Millennium). A certain number of publications have appeared, among which is Ma V. V. et al. (Amgen) 224th Nat. Meeting ACS Boston. Poster MEDI 343 (21 Aug. 2002).

In the last ten years, it has been demonstrated that many neuropeptides are involved in the central regulations governing eating behaviour and also the energy balance (Inui et al., TINS 1999; 22(2): 62-67). MCH is among these neuropeptides.

Two MCH receptors have recently been cloned: the $MCH_1$ receptor, previously known as the SLC-1 or GPR24 receptor (Chambers et al., Nature 1999; 400: 261-265), and the $MCH_2$ receptor, previously known as SLT (Mori et al., Biochem Biophys Res Commun 2001; 283: 1013-1018).

There is thus real interest in finding novel compounds for modulating the activity of the $MCH_1$ receptor.

SUMMARY OF THE INVENTION

It has now been found that 1-aminophthalazine-based compounds show high affinity and selectivity towards the $MCH_1$ receptor.

DETAILED DESCRIPTION OF THE INVENTION

One subject of the present invention is compounds corresponding to formula (I)

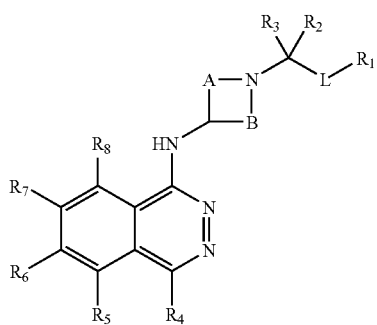

(I)

A represents a $C_{1-4}$-alkylene group optionally substituted with one or more groups $R_9$, which may be identical or different;
B represents a $C_{1-4}$-alkylene group optionally substituted with one or more groups $R_{10}$, which may be identical or different;
$R_9$ and $R_{10}$ each represent, independently of each other, a hydrogen atom or a $C_{1-5}$-alkyl group,
or alternatively $R_9$ and $R_{10}$ together form a single bond or a $C_{1-4}$-alkylene group;
L represents a single bond or a $C_{1-2}$-alkylene, —CH=CH— or —C≡C— group; the $C_{1-2}$-alkylene and —CH=CH— groups being optionally substituted with one or more $C_{1-2}$-alkyl substituents; or alternatively L represents a cycloprop-1,2-diyl group;
$R_1$ represents an aryl or a heteroaryl; the aryl and heteroaryl groups being optionally substituted with one or more radicals Z, which may be identical or different;
$R_2$ and $R_3$ represent, independently of each other, a hydrogen atom or a $C_{1-3}$-alkyl or $C_{1-3}$-fluoroalkyl group,
or alternatively $R_2$ or $R_3$ form, together with the carbon atom that bears them, a cycloprop-1,1-diyl group;
$R_4$ represents a hydrogen atom or a $C_{1-5}$-alkyl, $C_{1-3}$-fluoroalkyl, $C_{3-6}$-cycloalkyl, $C_{3-6}$-cycloalkyl-$C_{1-3}$-alkylene, $C_{1-3}$-alkyl-O—$C_{1-3}$-alkylene, HO—$C_{1-3}$-alkylene or $C_{1-3}$-alkyl-X-$C_{1-3}$-alkylene group in which X represents S, SO or $SO_2$,
or alternatively $R_4$ represents an $R_aR_bN$—$C_{1-3}$-alkylene, aryl, aryl-$C_{1-3}$-alkylene, aryl-O—, aryl-O—$C_{1-3}$-alkylene, aryl-$C_{1-3}$-alkylene-O—$C_{1-3}$-alkylene, heteroaryl or heteroaryl-$C_{1-3}$-alkylene group; the aryl, aryl-$C_{1-3}$-alkylene, aryl-O—, aryl-O—$C_{1-3}$-alkylene, heteroaryl and heteroaryl-$C_{1-3}$-alkylene groups being optionally substituted with one or more radicals Z, which may be identical or different;
$R_5$ represents a hydrogen or halogen atom or a $C_{1-5}$-alkyl, $C_{1-3}$-fluoroalkyl, $C_{1-5}$-alkoxy, $C_{1-3}$-fluoroalkoxy, HO—$C_{1-3}$-alkylene, —CN or $C_{1-3}$-alkyl-X— group in which X represents S, SO or $SO_2$,
or alternatively $R_5$ represents an $R_aR_bN$—, $R_aR_bN$—$C_{1-3}$-alkylene, aryl, aryl-$C_{1-3}$-alkylene, aryl-O— or heteroaryl group; the aryl, aryl-$C_{1-3}$-alkylene, aryl-O— and heteroaryl groups being optionally substituted with one or more radicals Z, which may be identical or different;
$R_6$ represents a hydrogen or halogen atom or a $C_{1-5}$-alkyl, $C_{1-3}$-fluoroalkyl, $C_{1-5}$-alkoxy, $C_{1-3}$-fluoroalkoxy, —CN, $R_aR_bN$—, $R_aR_bN$—$C_{1-3}$-alkylene, aryl or heteroaryl group; the aryl and heteroaryl groups being optionally substituted with one or more radicals Z, which may be identical or different;
$R_7$ represents a hydrogen or halogen atom or a $C_{1-5}$-alkyl, $C_{1-3}$-fluoroalkyl, $C_{1-5}$-alkoxy, $C_{1-3}$-fluoroalkoxy, HO—$C_{1-3}$-alkylene, —CN or $C_{1-3}$-alkyl-X— group in which X represents S, SO or $SO_2$,
or alternatively $R_7$ represents an $R_aR_bN$—, $R_aR_bN$—$C_{1-3}$-alkylene, $R_aR_bNC(O)$—, $C_{1-3}$-alkyl-C(O)—, aryl, aryl-O— or heteroaryl group; the aryl, aryl-O— and heteroaryl groups being optionally substituted with one or more radicals Z, which may be identical or different;
$R_8$ represents a hydrogen or halogen atom or a $C_{1-5}$-alkyl, $C_{1-5}$-alkoxy or $C_{1-3}$-fluoroalkoxy group;
Z represents a hydrogen or halogen atom or a $C_{1-5}$-alkyl, $C_{1-3}$-fluoroalkyl, $C_{3-6}$-cycloalkyl, $C_{3-6}$-cycloalkyl-$C_{1-3}$-alkylene, phenyl, $C_{1-5}$-alkoxy, $C_{1-3}$-fluoroalkoxy, $C_{1-3}$-alkyl-O—$C_{1-3}$-alkylene, HO—$C_{1-3}$-alkylene, $NO_2$, —CN, $C_{1-3}$-alkyl-X— or $C_{1-3}$-alkyl-X-$C_{1-3}$-alkylene group in which X represents S, SO or $SO_2$, or alternatively Z represents an $R_aR_bN$—, $R_aR_bN$—$C_{1-3}$-alkylene, $R_aR_bNC(O)$—, $C_{1-3}$-alkyl-C(O)—, $C_{1-4}$-alkyl-$CO_2$— or $C_{3-6}$-cycloalkyl-C(O)— group, or alternatively Z represents an oxo radical, or alternatively two adjacent radicals Z together form a $C_{1-3}$-alkylenedioxy group;

$R_a$ and $R_b$ each represent, independently of each other, a hydrogen atom or a $C_{1-3}$-alkyl or $C_{1-3}$-alkyl-C(O)— group, or alternatively $R_a$ and $R_b$ form, together with the nitrogen atom that bears them, a heterocycle optionally substituted with one or more $C_{1-3}$-alkyl or oxo groups;

it being understood that when $R_2$, $R_3$, $R_5$, $R_6$, $R_7$ and $R_8$ all represent a hydrogen atom, A and B both represent an ethylenyl group (—$CH_2CH_2$—) and L is a single bond, $R_1$ and $R_4$ cannot both represent an unsubstituted phenyl group.

The compounds of formula (I) may comprise one or more asymmetric carbon atoms. They may thus exist in enantiomeric or diastereoisomeric form. These enantiomers and diastereoisomers, and also mixtures thereof, including racemic mixtures, form part of the invention.

The compounds of formula (I) may comprise one or more rings. They may thus exist in the form of axial/equatorial, or endo/exo, or cis/trans isomers. These isomers, and also mixtures thereof, form part of the invention.

The compounds of formula (I) may comprise one or more olefinic functions. They may thus exist in the form of Z/E isomers. These isomers, and also mixtures thereof, form part of the invention.

The compounds of formula (I) may exist in the form of bases or of acid-addition salts. Such addition salts form part of the invention.

These salts are advantageously prepared with pharmaceutically acceptable acids, but the salts of other acids that are useful, for example, for purifying or isolating the compounds of formula (I) also form part of the invention.

The compounds of formula (I) may also exist in the form of hydrates and/or solvates, i.e. in the form of associations or combinations with one or more water molecules and/or solvent. Such hydrates and solvates also form part of the invention.

In the context of the present invention, the following definitions apply:

$C_{t-z}$ in which t and z may take values from 1 to 6, a chain or a carbon-based ring possibly containing from t to z carbon atoms, for example $C_{1-3}$ can characterize a carbon-based chain containing from 1 to 3 carbon atoms;

a halogen atom: a fluorine, a chlorine, a bromine or an iodine;

an alkyl group: a linear or branched, saturated monovalent aliphatic group. Examples that may be mentioned include methyl, ethyl, propyl, isopropyl, butyl, isobutyl, tert-butyl, pentyl, etc. groups;

an alkylene group: a linear or branched saturated divalent aliphatic group. By way of example, a $C_{1-3}$-alkylene group represents a linear or branched divalent carbon-based chain of 1 to 3 carbon atoms, such as a methylenyl (—$CH_2$—), an ethylenyl (—$CH_2CH_2$—), a 1-methyl-ethylenyl (—$CH(CH_3)CH_2$—), a propylenyl (—$CH_2CH_2CH_2$—), etc.;

a cycloalkyl group: a saturated cyclic aliphatic group. Examples that may be mentioned include cyclopropyl, methylcyclopropyl, cyclobutyl, cyclopentyl, cyclohexyl, etc. groups;

an alkoxy group: an alkyl-O— radical in which the alkyl group is as defined above;

an alkylenedioxy group: an —O-alkylene-O— group, in which the alkylene group is as defined above. Examples that may be mentioned include methylenedioxy, ethylenedioxy and propylenedioxy groups;

a fluoroalkyl group: an alkyl group of which one or more hydrogen atoms have been replaced with a fluorine atom. Examples that may be mentioned include $CF_3$—, $CF_3CH_2$—, etc. groups;

a fluoroalkoxy group: an alkoxy group of which one or more hydrogen atoms have been replaced with a fluorine atom. Examples that may be mentioned include $CF_3O$—, $CHF_2O$—, etc. groups;

a heterocyclic group: a saturated 5- to 7-membered cyclic group comprising one or more hetero atoms such as nitrogen, oxygen or sulfur atoms. Examples that may be mentioned include pyrrolidinyl, piperidyl, piperidonyl, morpholinyl, piperazinyl, N-methyl-piperazinyl, etc. groups;

an aryl group: monocyclic or polycyclic aromatic system containing from 6 to 14 carbon atoms and preferably from 6 to 10 carbon atoms. When the system is polycyclic, at least one of the rings is aromatic. Examples that may be mentioned include phenyl, naphthyl, tetrahydronaphthyl, indanyl, etc. groups;

a heteroaryl group: 5- to 14-membered and preferably 5- to 10-membered monocyclic or polycyclic aromatic system comprising one or more hetero atoms such as nitrogen, oxygen or sulfur atoms. When the system is polycyclic, at least one of the rings is aromatic. The nitrogen atoms may be in the form of N-oxides. Examples of monocyclic heteroaryl groups that may be mentioned include thiazolyl, thiadiazolyl, thienyl, imidazolyl, triazolyl, tetrazolyl, pyridyl, furanyl, oxazolyl, isoxazolyl, oxadiazolyl, pyrrolyl, pyrazolyl, pyrimidinyl and pyridazinyl groups. Examples of bicyclic heteroaryl groups that may be mentioned include indolyl, benzofuranyl, chromen-2-on-yl, benzimidazolyl, benzothienyl, benzotriazolyl, benzothiazolyl, benzoxazolyl, quinolinyl, isoquinolinyl, indazolyl, indolizinyl, quinazolinyl, phthalazinyl, quinoxalinyl, naphthyridinyl, 2,3-dihydro-1H-indolyl, 2,3-dihydrobenzofuranyl, tetrahydroquinolinyl and tetrahydroisoquinolinyl groups.

In the general formula (I), the ring:

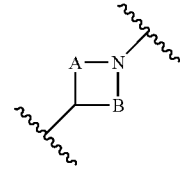

may be, for example, an azetidinyl, pyrrolidinyl, piperidyl, azepanyl, 8-azabicyclo[3.2.1]octyl, 8-azabicyclo[3.3.1]nonanyl, decahydroisoquinolinyl or 3-azabicyclo[3.1.0]hexanyl group.

Among the compounds of formula (I) that are subjects of the invention, mention may be made of a first subgroup of compounds that are defined as follows:

A represents a $C_{1-4}$-alkylene group optionally substituted with one or more groups $R_9$, which may be identical or different;

B represents a $C_{1-4}$-alkylene group optionally substituted with one or more groups $R_{10}$, which may be identical or different;

$R_9$ and $R_{10}$ each represent a hydrogen atom, or alternatively $R_9$ and $R_{10}$ together form a $C_{1-4}$-alkylene group;

L represents a single bond or —CH═CH—;

$R_1$ represents an aryl or a heteroaryl; the aryl and heteroaryl groups being optionally substituted with one or more radicals Z, which may be identical or different;

$R_2$ and $R_3$ represent, independently of each other, a hydrogen atom or a $C_{1-3}$-alkyl group;

$R_4$ represents a hydrogen atom or a $C_{1-5}$-alkyl, $C_{3-6}$-cycloalkyl, $C_{3-6}$-cycloalkyl-$C_{1-3}$-alkylene, $C_{1-3}$-alkyl-O—$C_{1-3}$-alkylene, aryl, aryl-$C_{1-3}$-alkylene, aryl-$C_{1-3}$-alkylene-O—$C_{1-3}$-alkylene, heteroaryl or heteroaryl-$C_{1-3}$-alkylene group; the aryl, aryl-$C_{1-3}$-alkylene, heteroaryl and heteroaryl-$C_{1-3}$-alkylene groups being optionally substituted with one or more radicals Z, which may be identical or different;

$R_5$ represents a hydrogen atom or a $C_{1-5}$-alkyl, $C_{1-5}$-alkoxy or aryl group; the aryl group being optionally substituted with one or more radicals Z, which may be identical or different;

$R_6$ represents a hydrogen atom;

$R_7$ represents a halogen atom or a $C_{1-5}$-alkyl group and more particularly a methyl, $C_{1-5}$-alkoxy and more particularly a methoxy or an aryl;

$R_8$ represents a hydrogen atom;

Z represents a hydrogen or halogen atom or a $C_{1-5}$-alkyl, $C_{1-3}$-fluoroalkyl, $C_{3-6}$-cycloalkyl, $C_{3-6}$-cycloalkyl-$C_{1-3}$-alkylene, phenyl, $C_{1-5}$-alkoxy, $C_{1-3}$-fluoroalkoxy, $C_{1-3}$-alkyl-O—$C_{1-3}$-alkylene, HO—$C_{1-3}$-alkylene, $NO_2$, —CN, $C_{1-3}$-alkyl-X— or $C_{1-3}$-alkyl-X—$C_{1-3}$-alkylene group in which X represents S, SO or $SO_2$, or alternatively Z represents an $R_aR_bN$—, $R_aR_bN$—$C_{1-3}$-alkylene, $R_aR_bNC(O)$—, $C_{1-3}$-alkyl-C(O)— or $C_{3-6}$-cycloalkyl-C(O)— group, or alternatively Z represents an oxo radical, or alternatively two adjacent radicals Z together form a $C_{1-3}$-alkylenedioxy group;

$R_a$ and $R_b$ each represent, independently of each other, a hydrogen atom or a $C_{1-3}$-alkyl or $C_{1-3}$-alkyl-C(O)— group, or alternatively $R_a$ and $R_b$ form, together with the nitrogen atom that bears them, a heterocycle optionally substituted with one or more $C_{1-3}$-alkyl or oxo groups.

Among the compounds of formula (I) that are subjects of the invention, mention may be made of a second subgroup of compounds that are defined as follows:

A represents a $C_{1-4}$-alkylene group optionally substituted with a group $R_9$;

B represents a $C_{1-4}$-alkylene group optionally substituted with a group $R_{10}$;

$R_9$ and $R_{10}$ each represent a hydrogen atom or $R_9$ and $R_{10}$ together form a $C_{1-4}$-alkylene group;

L represents a single bond or —CH═CH—;

$R_1$ represents an aryl optionally substituted with one or more radicals Z, which may be identical or different;

$R_2$ and $R_3$ represent, independently of each other, a hydrogen atom or a $C_{1-3}$-alkyl group;

$R_4$ represents a hydrogen atom or a $C_{1-5}$-alkyl, $C_{3-6}$-cycloalkyl, $C_{3-6}$-cycloalkyl-$C_{1-3}$-alkylene, $C_{1-3}$-alkyl-O—$C_{1-3}$-alkylene or aryl group and more particularly a phenyl, or a heteroaryl group and more particularly a thienyl or a pyridyl; the aryl and heteroaryl groups being optionally substituted with one or more radicals Z, which may be identical or different;

$R_5$ represents a hydrogen atom;

$R_6$ represents a hydrogen atom;

$R_7$ represents a halogen atom, a methyl or a methoxy;

$R_8$ represents a hydrogen atom;

Z represents a hydrogen atom, a halogen atom or a $C_{1-5}$-alkyl, $C_{1-5}$-alkoxy and more particularly methoxy, $C_{1-3}$-alkyl-O—$C_{1-3}$-alkylene, phenyl, HO—$C_{1-3}$-alkylene, —CN or $C_{1-3}$-alkyl-X— group in which X represents a sulfur atom, or alternatively Z represents an $R_aR_bN$—, $R_aR_bN$—$C_{1-3}$-alkylene, $R_aR_bNC(O)$— or $C_{1-3}$-alkyl-C(O)— group, or alternatively Z represents an oxo radical, or alternatively two adjacent radicals Z together form a $C_{1-3}$-alkylenedioxy group, more particularly a methylenedioxy;

$R_a$ and $R_b$ each represent, independently of each other, a hydrogen atom or a $C_{1-3}$-alkyl or $C_{1-3}$-alkyl-C(O)— group.

In the context of the present invention the compounds of formula (I) in which at least one of the substituents $R_5$, $R_6$, $R_7$ or $R_8$ is other than a hydrogen atom are more particularly suitable.

Among the compounds of formula (I) that are subjects of the invention, mention may be made especially of:

7-methoxy-4-(4-methoxyphenyl)-N-[8-(2-naphthylmethyl)-8-azabicyclo[3.2.1]oct-3-yl]phthalazin-1-amine (compound 4);

7-methoxy-4-(4-methoxyphenyl)-N-[1-(2-naphthylmethyl)piperidin-4-yl]phthalazin-1-amine (compound 3);

7-methoxy-4-(3-methoxyphenyl)-N-[1-(2-naphthylmethyl)piperidin-4-yl]phthalazin-1-amine (compound 5);

7-methoxy-4-(2-methoxyphenyl)-N-[1-(2-naphthylmethyl)piperidin-4-yl]phthalazin-1-amine (compound 2);

7-methoxy-N-[1-(2-naphthylmethyl)piperidin-4-yl]-4-phenylphthalazin-1-amine (compound 1);

4-(4-methoxyphenyl)-7-methyl-N-[1-(2-naphthylmethyl)piperidin-4-yl]phthalazin-1-amine (compound 9);

4-(3,4-dimethoxyphenyl)-7-methoxy-N-[1-(2-naphthylmethyl)piperidin-4-yl]phthalazin-1-amine (compound 10);

N-[1-(1,3-benzodioxol-5-ylmethyl)piperidin-4-yl]-7-methoxy-4-(4-methoxyphenyl)phthalazin-1-amine dihydrochloride (compound 19);

4-ethyl-7-methoxy-N-[1-(2-naphthylmethyl)piperidin-4-yl]phthalazin-1-amine (compound 20);

4-benzyl-7-methoxy-N-[1-(2-naphthylmethyl)piperidin-4-yl]phthalazin-1-amine (compound 21);

7-methoxy-4-(methoxymethyl)-N-[1-(2-naphthylmethyl)piperidin-4-yl]phthalazin-1-amine hydrochloride (compound 24);

N-[1-(1-benzofuran-5-ylmethyl)piperidin-4-yl]-7-methoxy-4-(4-methoxyphenyl)phthalazin-1-amine (compound 26);

N-[1-(3,4-dimethylbenzyl)piperidin-4-yl]-7-methoxy-4-(4-methoxyphenyl)phthalazin-1-amine (compound 29);

7-methoxy-4-(4-methoxyphenyl)-N-{1-[(1-methyl-1H-indol-2-yl)methyl]piperidin-4-yl}phthalazin-1-amine (compound 31);

4-cyclopropyl-7-methoxy-N-[1-(2-naphthylmethyl)piperidin-4-yl]phthalazin-1-amine (compound 33);

N-[1-(3-fluoro-4-methoxybenzyl)piperidin-4-yl]-7-methoxy-4-(4-methoxyphenyl)phthalazin-1-amine (compound 39);

N-[1-(2,3-dihydro-1,4-benzodioxin-6-ylmethyl)piperidin-4-yl]-7-methoxy-4-(4-methoxyphenyl)phthalazin-1-amine (compound 40);

4-(1,3-benzodioxol-5-yl)-7-methoxy-N-[1-(2-naphthylmethyl)piperidin-4-yl]phthalazin-1-amine dihydrochloride (compound 42);

4-(4-chlorophenyl)-7-methoxy-N-[1-(2-naphthylmethyl)piperidin-4-yl]phthalazin-1-amine (compound 43);

7-methoxy-N-[1-(2-naphthylmethyl)piperidin-4-yl]-4-[4-(trifluoromethyl)phenyl]phthalazin-1-amine (compound 45);

N-[1-(1-benzothien-2-ylmethyl)piperidin-4-yl]-7-methoxy-4-(4-methoxyphenyl)phthalazin-1-amine (compound 48);

4-cyclopentyl-7-methoxy-N-[1-(2-naphthylmethyl)piperidin-4-yl]phthalazin-1-amine dihydrochloride (compound 51);

N-[1-(2,3-dihydro-1-benzofuran-5-ylmethyl)piperidin-4-yl]-7-methoxy-4-(4-methoxyphenyl)phthalazin-1-amine (compound 54);

N-[1-(2,3-dihydro-1H-inden-5-ylmethyl)piperidin-4-yl]-7-methoxy-4-(4-methoxyphenyl)phthalazin-1-amine (compound 55);

7-methoxy-4-(4-methoxyphenyl)-N-{1-[1-(2-naphthyl)ethyl]piperidin-4-yl}phthalazin-1-amine dihydrochloride (compound 56);

N-[1-(1,3-benzothiazol-6-ylmethyl)piperidin-4-yl]-7-methoxy-4-(4-methoxyphenyl)phthalazin-1-amine (compound 59);

N-[1-(1-benzothien-5-ylmethyl)piperidin-4-yl]-7-methoxy-4-(4-methoxyphenyl)phthalazin-1-amine (compound 60);

N-[1-(1H-indol-3-ylmethyl)piperidin-4-yl]-7-methoxy-4-(4-methoxyphenyl)phthalazin-1-amine (compound 65);

7-methoxy-4-(4-methylphenyl)-N-[1-(2-naphthylmethyl)piperidin-4-yl]phthalazin-1-amine (compound 66);

4-butyl-7-methoxy-N-[1-(2-naphthylmethyl)piperidin-4-yl]phthalazin-1-amine (compound 67);

7-methoxy-4-(4-methoxyphenyl)-N-{1-[(2E)-3-phenylprop-2-en-1-yl]piperidin-4-yl}phthalazin-1-amine dihydrochloride (compound 69);

7-methoxy-N-[1-(2-naphthylmethyl)piperidin-4-yl]-phthalazin-1-amine (compound 70);

4-(cyclopropylmethyl)-7-methoxy-N-[1-(2-naphthylmethyl)piperidin-4-yl]phthalazin-1-amine (compound 71);

N-[1-(3-fluoro-4-methylbenzyl)piperidin-4-yl]-7-methoxy-4-(4-methoxyphenyl)phthalazin-1-amine (compound 74);

7-methoxy-4-(4-methoxyphenyl)-N-[1-(4-methylbenzyl)piperidin-4-yl]phthalazin-1-amine (compound 75);

4-(4-fluorophenyl)-7-methoxy-N-[1-(2-naphthylmethyl)piperidin-4-yl]phthalazin-1-amine (compound 82);

N-[1-(1H-indol-5-ylmethyl)piperidin-4-yl]-7-methoxy-4-(4-methoxyphenyl)phthalazin-1-amine (compound 87);

7-methoxy-4-[4-(methoxymethyl)phenyl]-N-[1-(2-naphthylmethyl)piperidin-4-yl]phthalazin-1-amine (compound 88);

7-methoxy-N-[1-(4-methoxy-3-methylbenzyl)piperidin-4-yl]-4-(4-methoxyphenyl)phthalazin-1-amine (compound 89);

7-methoxy-4-methyl-N-[1-(2-naphthylmethyl)piperidin-4-yl]phthalazin-1-amine (compound 95);

4-(2,5-dimethoxyphenyl)-7-methoxy-N-[1-(2-naphthylmethyl)piperidin-4-yl]phthalazin-1-amine dihydrochloride (compound 97);

7-methoxy-4-(4-methoxyphenyl)-N-[1-(quinolin-6-ylmethyl)piperidin-4-yl]phthalazin-1-amine (compound 99);

7-methoxy-4-(4-methoxyphenyl)-N-{1-[(1-methyl-1H-indol-5-yl)methyl]piperidin-4-yl}phthalazin-1-amine (compound 100);

4-(2,4-dimethoxyphenyl)-7-methoxy-N-[1-(2-naphthylmethyl)piperidin-4-yl]phthalazin-1-amine dihydrochloride (compound 102);

4-(3,5-dimethoxyphenyl)-7-methoxy-N-[1-(2-naphthylmethyl)piperidin-4-yl]phthalazin-1-amine dihydrochloride (compound 103);

7-methoxy-N-[1-(2-naphthylmethyl)piperidin-4-yl]-4-(2-phenylethyl)phthalazin-1-amine dihydrochloride (compound 104);

4-{4-[(diethylamino)methyl]phenyl}-7-methoxy-N-[1-(2-naphthylmethyl)piperidin-4-yl]phthalazin-1-amine trihydrochloride (compound 105);

7-fluoro-4-(4-fluorophenyl)-N-[1-(2-naphthylmethyl)piperidin-4-yl]phthalazin-1-amine (compound 106);

7-methoxy-N-[1-(2-naphthylmethyl)piperidin-4-yl]-4-pyridin-3-ylphthalazin-1-amine trihydrochloride (compound 109);

N-[1-(4-chlorobenzyl)piperidin-4-yl]-7-methoxy-4-(4-methoxyphenyl)phthalazin-1-amine dihydrochloride (compound 110);

{4-[(4-{[7-methoxy-4-(4-methoxyphenyl)phthalazin-1-yl]amino}piperidin-1-yl)methyl]phenyl}methanol dihydrochloride (compound 112);

N-{1-[4-(aminomethyl)benzyl]piperidin-4-yl}-7-methoxy-4-(4-methoxyphenyl)phthalazin-1-amine trihydrochloride (compound 113);

N-{4-[(4-{[7-methoxy-4-(4-methoxyphenyl)phthalazin-1-yl]amino}piperidin-1-yl)methyl]phenyl}acetamide dihydrochloride (compound 114);

1-{4-[(4-([7-methoxy-4-(4-methoxyphenyl)phthalazin-1-yl]aminopiperidin-1-yl)methyl]phenyl}ethanone dihydrochloride (compound 121);

N-[1-(1-benzofuran-5-ylmethyl)piperidin-4-yl]-4-(2,5-dimethoxyphenyl)-7-methoxyphthalazin-1-amine dihydrochloride (compound 124);

N-[1-(1,3-benzodioxol-5-ylmethyl)piperidin-4-yl]-4-(2,5-dimethoxyphenyl)-7-methoxyphthalazin-1-amine dihydrochloride (compound 125);

6-[(4-{[7-methoxy-4-(4-methoxyphenyl)phthalazin-1-yl]amino}piperidin-1-yl)methyl]-2H-chromen-2-one dihydrochloride (compound 127);

N-[1-(1H-indol-6-ylmethyl)piperidin-4-yl]-7-methoxy-4-(4-methoxyphenyl)phthalazin-1-amine (compound 129);

7-methoxy-N-[1-(4-methoxybenzyl)piperidin-4-yl]-4-(4-methoxyphenyl)phthalazin-1-amine dihydrochloride (compound 130);

N-[1-(4-ethylbenzyl)piperidin-4-yl]-7-methoxy-4-(4-methoxyphenyl)phthalazin-1-amine dihydrochloride (compound 132);

N-[1-(1,3-benzothiazol-6-ylmethyl)piperidin-4-yl]-4-(2,5-dimethoxyphenyl)-7-methoxyphthalazin-1-amine (compound 135);

7-methoxy-N-[1-(2-naphthylmethyl)piperidin-4-yl]-4-(phenoxymethyl)phthalazin-1-amine dihydrochloride (compound 136);

N-[1-(1H-benzimidazol-5-ylmethyl)piperidin-4-yl]-7-methoxy-4-(4-methoxyphenyl)phthalazin-1-amine (compound 138);

7-chloro-4-(4-methoxyphenyl)-N-[1-(2-naphthylmethyl)piperidin-4-yl]phthalazin-1-amine dihydrochloride (compound 143);

4-(4-bromophenyl)-7-methoxy-N-[1-(2-naphthylmethyl) piperidin-4-yl]phthalazin-1-amine dihydrochloride (compound 145);

N-[1-(1,3-benzodioxol-5-ylmethyl)piperidin-4-yl]-7-methoxy-4-(methoxymethyl)phthalazin-1-amine dihydrochloride (compound 146);

4-[(benzyloxy)methyl]-7-methoxy-N-[1-(2-naphthylmethyl)piperidin-4-yl]phthalazin-1-amine dihydrochloride (compound 147);

7-methoxy-5-phenyl-N-[1-(2-naphthylmethyl)piperidin-4-yl]phthalazin-1-amine dihydrochloride (compound 17);

4-(hydroxymethyl)-7-methoxy-N-[1-(2-naphthylmethyl) piperidin-4-yl]-4-(phenoxymethyl)phthalazin-1-amine (compound 148);

(−)-7-methoxy-4-(4-methoxyphenyl)-N-{1-[1-(2-naphthyl)ethyl]piperidin-4-yl}phthalazin-1-amine (compound 149);

(+)-7-methoxy-4-(4-methoxyphenyl)-N-{1-[1-(2-naphthyl)ethyl]piperidin-4-yl}phthalazin-1-amine (compound 150);

N-{1-[4-(dimethylaminomethyl)benzyl]piperidin-4-yl}-7-methoxy-4-(4-methoxyphenyl)phthalazin-1-amine trihydrochloride (compound 151).

In accordance with the invention, the compounds of general formula (I) may be prepared according to the process illustrated by Scheme 1 below.

In Scheme 1, the starting compounds and the reagents, when their mode of preparation is not described, are commercially available or described in the literature, or alternatively may be prepared according to methods described therein or that are known to those skilled in the art.

According to Scheme 1, the compound of general formula (I) is prepared from a compound of general formula (III), in which $R_4$, $R_5$, $R_6$, $R_7$ and $R_8$ are as defined in the general formula (I), according to route A, by nucleophilic substitution of the chlorine with the amine of the compound of general formula (II), in which $R_1$, $R_2$, $R_3$, L, A and B are as defined in the general formula (I). This reaction may be performed by heating the compounds of general formulae (II) and (III) in an alcohol such as n-butanol in the presence of ammonium chloride, according to the method described by Contreras et al. (J. Med. Chem. 2001, 44, 2707-2718), or alternatively may be catalysed with a transition metal such as palladium, for example in the form of tris(dibenzylideneacetone)dipalladium in the presence of a ligand such as BINAP (2,2'-bis (diphenylphosphino)-1,1'-binaphthyl) and a base such as sodium tert-butoxide, according to the method described by Wolfe et al. (J.A.C.S., 1996, 118, 7215-7216).

When $R_3$ is a hydrogen atom, the compound of general formula (I) may also be prepared, according to route B, from the compound of general formula (Ib), in which A, B, $R_4$, $R_5$, $R_6$, $R_7$ and $R_8$ are as defined in the general formula (I) and in which the nitrogen of the nitrogenous ring is not substituted, in particular via a reductive amination reaction with an aldehyde or a ketone of general formula $R_1$-L-C(O)$R_2$, in which L, $R_1$ and $R_2$ are as defined in the general formula (I). This reaction may be performed, for example, in the presence of sodium triacetoxyborohydride in a solvent, for instance dichloromethane or 1,2-dichloroethane according to one of the methods described in Abdel-Magid et al. (J. Org. Chem. 1996, 61, 3849-3862). The compound of general formula (Ib) is obtained by deprotection of the compound of general formula (Ia) that contains on the nitrogen of the nitrogenous ring a protecting group PG. This protecting group may be, for example, a benzyl or a tert-butoxycarbonyl and the deprotection may be performed according to the methods cited in *Protective Groups in Organic Synthesis* 3rd edition, John Wiley & Sons, New York 1999. The compound of general formula (Ia) is synthesized by reacting a compound of general formula (III) as defined above with a compound of general formula (IIa) according to the processes already described previously for the compound (I).

The compound of general formula (IIa), when it is not commercial, may be prepared by analogy with the methods described in the literature (Mach et al., J. Med. Chem. 1993, 36, 3707-3720, Dostert et al., Eur. J. Med. Chem. Ther. 1984, 19(2), 105-110).

The amine of formula (II), when it is not commercial, may be prepared by analogy with the methods mentioned previously for (IIa) and also the methods described in the following publications: Moragues et al. (Farmaco. Ed. Sci. 1980, 35(11), 951-964) and Shum et al. (Nucleosides Nucleotides 2001, 20(4-7), 1067-1078).

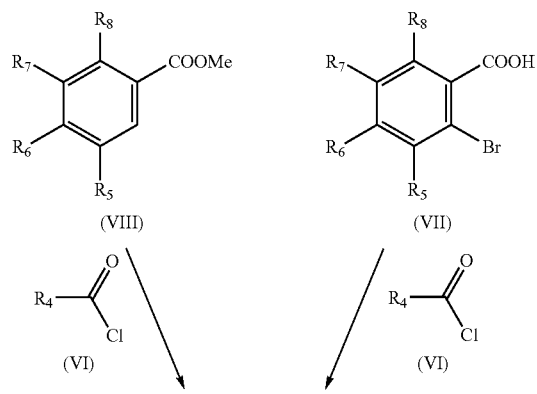

Scheme 1

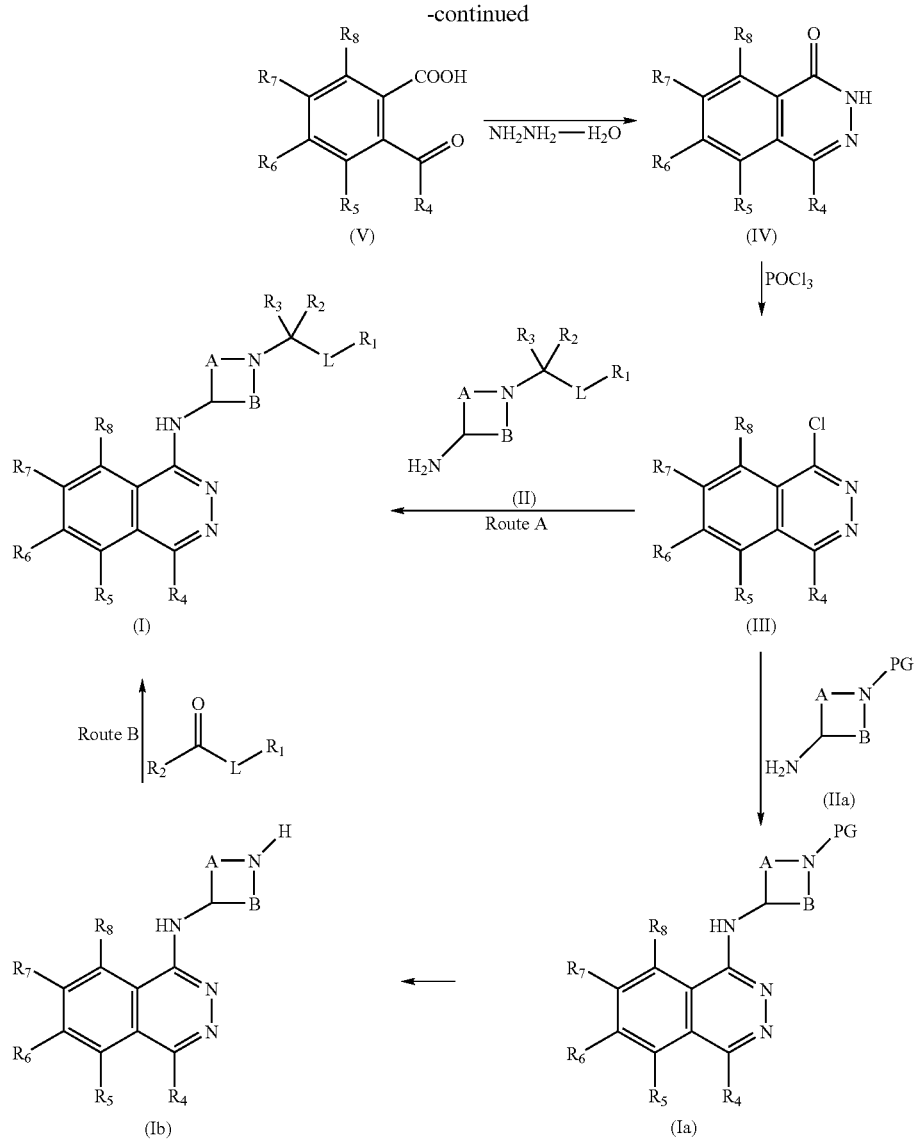

The 1-chlorophthalazine of general formula (III) may be obtained by heating the 2H-phthalazin-1-one of general formula (IV) in phosphoryl chloride for example.

La 2H-phthalazin-1-one of general formula (IV) may be prepared from an acid of 2-acylbenzoic type of general formula (V) by heating in an alcohol, for instance ethanol, in the presence of hydrazine hydrate for example.

The acid of 2-acyl-benzoic type of general formula (V) may be synthesized from an acid of 2-bromobenzoic type of general formula (VII) via halogen-metal exchange followed by reaction with an acid chloride of general formula (VI) or with a Weinreb amide, of N-methoxy, N-methylamine type of formula (VI'):

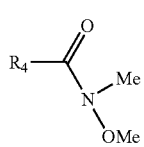
(VI')

The halogen-metal exchange may be performed with n-butyllithium in tetrahydrofuran at −78° C. When $R_4$ represents a hydrogen atom, the acid chloride of general formula (VI) is replaced with dimethylformamide. The compounds of formula (VI') may be obtained from the compound of formula (VI) and N-methoxy-N-methylamine, especially according to the method described by Weinreb (Tetrahedron Letters, (1981), 22(39): 3815-3818).

The acid of 2-acylbenzoic type of general formula (V) may also be obtained via other reactions, for instance the Friedel-Crafts reaction on a compound of general formula (VIII) in the presence of a compound of general formula (VI). This reaction is performed in the presence of aluminium chloride in a solvent such as dichloromethane.

A subject of the invention is also the compounds of formulae (V), (IV) and (III) below:

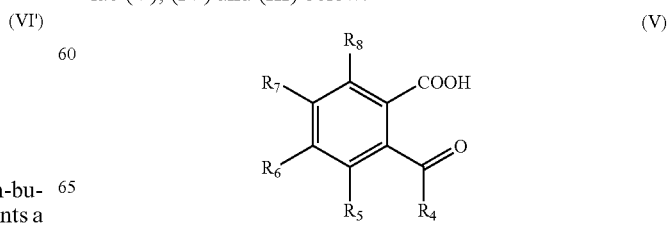
(V)

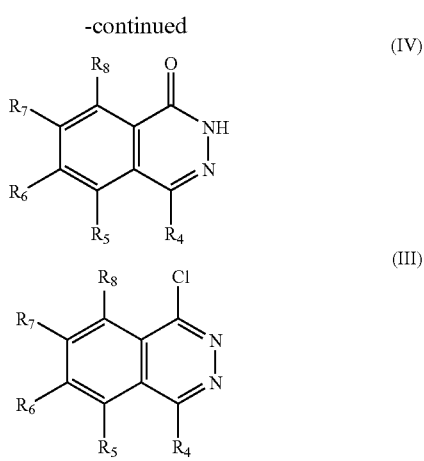

in which $R_4$, $R_5$, $R_6$, $R_7$ and $R_8$ are as defined above for the compounds of formula (I).

Examples of preparation of compounds of formulae (V), (IV) and (III) are given hereinbelow.

The compounds of formula (I) show high affinity and selectivity for the Melanin-Concentrating Hormone (MCH) receptor 1, $MCH_1$.

in vitro tests demonstrated the affinity of the compounds for the MCH receptors and in particular $MCH_1$.

Since MCH is an important regulator of food intake, small non-peptide molecules capable of antagonizing its stimulatory action on the $MCH_1$ receptor constitute a therapy of choice for treating metabolic problems caused by obesity, but also bulimia. Specifically, the use of an $MCH_1$ receptor antagonist such as SNAP-7941 (described by Laboratoires Synaptic) confirms the important role of MCH in regulating the energy balance and the development of obesity (Katsuura et al., Curr. Med. Chem. 2003; 3: 217-227).

The compounds according to the invention thus represent a therapy of choice for the treatment of diseases presenting disorders of regulation of the energy balance and also for treating the development of obesity.

MCH is a functional antagonist of the melanocortin system, which counteracts the effects of the latter on food intake and on the hypothalamo-pituitary-adrenal axis (Ludwig et al., Am. J. Physiol. 1998; 274: E627-E633). It is also involved in regulating the hypothalamo-pituitary-adrenal axis and in the response to stress via the release of hypothalamic CRF (Kennedy et al., J Neuroendocrinol 2003; 15(3): 268-272).

The use of an $MCH_1$ receptor antagonist has recently confirmed the anxiogenic effect of MCH. Specifically, SNAP-7941 has an anxiolytic and/or antidepressant profile in various animal models such as social conflict and forced swimming in rats and also maternal separation in guinea pigs (Katsuura et al., Curr. Med. Chem. 2003; 3: 217-227). $MCH_1$ receptor antagonist molecules are thus of therapeutic value in depression and/or anxiety.

MCH appears to be involved in other regulatory systems. By virtue of its localization in the testicles (Hervieu et al., Biology of Reproduction 1996; 5: 1161-1172) and in the hypothalamus (oestrogen-dependent, Viale et al., Peptides 1999; 20: 553-559) and by virtue of its stimulatory effects on sexual activity in male rats (Gonzales et al., Peptides 1996; 17: 171-177) and its effects on the secretion of luteinizing hormone (Chiocchio et al., Biology of Reproduction 2001; 6: 1466-1472), MCH thus appears to play a role in reproductive functions.

It is also observed that MCH is involved in behaviour associated with cognitive functions by increasing the extinction of passive avoidance in rats, suggesting that an $MCH_1$ receptor antagonist might be useful in the case of memory disorders (MacBride et al., Peptides 1994; 15(4): 757-759). Thus, the compounds according to the invention may constitute a therapy of choice for treating memory disorders.

Thus, the compounds of the invention find their use in therapy, especially in the treatment of obesity, cellulitis, metabolic disorders and associated pathologies thereof such as diabetes, cardiovascular disorders, syndrome X, in the treatment of stress-related pathologies such as anxiety and depression, and also in the treatment of any other disease involving dysfunction related to the $MCH_1$ receptor, whether at the central and/or peripheral level.

Thus, according to another of its aspects, a subject of the invention is medicinal products comprising a compound of formula (I) or an addition salt thereof with a pharmaceutically acceptable acid, or alternatively a hydrate or a solvate.

According to another of its aspects, the present invention relates to pharmaceutical compositions comprising, as active principle, at least one compound according to the invention. These pharmaceutical compositions comprise an effective dose of at least one compound according to the invention, or a pharmaceutically acceptable salt, a hydrate or solvate of the said compound, and also at least one pharmaceutically acceptable excipient. The said excipients are chosen according to the desired pharmaceutical form and mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to man and animals for the prophylaxis or treatment of the above disorders or diseases.

The appropriate unit administration forms comprise oral forms such as tablets, soft or hard gel capsules, powders, granules and oral solutions or suspensions, sublingual, buccal, intratracheal, intraocular and intranasal administration forms, forms for administration by inhalation, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---:|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.5 mg to 800 mg and more particularly from 0.5 mg to 200 mg of active principle per individual, depending on the galenical form.

There may be cases where higher or lower doses are appropriate: such doses are not outside the context of the invention. According to the usual practice, the appropriate dose for each patient is determined by the doctor according to the mode of administration, the weight and the response of the said patient.

According to another of its aspects, the present invention also relates to a method for treating the pathologies indicated above, which comprises the administration, to the patient, of an effective dose of a compound according to the invention, or of a pharmaceutically acceptable salt, hydrate or solvate thereof.

The examples that follow describe the preparation of compounds in accordance with the invention. These examples are not limiting and serve merely to illustrate the present invention. The numbers of the illustrated compounds refer to those given in Table I.

The methods for synthesizing the various intermediates for obtaining the compounds of the invention are described in the preparations. These intermediates are all obtained according to methods that are well known to those skilled in the art.

The melting points (m.p.) are expressed in degrees Celsius. They were measured either using a Köffler apparatus (denoted (K) in the table) or using a Mettler-Toledo FP62 apparatus (denoted (M) in the table) or using a Buchi B540 apparatus (denoted (B) in the table).

The analysis conditions by liquid chromatography coupled to mass spectrometry (LC/UV/MS) are as follows:

For the liquid chromatography part:
  symmetry C18 (2.1×50 mm) 3.5 µm column
  Eluent A=$H_2O$+0.005% TFA, pH=3.14;
  Eluent B=$CH_3CN$+0.005% TFA.
  gradient of from 100% A to 90% B in 10 minutes, then elution with 90% B for 5 minutes.
  flow rate 0.4 ml/min
  injection of 2 µL of solution at a concentration of 0.5 mg/ml in methanol
  the products are detected by UV at 210 nm.

For the mass spectrometry part:
  ionization mode: positive electrospray
  sweep from 120 to 1500 amu.

The LC/MS analytical characteristics of the products are the m/z ratio of the ion $MH^+$ and the retention time (Rt) of the corresponding peak, observed by UV and expressed in minutes.

The proton nuclear magnetic resonance ($^1H$ NMR) spectra were acquired at 250 MHz or at 300 MHz on Brüker machines. The abbreviations used to characterize the signals are as follows: s=singlet, m=multiplet, d=doublet, t=triplet, q=quartet.

The optical rotations of the optically active products are characterized by their $[\alpha]_D^{t°}$ (the concentrations c of the analyzed solutions are expressed in grams per 100 ml).

The quantification of the salts and solvates is determined with the aid of elemental analysis, metering of water by the Karl-Fischer technique and integration of the signals which are characteristic of the solvents in $^1H$ NMR.

The compounds of the invention and their analytical characteristics (m.p., LC/MS, salts and solvates) are listed in table I.

EXAMPLE 1

Compound 1

7-Methoxy-N-[1-(naphthalen-2-ylmethyl)piperidin-4-yl]-4-phenylphthalazin-1-amine 1.1. 2-benzoyl-5-methoxybenzoic acid A solution of 2-bromo-5-methoxybenzoic acid (5 g, 21.6 mmol) in 50 mL of THF is stirred under argon at −78° C., and a 1.6 M solution of n-butyllithium in hexane (29 mL, 45 mmol) is then added dropwise. The reaction mixture is stirred for 1 hour at −78° C. and benzoyl chloride (3.2 g, 22.7 mmol) is then added dropwise. The reaction mixture is stirred for 1 hour 30 minutes at −78° C. and then for 18 hours at room temperature. The mixture is hydrolysed with 100 mL water and then washed with ethyl acetate. The aqueous phase is acidified by addition of 5 N hydrochloric acid and then extracted with ethyl acetate. The organic phase obtained is washed with brine and then dried over anhydrous sodium sulfate. After filtration and evaporation under reduced pressure, 5.4 g of a colourless oil are obtained, and are used without purification.

1.2. 7-Methoxy-4-phenyl-2H-phthalazin-1-one 10.55 g (210 mmol) of hydrazine hydrate are added to a solution of 5.4 g of 2-benzoyl-5-methoxy-benzoic acid in 50 mL of ethanol, and the mixture is refluxed for 2 hours 30 minutes. The reaction medium is cooled and then filtered. The precipitate obtained is washed with ethanol and then dried under reduced pressure at 40° C. 740 mg of product are obtained in the form of a white solid.
  m.p.=215° C. (Köfler block)
  LC/MS: $MH^+$=253 (Rt=7.05 minutes)
  $^1H$ NMR δ in ppm (DMSO d6): 3.97 (s, 3H); 7.48 (dd, $J_1$=8.8 Hz, $J_2$=2.7 Hz, 1H); 7.54-7.60 (m, 5H); 7.64 (d, J=8.8 Hz, 1H); 7.75 (d, J=2.7 Hz, 1H); 12.78 (s, 1H, NH).

1.3. 4-Chloro-6-methoxy-1-phenylphthalazine

7-Methoxy-4-phenyl-2H-phthalazin-1-one (740 mg, 2.9 mmol) is dissolved in 7 mL of phosphoryl chloride. The solution is heated at 80° C. for 2 hours. The reaction medium is cooled to room temperature and then poured slowly into 200 mL of water with stirring. The mixture is then stirred at 5° C., basified with 35% sodium hydroxide solution and then extracted with dichloromethane. The organic phase is washed with water and then with brine and dried over anhydrous sodium sulfate. After filtration and evaporation under reduced pressure, 750 mg of product are obtained in the form of a beige-coloured powder.
  m.p.=199° C. (Mettler FP62)
  LC/MS: $MH^+$=271 (Rt=7.89 minutes)
  $^1H$ NMR δ in ppm (DMSO d6): 4.06 (s, 3H); 7.60-7.64 (m, 4H); 7.67-7.72 (m, 3H); 7.95 (d, J=9.2 Hz, 1H).

1.4. 7-Methoxy-N-[1-(naphthalen-2-ylmethyl)piperidin-4-yl]-4-phenylphthalazin-1-amine 373 mg (1.5 mmol) of 4-amino-1-(naphthalen-2-ylmethyl) piperidine and 69 mg (1.3 mmol) of ammonium chloride are added to a suspension of 350 mg (1.3 mmol) of 4-chloro-6-methoxy-1-phenylphthalazine in 6 mL of n-butanol. The mixture is heated at 135° C. for 20 hours. The reaction medium is cooled to room temperature, hydrolysed with 50 mL of water and then basified to pH 10 with 1 N sodium hydroxide solution. The mixture is then extracted with ethyl acetate. The organic phase is washed with brine, dried over anhydrous sodium sulfate and then evaporated under reduced pressure. The residue obtained is purified by chromatography on a column of silica gel (solvent: 95/5 (v/v) dichloromethane/methanol). The yellow oil thus obtained forms a solid by trituration in isopropyl ether. After filtering and drying, 275 mg of product are obtained in the form of a beige-coloured powder.
  m.p.=121° C. (Köfler block)
  $MH^+$=475 (Rt=5.15 minutes)
  $^1H$ NMR δ in ppm (DMSO d 6): 1.69-1.83 (m, 2H); 2.08-2.25 (m, 4H); 2.96-3.01 (m, 2H); 3.71 (s, 2H); 3.99 (s, 3H);

4.27-4.37 (m, 1H); 7.06 (d, J=7.5 Hz, 1H, NH); 7.44 (dd, J$_1$=8.8 Hz, J$_2$=2.7 Hz, 1H); 7.49-7.59 (m, 8H); 7.73 (d, J=8.8 Hz, 1H); 7.79 (d, J=2.7 Hz, 1H); 7.85-7.95 (m, 4H).

EXAMPLE 2

Compound 11

N-(1-benzylpiperidin-4-yl)-5,7-dimethoxy-4-(4-methoxyphenyl)phthalazin-1-amine

2.1. 3,5-dimethoxy-2-(4-methoxybenzoyl)benzoic acid 5.7 g (43 mmol) of aluminium chloride and then a solution of 4-methoxybenzoyl chloride (5.6 g, 33 mmol) are successively added to a solution of methyl 3,5-dimethoxybenzoate (6.4 g, 33 mmol) in 50 mL of dichloromethane, with stirring at room temperature. The mixture is stirred overnight at room temperature and is then poured into 200 mL of ice-cold water with stirring. The hydrolysed medium is extracted with dichloromethane. The organic phase is washed with saturated sodium hydrogen carbonate solution and then with water, dried over anhydrous sodium sulfate and then evaporated under reduced pressure. The crude extract is purified by chromatography on a column of silica gel (solvent: 3/1 (v/v) cyclohexane/ethyl acetate).

The methyl ester thus obtained is dissolved in 80 mL of methanol, and 17 mL of 2N sodium hydroxide solution are then added. The mixture is stirred overnight at room temperature, and then at 60° C. for 3 hours. The methanol is then evaporated off under reduced pressure. The residual solution is diluted with 100 mL water, acidified by addition of 2N hydrochloric acid and then extracted with dichloromethane. The organic phase is dried over anhydrous sodium sulfate and then evaporated under reduced pressure. A white solid is obtained (5.4 g).

m.p.=191° C. (Mettler FP62)
$^1$H NMR δ in ppm (DMSO d 6): 3.69 (s, 3H); 3.83 (s, 3H); 3.90 (s, 3H); 6.93 (d, J=2.2 Hz, 1H); 9.91-7.03 (m, 2H); 7.09 (d, J=2.2 Hz, 1H); 7.56-7.63 (m, 2H); 13.1 (s, 1H, COOH).

2.2. 5,7-dimethoxy-4-(4-methoxyphenyl)-2H-phthalazin-1-one

This product is prepared from 3,5-dimethoxy-2-(4-methoxybenzoyl)benzoic acid, obtained in step 2.1, according to the method described in step 1.2 of Example 1.

MH$^+$=313 (Rt=7.04 minutes)
$^1$H NMR in ppm (DMSO d 6): 3.55 (s, 3H); 3.82 (s, 3H); 3.96 (s, 3H); 6.9-6.98 (m, 3H); 7.25-7.32 (m, 2H); 7.37 (d, 1H); 12.66 (s, NH).

2.3. 1-chloro-5,7-dimethoxy-4-(4-methoxyphenyl)phthalazine

This product is prepared from 5,7-dimethoxy-4-(4-methoxyphenyl)-2H-phthalazin-1-one, obtained in step 2.2, according to the method described in step 1.3 of Example 1.

MH$^+$=331 (Rt=7.73 minutes)
$^1$H NMR δ in ppm (DMSO d 6): 3.65 (s, 3H); 3.86 (s, 3H); 4.06 (s, 3H); 6.99-7.05 (m, 2H); 7.15 (d, J=2.2 Hz, 1H); 7.22 (d, J=2.2 Hz, 1H); 7.39-7.45 (m, 2H).

2.4. N-(1-benzylpiperidin-4-yl)-5,7-dimethoxy-4-(4-methoxyphenyl)phthalazin-1-amine 400 mg (1.2 mmol) of 4-chloro-6,8-dimethoxy-1-(4-methoxyphenyl)phthalazine dissolved in 5 mL of toluene, 276 mg (1.4 mmol) of 4-amino-1-benzylpiperidine, 163 mg (1.7 mmol) of sodium tert-butoxide, 6 mg (0.009 mmol) of BINAP (2,2'-bis(diphenylphosphino)-1,1'-binaphthyl) and 5.5 mg (0.006 mmol) of tris(dibenzylideneacetone)dipalladium are successively introduced into a tube under argon. The tube is hermetically sealed and the mixture is stirred at 80° C. for 24 hours. After cooling to room temperature, the reaction medium is hydrolysed with sodium hydrogen carbonate solution and then extracted with ethyl acetate. The organic phase is washed with water and with brine, dried over anhydrous sodium sulfate and then evaporated under reduced pressure. The residue obtained is purified by chromatography on a column of silica gel (solvent: 95/5 (v/v) dichloromethane/methanol). The oily product obtained forms a solid by trituration in ethyl ether. 270 mg of product are obtained in the form of a beige-coloured powder.

m.p.=168° C. (Köffler)
MH$^+$=485 (Rt=4.82 minutes)
$^1$H NMR δ in ppm (DMSO d 6): 1.67-1.76 (m, 2H); 2.04-2.17 (m, 4H); 2.90-2.94 (m, 2H); 3.54 (s, 5H); 3.82 (s, 3H); 3.98 (s, 3H); 4.20-4.30 (m, 1H); 6.84 (d, 1H, NH); 6.88-6.96 (m, 3H); 7.23-7.37 (m, 8H).

EXAMPLE 3

Compound 7

N-(1-benzylpiperidin-4-yl)-7-methoxy-4-(4-methoxyphenyl)phthalazin-1-amine

3.1. N,4-dimethoxy-N-methylbenzamide 14.7 g (151 mmol) of N,O-dimethylhydroxylamine hydrochloride are added portionwise to a solution of 25 g (147 mmol) of 4-methoxybenzoyl chloride in 450 mL of dichloromethane, stirred at 0-5° C. under nitrogen. 51 mL (370 mmol) of triethylamine are then added slowly to the mixture stirred at 0-5° C. The orange-coloured reaction medium is stirred at room temperature for 3 hours. The mixture is hydrolysed with 250 mL of water and then extracted with dichloromethane. The organic phase is washed with 100 mL of 1N HCl, 150 mL of 1N NaOH and then with water and brine. It is dried over anhydrous sodium sulfate, filtered and evaporated to dryness. 26.9 g of an orange-coloured oil are obtained, and are purified on a column of silica, eluting with dichloromethane and then with a 95/5 dichloromethane/methanol mixture. 25.4 g of a yellow oil are obtained (89% yield).

LC/MS: MH$^+$=196 (Rt=5.21 minutes)
$^1$H NMR δ in ppm (DMSO d 6): 3.26 (s, 3H); 3.56 (s, 3H); 3.82 (s, 3H); 7.00 (d, J=8.5 Hz, 2H); 7.63 (d, J=8.5 Hz, 2H).

3.2. 5-methoxy-2-(4-methoxybenzoyl)benzoic acid

A solution of 18.5 g (80 mmol) of 2-bromo-5-methoxybenzoic acid in 150 mL of tetrahydrofuran is stirred under nitrogen at −78° C. in a bath of cardice/acetone. 100 mL (160 mmol) of a 1.6M solution of n-butyllithium in hexane are added dropwise over about 1 hour, while taking care to ensure that the temperature does not exceed −70° C. About half way through the introduction, the formation of a beige-coloured precipitate that corresponds to the formation of the lithium carboxylate is noted. After the addition, the mixture is stirred at −78° C. for 1 hour, and a solution of 15.9 g (80 mmol) of N,4-dimethoxy-N-methylbenzamide in 20 mL of THF is added dropwise. The reaction medium is stirred at −78° C. for 1 hour and the bath of cardice/acetone is then removed and the reaction medium is stirred, while allowing the temperature to return gradually to room temperature, for 18 hours. The mixture is hydrolysed with 100 mL of water, basified to pH=12 with 2N NaOH solution and then extracted with tert-butyl methyl ether. The aqueous phase containing the carboxylate is acidified with 5N HCl solution to pH 1 and extracted with dichloromethane. The dichloromethane phase is washed with brine, dried over anhydrous sodium sulfate, filtered and evaporated. The product is crystallized from isopropyl ether; after filtering and drying, 14.6 g of white crystals are obtained (yield=64%).

m.p.=170° C. (Mettler FP62)

LC/MS: MH$^+$=287 (Rt=7.07 minutes)

$^1$H NMR δ in ppm (DMSO d 6): 3.85 (s, 3H); 3.90 (s, 3H); 7.03 (d, J=8.5 Hz, 2H); 7.24 (dd, J$_1$=8.5 Hz, J$_2$=2.5 Hz, 1H); 7.35 (d, J=8.5 Hz, 1H); 7.42 (d, J=2.5 Hz, 1H); 7.61 (d, J=8.5 Hz, 2H); 13.1 (s, 1H, COOH).

3.3. 7-Methoxy-4-(4-methoxyphenyl)-2H-phthalazin-1-one 18.5 mL (380 mmol) of hydrazine hydrate are added to a solution of 21.6 g (75 mmol) of 5-methoxy-2-(4-methoxybenzoyl)benzoic acid in 150 mL of ethanol and the mixture is refluxed for 2 hours. The reaction medium is cooled and then filtered. The precipitate obtained is washed with ethanol and then dried under reduced pressure at 40° C. 19 g of a white solid are obtained (90% yield).

m.p.=245° C. (Mettler FP62)

LC/MS: MH$^+$=283 (Rt=6.98 minutes)

$^1$H NMR δ in ppm (DMSO d 6): 3.86 (s, 3H); 3.98 (s, 3H); 7.12 (d, J=8.5 Hz, 2H); 7.48 (dd, J$_1$=9 Hz, J$_2$=2.7 Hz, 1H); 7.52 (d, J=8.5 Hz, 2H); 7.67 (d, J=9.0 Hz, 1H); 7.75 (d, J=2.7 Hz, 1H); 12.72 (s, 1H, NH).

3.4. 1-Chloro-7-methoxy-4-(4-methoxyphenyl)phthalazine 19 g (67 mmol) of 7-methoxy-4-(4-methoxyphenyl)-2H-phthalazin-1-one are dissolved in 100 mL of phosphoryl chloride. The solution is heated at 80° C. for 2 hours. The reaction medium is cooled to room temperature and then poured slowly into 500 mL of water at 40-50° C. with stirring. The mixture is then stirred at 5° C., basified by addition of 35% sodium hydroxide solution and then extracted with dichloromethane. The organic phase is washed with water and then with brine and dried over anhydrous sodium sulfate. After filtration and evaporation under reduced pressure, 19.3 g of a beige-coloured powder are obtained (yield=96%).

m.p.=173° C.

LC/MS: MH$^+$=301 (Rt=8.52 minutes)

$^1$H NMR δ in ppm (DMSO d 6): 3.90 (s, 3H); 4.07 (s, 3H); 7.19 (d, J=8.5 Hz, 2H); 7.60 (d, J=2.5 Hz, 1H); 7.68(d, J=8.5 Hz, 2H); 7.72 (dd, J$_1$=9.2 Hz, J$_2$=2.5 Hz, 1H); 8.02 (d, J=9.2 Hz, 1H).

3.5. 1-(1-Benzylpiperidin-4-yl)-7-methoxy-4-(4-methoxyphenyl)phthalazin-1-amine 10.1 g (53 mmol) of (4-amino-1-benzyl)piperidine and 1.44 g (27 mmol) of ammonium chloride are added to a suspension of 8 g (26.6 mmol) of 1-chloro-7-methoxy-4-(4-methoxyphenyl)phthalazine in 50 mL of 1-butanol. The mixture is refluxed (oil bath at 140° C.) for 7 hours. The reaction medium is cooled to room temperature, hydrolysed with 50 mL of saturated aqueous sodium hydrogen carbonate solution and then extracted with ethyl acetate. The organic phase is washed with brine, dried over anhydrous sodium sulfate and then evaporated under reduced pressure. The residue obtained is purified by chromatography on a column of silica gel (solvent: 95/5 (v/v) dichloromethane/methanol). The yellow oil thus obtained forms a solid by trituration in isopropyl ether. After filtering and drying, 10.5 g of white powder are obtained (yield=87%).

m.p.=150° C. (Mettler FP62)

LC/MS: MH$^+$=455 (Rt=4.71 minutes)

$^1$H NMR δ in ppm (DMSO d 6): 1.7-1.8 (m, 2H); 2.0-2.2 (m, 4H); 2.90-3.0 (m, 2H); 3.54 (s, 2H); 3.86 (s, 3H); 4.0 (s, 3H); 4.2-4.3 (m, 1H); 7.0 (d, J=7.5 Hz; 1H, NH); 7.10 (d, J=8.5 Hz, 2H); 7.25-7.40 (m, 5H); 7.43 (dd; J$_1$=9.0 Hz; J$_2$=2.5 Hz, 1H); 7.53 (d, J=8.5 Hz, 2H); 7.75-7.77 (m, 2H).

EXAMPLE 4

Compound 4

7-Methoxy-4-(4-methoxyphenyl)-N-[8-(naphthalen-2-ylmethyl)-8-azabicyclo[3.2.1]oct-3-yl]phthalazin-1-amine

4.1. N-[8-(naphthalen-2-ylmethyl)-8-azabicyclo[3.2.1]oct-3-yl]acetamide 1.6 g (9.5 mmol) of N-[8-azabicyclo[3.2.1]oct-3-yl]acetamide prepared according to Dostert et al. (European Journal of Medicinal Chemistry 1984, 19 (2), 105-110) are dissolved in 45 mL of acetone, and 5.2 g of potassium carbonate and 2.5 g (11.4 mmol) of 2-(bromomethyl)naphthalene are added. The mixture is refluxed with stirring for 18 hours. After cooling, the acetone is partially evaporated off. Water is added to the residue, and the mixture is extracted with dichloromethane. The organic phase is extracted with 1N hydrochloric acid. The acidic aqueous phase obtained is basified with 1N sodium hydroxide and then extracted with dichloromethane. The extract is washed with water and with brine, dried over anhydrous sodium sulfate and then evaporated under reduced pressure. The residue obtained is filtered on silica gel (solvent: 95/5 (v/v) dichloromethane/methanol). 2.2 g of a pasty oil are obtained (84% yield).

LC/MS: MH$^+$=309 (Rt=4.49 minutes)

$^1$H NMR δ in ppm (DMSO d 6): 1.5-1.65 (m, 6H); 1.77 (s, 3H); 2.0-2.1 (m, 2H); 3.1-3.2 (m, 2H); 3.70 (s, 2H); 3.9-4.0 (m, 1H); 7.4-7.6 (m, 3H); 7.7 (d, J=8.2 Hz, 1H, NH); 7.82-7.95 (m, 4H).

4.2. N-[8-(naphthalen-2-ylmethyl)-8-azabicyclo[3.2.1]oct-3-yl]amine 4 g (12.9 mmol) of N-[8-(naphthalen-2-ylmethyl)-8-azabicyclo[3.2.1]oct-3-yl]acetamide are poured into 13 mL of 5N hydrochloric acid. The mixture is refluxed for 4 hours and then cooled in an ice bath, basified with 35% sodium hydroxide and extracted three times with ethyl acetate. The combined extracts are washed with water and with brine, dried over anhydrous sodium sulfate and then evaporated under reduced pressure. 3.2 g of oily product are obtained (94% yield).

LC/MS: MH$^+$=267(Rt=1.71 minutes)

$^1$H NMR δ in ppm (DMSO d 6): 1.3-1.45 (m, 2H); 1.5-1.65 (m, 6H); 1.9-2.05 (m, 2H); 2.8 (m, 1H, CH axial); 3.1-3.2 (m, 2H); 3.65 (s, 2H); 7.4-7.6 (m, 3H); 7.75-7.9 (m, 4H).

4.3. 7-Methoxy-4-(4-methoxyphenyl)-N-[8-(naphthalen-2-ylmethyl)-8-azabicyclo[3.2.1]oct-3-yl]phthalazin-1-amine This compound is obtained according to the procedure described in 1.4. by reacting N-[8-(naphthalen-2-ylmethyl)-

8-azabicyclo[3.2.1]oct-3-yl]amine and 1-chloro-7-methoxy-4-(4-methoxyphenyl)phthalazine.

EXAMPLE 5

Compound 8

N-(1-benzylpiperidin-4-yl)-7-methoxy-4-(thiophen-2-yl)phthalazin-1-amine 5.1. 5-Methoxy-2-(thiophene-2-carbonyl)benzoic acid This compound is obtained according to the procedure described in 1.1. by reacting thiophene-2-carboxylic acid chloride and 2-bromo-5-methoxybenzoic acid after halogen-lithium exchange. It is used in crude form in the following reaction.

5.2. 7-Methoxy-4-(thiophen-2-yl)-2H-phthalazin-1-one

This compound is obtained according to the procedure described in 1.2. by reacting unpurified 5-methoxy-2-(thiophene-2-carbonyl)benzoic acid with hydrazine hydrate.
LC/MS: MH$^+$=259 (Rt=7.50 minutes)

5.3. 1-Chloro-7-methoxy-4-(thiophen-2-yl)phthalazine

This compound is obtained according to the procedure described in 1.3. by reacting 7-methoxy-4-(thiophen-2-yl)-2H-phthalazin-1-one with phosphoryl chloride.
m.p.=199° C. (Mettler FP62)
LC/MS: MH$^+$=277 (Rt=7.99 minutes)
$^1$H NMR δ in ppm (DMSO d 6): 4.07 (s, 3H); 7.34-7.38 (m, 1H); 7.60 (d, J=2.7 Hz, 1H); 7.78 (dd, J$_1$=9.2 Hz, J$_2$=2.7 Hz, 1H); 7.86 (d, J=3.7 Hz, 1H); 7.95 (d, J=5.2 Hz, 1H); 8.50 (d, J=9.2 Hz, 1H).

5.4. N-(1-benzylpiperidin-4-yl)-7-methoxy-4-(thiophen-2-yl)phthalazin-1-amine

This compound is obtained according to the procedure described in 1.4. by reacting 1-chloro-7-methoxy-4-(thiophen-2-yl)phthalazine with 4-amino-1-benzylpiperidine.

EXAMPLE 6

Compound 16

N-(1-benzylpiperidin-4-yl)-7-methoxy-4-(5-methylthiophen-2-yl)phthalazin-1-amine 6.1. 5-methoxy-2-(5-methylthiophene-2-carbonyl)benzoic acid This compound is obtained according to the procedure described in 1.1. by reacting 5-methylthiophen-2-yl chloride and 2-bromo-5-methoxybenzoic acid after halogen-lithium exchange. It is used in crude form in the following reaction.

6.2. 7-Methoxy-4-(5-methylthiophen-2-yl)-2H-phthalazin-1-one

This compound is obtained according to the procedure described in 1.2. by reacting unpurified 5-methoxy-2-(5-methylthiophene-2-carbonyl)benzoic acid with hydrazine hydrate.
LC/MS: MH$^+$=273 (Rt=7.58 minutes)

6.3. 1-Chloro-7-methoxy-4-(5-methylthiophen-2-yl)phthalazine

This compound is obtained according to the procedure described in 1.3. by reacting 7-methoxy-4-(5-methylthiophen-2-yl)-2H-phthalazin-1-one with phosphoryl chloride.
LC/MS: MH$^+$=291 (Rt=8.74 minutes)
$^1$H NMR δ in ppm (DMSO d 6): 2.59 (s, 3H); 4.08 (s, 3H); 7.06 (m, 1H); 7.60 (d, J=2.7 Hz, 1H); 7.68 (d, J=3.5 Hz, 1H); 7.77 (dd, J$_1$=9.2 Hz, J$_2$=2.7 Hz, 1H); 8.51 (d, J=9.2 Hz, 1H).

6.4. N-(1-benzylpiperidin-4-yl)-7-methoxy-4-(5-methylthiophen-2-yl)phthalazin-1-amine This compound is obtained according to the procedure described in 1.4. by reacting 1-chloro-7-methoxy-4-(5-methylthiophen-2-yl)phthalazine with 4-amino-1-benzylpiperidine.

EXAMPLE 7

Compound 6

N-(1-benzylpiperidin-4-yl)-7-methoxy-4-(3-methoxyphenyl)phthalazin-1-amine 7.1 5-methoxy-2-(3-methoxybenzoyl)benzoic acid This compound is obtained according to the procedure described in 1.1. by reacting 3-methoxybenzoyl chloride and 2-bromo-5-methoxybenzoic acid after halogen-lithium exchange. It is used in crude form in the following reaction.

7.2. 7-Methoxy-4-(3-methoxyphenyl)-2H-phthalazin-1-one

This compound is obtained according to the procedure described in 1.2. by reacting unpurified 5-methoxy-2-(3-methoxybenzoyl)benzoic acid with hydrazine hydrate.
m.p.=219° C. (Mettler FP62)
LC/MS: MH$^+$=283 (Rt=7.41 minutes)
1H NMR δ in ppm (DMSO d6): 3.83 (s, 3H); 3.97 (s, 3H); 7.10-7.16 (m, 3H); 7.44-7.51 (m, 2H); 7.67 (d, J=9 Hz, 1H); 7.75 (d, J=2.5 Hz, 1H); 12.80 (s, 1H, NH).

7.3. 1-Chloro-7-methoxy-4-(3-methoxyphenyl)phthalazine

This compound is obtained according to the procedure described in 1.3. by reacting 7-methoxy-4-(3-methoxyphenyl)-2H-phthalazin-1-one with phosphoryl chloride.
m.p.=98° C. (Mettler FP62)
LC/MS: MH$^+$=301 (Rt=8.07 minutes)
$^1$H NMR δ in ppm (DMSO d 6): 3.86 (s, 3H); 4.08 (s, 3H); 7.18-7.27 (m, 3H); 7.52-7.58 (m, 1H); 7.62 (d, J=2.5 Hz, 1H); 7.72 (dd, J$_1$=9.2 Hz, J$_2$=2.5 Hz, 1H); 8.02 (d, J=9.2 Hz, 1H).

7.4. 1-(1-Benzylpiperidin-4-yl)-7-methoxy-4-(3-methoxyphenyl)phthalazin-1-amine

This compound is obtained according to the procedure described in 1.4. by reacting 1-chloro-7-methoxy-4-(3-methoxyphenyl)phthalazine with 4-amino-1-benzylpiperidine.

EXAMPLE 8

Compound 3

7-methoxy-4-(4-methoxyphenyl)-N-[1-(naphthalen-2-ylmethyl)piperidin-4-yl]phthalazin-1-amine This compound is obtained according to the procedure described in 1.4. by reacting 1-chloro-7-methoxy-4-(4-methoxyphenyl)phthalazine described in 3.4 with 4-amino-1-(naphthalen-2-ylmethyl)piperidine.

EXAMPLE 9

Compound 5

7-methoxy-4-(3-methoxyphenyl)-N-[1-(naphthalen-2-ylmethyl)piperidin-4-yl]phthalazin-1-amine This compound is obtained according to the procedure described in 1.4. by reacting 1-chloro-7-methoxy-4-(3-methoxyphenyl)phthalazine described in 7.3 with 4-amino-1-(naphthalen-2-ylmethyl)piperidine.

EXAMPLE 10

Compound 2

7-methoxy-4-(2-methoxyphenyl)-N-[1-(naphthalen-2-ylmethyl)piperidin-4-yl]phthalazin-1-amine

10.1. 5-methoxy-2-(2-methoxybenzoyl)benzoic acid

This compound is obtained according to the procedure described in 1.1. by reacting 2-methoxybenzoyl chloride and 2-bromo-5-methoxybenzoic acid after halogen-lithium exchange. It is used in crude form in the following reaction.

10.2. 7-Methoxy-4-(2-methoxyphenyl)-2H-phthalazin-1-one

This compound is obtained according to the procedure described in 1.2. by reacting unpurified 5-methoxy-2-(2-methoxybenzoyl)benzoic acid with hydrazine hydrate.

m.p.=275° C. (Mettler FP62)
LC/MS: MH$^+$=283 (Rt=7.76 minutes)
1H NMR δ in ppm (DMSO d 6): 3.70 (s, 3H); 3.96 (s, 3H); 7.11-7.15 (m, 1H); 7.20-7.23 (d, J=8.7 Hz, 2H); 7.32-7.35 (m, 1H); 7.39-7.44 (m, 1H); 7.50-7.55 (m, 1H); 7.69 (d, J=2.7 Hz, 1H); 12.70 (s, 1H, NH)

10.3. 1-Chloro-7-methoxy-4-(2-methoxyphenyl)phthalazine

This compound is obtained according to the procedure described in 1.3. by reacting 7-methoxy-4-(2-methoxyphenyl)-2H-phthalazin-1-one with phosphoryl chloride.

m.p.=157° C. (Mettler FP62)
LC/MS: MH$^+$=301 (Rt=7.81 minutes)
$^1$H NMR δ in ppm (DMSO d 6): 3.69 (s, 3H); 4.06 (s, 3H); 7.15-7.22 (m, 1H); 7.28 (d, J=7.6 Hz, 1H); 7.42 (dd, J$_1$=7.6 Hz, J$_2$=1.7 Hz, 1H); 7.55-7.68 (m, 4H).

10.4. 7-methoxy-4-(2-methoxyphenyl)-N-[1-(naphthalen-2-ylmethyl)piperidin-4-yl]phthalazin-1-amine This compound is obtained according to the procedure described in 1.4. by reacting 1-chloro-7-methoxy-4-(2-methoxyphenyl)phthalazine described with 4-amino-1-(naphthalen-2-ylmethyl)piperidine.

EXAMPLE 11

Compound 10

4-(3,4-Dimethoxyphenyl)-7-methoxy-N-[1-(naphthalen-2-ylmethyl)piperidin-4-yl]phthalazin-1-amine

11.1 2-(3,4-dimethoxybenzoyl)-5-methoxybenzoic acid

This compound is obtained according to the procedure described in 1.1. by reacting 3,4-dimethoxybenzoyl chloride and 2-bromo-5-methoxybenzoic acid after halogen-lithium exchange. It is used in crude form in the following reaction.

11.2. 4-(3,4-Dimethoxyphenyl)-7-methoxy-2H-phthalazin-1-one

This compound is obtained according to the procedure described in 1.2. by reacting unpurified 2-(3,4-dimethoxybenzoyl)-5-methoxybenzoic acid with hydrazine hydrate.

m.p.=258° C. (Mettler FP62)
LC/MS: MH$^+$=313 (Rt=6.54 minutes)
$^1$H NMR δ in ppm (DMSO d 6): 3.81 (s, 3H); 3.86 (s, 3H); 3.97 (s, 3H); 7.12-7.16 (m, 3H); 7.48 (dd, J$_1$=9 Hz, J$_2$=2.7 Hz, 1H) 7.71-7.76 (m, 2H); 12.71 (s, 1H, NH).

11.3. 1-Chloro-4-(3,4-dimethoxyphenyl)-7-methoxyphthalazine

This compound is obtained according to the procedure described in 1.3. by reacting 4-(3,4-dimethoxyphenyl)-7-methoxy-2H-phthalazin-1-one with phosphoryl chloride.

m.p.=190° C. (Mettler FP62)
LC/MS: MH$^+$=331 (Rt=7.43 minutes)
$^1$H NMR δ in ppm (DMSO d 6): 3.85 (s, 3H); 3.89 (s, 3H); 4.08 (s, 3H); 7.18-7.32 (m, 3H); 7.61 (d, J=2.5 Hz, 1H); 7.72 (dd, J$_1$=9.2 Hz, J$_2$=2.5 Hz, 1H); 8.01 (d, J=9.2 Hz, 1H).

11.4. 4-(3,4-Dimethoxyphenyl)-7-methoxy-N-[1-(naphthalen-2-ylmethyl)piperidin-4-yl]phthalazin-1-amine This compound is obtained according to the procedure described in 1.4. by reacting 1-chloro-4-(3,4-dimethoxyphenyl)-7-methoxyphthalazine with 4-amino-1-(naphthalen-2-ylmethyl)piperidine.

EXAMPLE 12

Compound 15

5,7-dimethoxy-4-(4-methoxyphenyl)-N-[1-(naphthalen-2-ylmethyl)piperidin-4-yl]phthalazin-1-amine dihydrochloride This compound is obtained according to the procedure described in 2.4 by reacting 4-chloro-6,8-dimethoxy-1-(4-methoxyphenyl)phthalazine described in 2.3 with 4-amino-1-(naphthalen-2-ylmethyl)piperidine. On treatment with hydrochloric ether, a precipitate forms, which is filtered off, washed with ethyl ether and dried under reduced pressure. The hydrochloride obtained is in the form of a white solid.

EXAMPLE 13

Compound 13

N-(1-benzylpiperidin-4-yl)-5,7-dimethoxyphthalazin-1-amine

13.1. 5,7-Dimethoxy-2H-phthalazin-1-one 3 g (13.4 mmol) of methyl 2-formyl-3,5-dimethoxybenzoate are dissolved in 80 mL of methanol and 10 mL of 2N sodium hydroxide solution. The mixture is stirred for 18 hours at room temperature. The methanol is evaporated off under reduced pressure and the concentrate is acidified with 2N hydrochloric acid. The precipitate formed is filtered off and then dried. 2.7 g of acid in the form of a yellow solid are obtained.

The 2-formyl-3,5-dimethoxybenzoic acid (2.7 g, 13 mmol) is partially dissolved in 300 mL of ethanol, and 6.2 mL of hydrazine hydrate are then added. The mixture is refluxed for 6 hours. After cooling, the precipitate formed is filtered off and then dried. 2.3 g of a white solid are obtained (86% yield).

LC/MS: MH$^+$=207 (Rt=5.35 minutes)

$^1$H NMR δ in ppm (DMSO d 6): 3.95 (s, 3H); 3.98 (s, 3H); 7.02 (d, J=2.5 Hz, 1H); 7.21 (d, J=2.5 Hz, 1H); 8.30 (s, 1H); 12.61 (s, 1H, NH)

13.2. 1-Chloro-5,7-dimethoxyphthalazine 1 g (4.9 mmol) of 5,7-dimethoxy-2H-phthalazin-1-one and 10 mL of phosphoryl chloride are heated at 80° C. for 2 hours. After cooling to room temperature, the reaction medium is poured dropwise into 50 mL of water and the mixture is then basified with 6N sodium hydroxide solution and extracted with dichloromethane. The organic phase is washed with water and with brine, dried over anhydrous sodium sulfate and then evaporated under reduced pressure. 1 g of a beige-coloured solid is obtained (91% yield).

m.p.=167° C. (Mettler FP62)

LC/MS: MH$^+$=225 (Rt=6.15 minutes)

$^1$H NMR δ in ppm (DMSO d 6): 4.03 (s, 3H); 4.06 (s, 3H); 7.04 (d, J=2.2 Hz, 1H); 7.15 (d, J=2.2 Hz, 1H); 9.49 (s, 1H).

13.3. N-(1-benzylpiperidin-4-yl)-5,7-dimethoxyphthalazin-1-amine

This compound is obtained according to the procedure described in 2.4 by reacting 1-chloro-5,7-dimethoxyphthalazine with 4-amino-1-benzylpiperidine.

EXAMPLE 14

Compound 14

5,7-dimethoxy-N-[1-(naphthalen-2-ylmethyl)piperidin-4-yl]phthalazin-1-amine

This compound is obtained according to the procedure described in 2.4 by reacting 1-chloro-5,7-dimethoxyphthalazine described in 13.2 with 4-amino-1-(naphthalen-2-ylmethyl)piperidine.

EXAMPLE 15

Compound 9

4-(4-methoxyphenyl)-7-methyl-N-[1-(naphthalen-2-ylmethyl)piperidin-4-yl]phthalazin-1-amine

15.1 2-(4-methoxybenzoyl)-5-methylbenzoic acid

This compound is obtained according to the procedure described in 1.1. by reacting 4-methoxybenzoyl chloride and 2-bromo-5-methylbenzoic acid after halogen-lithium exchange. It is used in crude form in the following reaction.

15.2. 4-(4-Methoxyphenyl)-7-methyl-2H-phthalazin-1-one

This compound is obtained according to the procedure described in 1.2. by reacting unpurified 2-(4-methoxybenzoyl)-5-methylbenzoic acid with hydrazine hydrate.

LC/MS: MH$^+$=267 (Rt=7.29 minutes)

$^1$H NMR δ in ppm (DMSO d 6): 2.55 (s, 3H); 3.86 (s, 3H); 7.12 (d, J=8.5 Hz, 2H); 7.53 (d, J=8.5 Hz, 2H); 7.62 (d, J=8.2 Hz, 1H); 7.74 (dd, J$_1$=8.2 Hz, J$_2$=2 Hz, 1H); 8.16 (d, J=2 Hz, 1H); 12.7 (s, 1H, NH).

15.3. 1-Chloro-4-(4-methoxyphenyl)-7-methylphthalazine

This compound is obtained according to the procedure described in 1.3. by reacting 4-(4-methoxyphenyl)-7-methyl-2H-phthalazin-1-one with phosphoryl chloride.

m.p.=154° C. (Mettler FP62)

LC/MS: MH$^+$=285 (Rt=8.36 minutes)

$^1$H NMR δ in ppm (DMSO d 6): 2.67 (s, 3H); 3.90 (s, 3H); 7.20 (d, J=8.5 Hz, 2H); 7.70 (d, J=8.5 Hz, 2H); 7.95-7.99 (m, 2H); 8.18 (m, 1H).

15.4. 4-(4-methoxyphenyl)-7-methyl-N-[1-(naphthalen-2-ylmethyl)piperidin-4-yl]phthalazin-1-amine This compound is obtained according to the procedure described in 1.4. by reacting 1-chloro-4-(4-methoxyphenyl)-7-methylphthalazine with 4-amino-1-(naphthalen-2-ylmethyl)piperidine.

EXAMPLE 16

Compound 20

4-Ethyl-7-methoxy-N-[1-(naphthalen-2-ylmethyl)piperidin-4-yl]phthalazin-1-amine

16.1. 5-methoxy-2-propionylbenzoic acid

This compound is synthesized according to the method described in 3.2. by reacting 2-bromo-5-methoxybenzoic acid pretreated with n-butyllithium with N-methoxy-N-methylpropionamide. It is used in crude form in the following reaction.

16.2. 4-Ethyl-7-methoxy-2H-phthalazin-1-one

This compound is obtained according to the procedure described in 1.2. by reacting unpurified 5-methoxy-2-propionylbenzoic acid with hydrazine hydrate.

LC/MS: MH$^+$=205 (Rt=6.32 minutes)

$^1$H NMR δ in ppm (DMSO d 6): 1.25 (t, J=7.5 Hz, 3H); 2.92 (q, J=7.5 Hz, 2H); 3.94 (s, 3H); 7.50 (dd, J$_1$=9 Hz, J$_2$=2.7 Hz, 1H); 7.60 (d, J=2.7 Hz, 1H); 7.94 (d, J=9 Hz, 1H); 12.38 (s, 1H, NH).

16.3. 1-Chloro-4-ethyl-7-methoxyphthalazine

This compound is obtained according to the procedure described in 1.3. by reacting 4-ethyl-7-methoxy-2H-phthalazin-1-one with phosphoryl chloride.

m.p.=191° C. (Mettler FP62)

LC/MS: MH$^+$=223 (Rt=6.84 minutes)

¹H NMR δ in ppm (DMSO d 6): 1.36 (t, J=7.5 Hz, 3H); 3.30 (q, J=7.5 Hz, 2H); 4.04 (s, 3H); 7.50 (d, J=2.7 Hz, 1H); 7.71 (dd, J₁=9 Hz, J₂=2.7 Hz, 1H); 8.30 (d, J=9 Hz, 1H).

16.4. 4-Ethyl-7-methoxy-N-[1-(naphthalen-2-ylmethyl)piperidin-4-yl]phthalazin-1-amine This compound is obtained according to the procedure described in 1.4. by reacting 1-chloro-4-ethyl-7-methoxyphthalazine with 4-amino-1-(naphthalen-2-ylmethyl)piperidine.

EXAMPLE 17

Compound 21

4-Benzyl-7-methoxy-N-[1-(naphthalen-2-ylmethyl)piperidin-4-yl]phthalazin-1-amine 17.1. 5-methoxy-2-(phenylacetyl)benzoic acid This compound is synthesized according to the method described in 3.2. by reacting 2-bromo-5-methoxybenzoic acid pretreated with n-butyllithium with phenyl-N-methoxy-N-acetamide. It is used in crude form in the following reaction.

17.2. 4-Benzyl-7-methoxy-2H-phthalazin-1-one

This compound is obtained according to the procedure described in 1.2. by reacting unpurified 5-methoxy-2-(phenylacetyl)benzoic acid with hydrazine hydrate.
LC/MS: MH⁺=267 (Rt=6.50 minutes) ¹H NMR δ in ppm (DMSO d 6): 3.92 (s, 3H); 4.27 (s, 2H); 7.15-7.33 (m, 5H); 7.44 (dd, J₁=8.8 Hz, J₂=2.7 Hz, 1H); 7.66 (d, J=2.7 Hz, 1H); 7.90 (d, J=8.8 Hz, 1H); 12.52 (s, 1H, NH).

17.3. 4-Benzyl-1-chloro-7-methoxyphthalazine

This compound is obtained according to the procedure described in 1.3. by reacting 4-benzyl-7-methoxy-2H-phthalazin-1-one with phosphoryl chloride.
LC/MS: MH⁺=285 (Rt=7.34 minutes)
¹H NMR δ in ppm (DMSO d 6): 4.02 (s, 3H); 4.68 (s, 2H); 7.17-7.35 (m, 5H); 7.52 (d, J=2.5 Hz, 1H); 7.69 (dd, J₁=9.2 Hz, J₂=2.5 Hz, 1H); 8.31 (d, J=9.2 Hz, 1H).

17.4. 4-Benzyl-7-methoxy-N-[1-(naphthalen-2-ylmethyl)piperidin-4-yl]phthalazin-1-amine This compound is obtained according to the procedure described in 1.4. by reacting 4-benzyl-1-chloro-7-methoxyphthalazine with 4-amino-1-(naphthalen-2-yl-methyl)piperidine.

EXAMPLE 18

Compound 22

4-Benzyl-5,7-dimethoxy-N-[1-(naphthalen-2-ylmethyl)piperidin-4-yl]phthalazin-1-amine 17.1. 3,5-dimethoxy-2-(phenylacetyl)benzoic acid This compound is synthesized by reacting methyl 3,5-dimethoxybenzoate with phenylacetyl chloride via the Friedel-Crafts reaction, followed by saponification of the ester obtained, according to the method described in 2.1. It is used in crude form in the following reaction.

18.2. 4-Benzyl-5,7-dimethoxy-2H-phthalazin-1-one

This compound is obtained according to the procedure described in 1.2. by reacting unpurified 3,5-dimethoxy-2-(phenylacetyl)benzoic acid with hydrazine hydrate.
LC/MS: MH⁺=297 (Rt=7.98 minutes)
¹H NMR δ in ppm (DMSO d 6): 3.75 (s, 3H); 3.90 (s, 3H); 4.30 (s, 2H); 6.89 (d, J=2.4 Hz, 1H); 7.12-7.16 (m, 3H); 7.20-7.30 (m, 3H); 12.51 (s, 1H, NH).

18.3. 4-Benzyl-1-chloro-5,7-dimethoxyphthalazine

This compound is obtained according to the procedure described in 1.3. by reacting 4-benzyl-5,7-dimethoxy-2H-phthalazin-1-one with phosphoryl chloride.
¹H NMR δ in ppm (DMSO d 6): 3.88 (s, 3H); 4.0 (s, 3H); 4.71 (s, 2H); 7.03-7.28 (m, 7H).

18.4. 4-Benzyl-5,7-dimethoxy-N-[1-(naphthalen-2-ylmethyl)piperidin-4-yl]phthalazin-1-amine This compound is obtained according to the procedure described in 1.4. by reacting 4-benzyl-1-chloro-5,7-dimethoxyphthalazine with 4-amino-1-(naphthalen-2-ylmethyl)piperidine.

EXAMPLE 19

Compound 23

5,7-Dimethoxy-4-ethyl-N-[1-(naphthalen-2-ylmethyl)piperidin-4-yl]phthalazin-1-amine 19.1. 3,5-dimethoxy-2-propionylbenzoic acid This compound is synthesized by reacting methyl 3,5-dimethoxybenzoate with propionyl chloride via the Friedel-Crafts reaction, followed by saponification of the ester obtained, according to the method described in 2.1. It is used in crude form in the following reaction.

19.2. 5,7-Dimethoxy-4-ethyl-2H-phthalazin-1-one

This compound is obtained according to the procedure described in 1.2. by reacting unpurified 3,5-dimethoxy-2-propionylbenzoic acid with hydrazine hydrate.
¹H NMR δ in ppm (DMSO d 6): 1.15 (t, J=7.2 Hz, 3H); 2.99 (q, J=7.2 Hz, 2H); 3.92 (s, 3H); 3.94 (s, 3H); 6.99 (d, J=2.7 Hz, 1H); 7.3 (d, J=2.7 Hz, 1H); 12.35 (s, 1H, NH).

19.3. 1-Chloro-5,7-dimethoxy-4-ethylphthalazine

This compound is obtained according to the procedure described in 1.3. by reacting 5,7-dimethoxy-4-ethyl-2H-phthalazin-1-one with phosphoryl chloride.
¹H NMR δ in ppm (DMSO d 6): 1.26 (t, J=7.2 Hz, 3H); 3.34 (q, J=7.2 Hz, 2H); 4.0 (s, 3H); 4.03 (s, 3H); 7.12 (d, J=2.4 Hz, 1H); 7.15 (d, J=2.4 Hz, 1H).

19.4. 5,7-dimethoxy-4-ethyl-N-[1-(naphthalen-2-ylmethyl)piperidin-4-yl]phthalazin-1-amine This compound is obtained according to the procedure described in 1.4. by reacting 1-chloro-5,7-dimethoxy-4-ethylphthalazine with 4-amino-1-(naphthalen-2-yl-methyl)piperidine.

EXAMPLE 20

Compound 24

7-methoxy-4-methoxymethyl-N-[1-(naphthalen-2-ylmethyl)piperidin-4-yl]phthalazin-1-amine hydrochloride

20.1. 5-methoxy-2-(methoxyacetyl)benzoic acid

This compound is synthesized according to the method described in 3.2. by reacting 2-bromo-5-methoxybenzoic acid pretreated with n-butyllithium with 2,N-dimethoxy-N-methylacetamide. It is used in crude form in the following reaction.

20.2. 7-Methoxy-4-methoxymethyl-2H-phthalazin-1-one

This compound is obtained according to the procedure described in 1.2. by reacting unpurified 5-methoxy-2-(methoxyacetyl)benzoic acid with hydrazine hydrate.
m.p.=184° C. (Mettler FP62)
LC/MS: MH$^+$=221 (Rt=5.33 minutes)
$^1$H NMR δ in ppm (DMSO d 6): 3.33 (s, 3H); 3.96 (s, 3H); 4.62 (s, 2H); 7.53 (dd, J$_1$=8.8 Hz, J$_2$=2.7 Hz, 1H); 7.66 (d, J=2.7 Hz, 1H); 8.0 (d, J=8.8 Hz, 1H); 12.61 (s, 1H, NH).

20.3. 1-Chloro-7-methoxy-4-methoxymethylphthalazine

This compound is obtained according to the procedure described in 1.3. by reacting 7-methoxy-4-methoxymethyl-2H-phthalazin-1-one with phosphoryl chloride.
$^1$H NMR δ in ppm (DMSO d 6): 3.33 (s, 3H); 4.06 (s, 3H); 5.02 (s, 2H); 7.56 (d, J=2.7 Hz, 1H); 7.77 (dd, J$_1$=9.2 Hz, J$_2$=2.7 Hz, 1H); 8.35 (d, J=9.2 Hz, 1H).

20.4. 7-methoxy-4-methoxymethyl-N-[1-(naphthalen-2-ylmethyl)piperidin-4-yl]phthalazin-1-amine hydrochloride This compound is obtained according to the procedure described in 1.4. by reacting 1-chloro-7-methoxy-4-methoxymethylphthalazine with 4-amino-1-(naphthalen-2-ylmethyl)piperidine. The hydrochloride is obtained after treatment with a solution of hydrogen chloride in isopropanol.

EXAMPLE 21

Compound 33

4-Cyclopropyl-7-methoxy-N-[1-(naphthalen-2-ylmethyl)piperidin-4-yl]phthalazin-1-amine

21.1. 2-cyclopropanecarbonyl-5-methoxybenzoic acid

This compound is synthesized according to the method described in 3.2. by reacting 2-bromo-5-methoxybenzoic acid pretreated with n-butyllithium with cyclopropyl-N-methoxy-N-methylcarboxamide. A yellow powder is obtained by precipitation in isopropyl ether.
m.p.=117° C. (Mettler FP62)
$^1$H NMR δ in ppm (DMSO d 6): 0.97-1.07 (m, 4H); 2.35-2.50 (m, 1H); 3.87 (s, 3H); 7.15-7.20 (m, 2H); 7.71 (dd, J$_1$=8.8 Hz, J$_2$=2.5 Hz, 1H) (COOH signal not visible).

21.2. 4-Cyclopropyl-7-methoxy-2H-phthalazin-1-one

This compound is obtained according to the procedure described in 1.2. by reacting 2-cyclopropanecarbonyl-5-methoxybenzoic acid with hydrazine hydrate.
m.p.=189° C. (Mettler FP62)
$^1$H NMR δ in ppm (DMSO d 6): 0.85-1.02 (m, 4H); 2.38-2.45 (m, 1H); 3.96 (s, 3H); 7.53 (dd, J$_1$=9 Hz, J$_2$=2.7 Hz, 1H); 7.66 (d, J=2.7 Hz, 1H); 8.22 (d, J=9 Hz, 1H); 12.31 (s, 1H, NH).

21.3. 1-Chloro-4-cyclopropyl-7-methoxyphthalazine

This compound is obtained according to the procedure described in 1.3. by reacting 4-cyclopropyl-7-methoxy-2H-phthalazin-1-one with phosphoryl chloride.
LC/MS: MH$^+$=235 (Rt=7.67 minutes)
$^1$H NMR δ in ppm (DMSO d 6): 1.13-1.26 (m, 4H); 2.80-2.95 (m, 1H); 4.05 (s, 3H); 7.51 (d, J=2.5 Hz, 1H); 7.76 (dd, J$_1$=9.2 Hz, J$_2$=2.5 Hz, 1H); 8.57 (d, J=9 Hz, 1H).

21.4. 4-Cyclopropyl-7-methoxy-N-[1-(naphthalen-2-ylmethyl)piperidin-4-yl]phthalazin-1-amine This compound is obtained according to the procedure described in 1.4. by reacting 1-chloro-4-cyclopropyl-7-methoxyphthalazine with 4-amino-1-(naphthalen-2-ylmethyl)piperidine.

EXAMPLE 22

Compound 42

4-(1,3-Benzodioxol-5-yl)-7-methoxy-N-[1-(naphthalen-2-ylmethyl)piperidin-4-yl]phthalazin-1-amine dihydrochloride

22.1. 2-(1,3-Benzodioxol-5-yl)carbonyl-5-methoxybenzoic acid

This compound is obtained according to the procedure described in 1.1. by reacting 1,3-benzodioxole-5-carboxylic acid and 2-bromo-5-methoxybenzoic acid after halogen-lithium exchange. It is used in crude form in the following reaction.

22.2. 4-(1,3-Benzodioxol-5-yl)-7-methoxy-2H-phthalazin-1-one

This compound is obtained according to the procedure described in 1.2. by reacting 2-(1,3-benzodioxol-5-yl)carbonyl-5-methoxybenzoic acid unpurified with hydrazine hydrate.
m.p.=271° C. (Mettler FP62)
LC/MS: MH$^+$=297 (Rt=6.83 minutes)
$^1$H NMR δ in ppm (DMSO d 6): 3.95 (s, 3H); 6.12 (s, 2H); 7.01-7.12 (m, 3H); 7.46 (dd, J$_1$=9 Hz, J$_2$=2.7 Hz, 1H); 7.66 (d, J=9 Hz, 1H); 7.71 (d, J=2.7 Hz, 1H); 12.69 (s, 1H, NH).

22.3. 4-(1,3-Benzodioxol-5-yl)-1-chloro-7-methoxyphthalazine

This compound is obtained according to the procedure described in 1.3. by reacting 4-(1,3-benzodioxol-5-yl)-7-methoxy-2H-phthalazin-1-one with phosphoryl chloride.
m.p.=178° C. (Mettler FP62)
LC/MS: MH$^+$=315 (Rt=7.81 minutes)

¹H NMR δ in ppm (DMSO d 6): 4.05 (s, 3H); 6.17 (s, 2H); 7.12-7.20 (m, 2H); 7.27 (d, J=1.5 Hz, 1H); 7.58 (d, J=2.7 Hz, 1H); 7.70 (dd, J₁=9.3 Hz, J₂=2.7 Hz, 1H); 8.01 (d, J=9.3 Hz, 1H).

22.4. 4-(1,3-Benzodioxol-5-yl)-7-methoxy-N-[1-(naphthalen-2-ylmethyl)piperidin-4-yl]phthalazin-1-amine dihydrochloride This compound is obtained according to the procedure described in 1.4. by reacting 4-(1,3-benzodioxol-5-yl)-1-chloro-7-methoxyphthalazine with 4-amino-1-(naphthalen-2-ylmethyl)piperidine. By treatment with a solution of hydrogen chloride in diethyl ether, a precipitate forms, which is filtered off, washed with diethyl ether and dried under reduced pressure. The hydrochloride obtained is in the form of a white solid.

EXAMPLE 23

Compound 43

4-(4-Chlorophenyl)-7-methoxy-N-[1-(naphthalen-2-ylmethyl)piperidin-4-yl]phthalazin-1-amine

23.1. 2-(4-chlorobenzoyl)-5-methoxybenzoic acid

This compound is synthesized according to the method described in 3.2. by reacting 2-bromo-5-methoxybenzoic acid pretreated with n-butyllithium with 4-chloro-N-methoxy-N-methylbenzamide. It is used in crude form in the following reaction.

23.2. 4-(4-Chlorophenyl)-7-methoxy-2H-phthalazin-1-one

This compound is obtained according to the procedure described in 1.2. by reacting 2-(4-chlorobenzoyl)-5-methoxybenzoic acid unpurified with hydrazine hydrate.
m.p.=274° C. (Mettler FP62)
LC/MS: MH⁺=287 (Rt=7.20 minutes)
¹H NMR δ in ppm (DMSO d 6): 3.97 (s, 3H); 7.48 (dd, J₁=8.5 Hz, J₂=2.5 Hz, 1H); 7.61-7.65 (m, 5H); 7.74 (d, J=2.5 Hz, 1H); 12.82 (s, 1H, NH).

23.3. 1-Chloro-4-(4-chlorophenyl)-7-methoxyphthalazine

This compound is obtained according to the procedure described in 1.3. by reacting 4-(4-chlorophenyl)-7-methoxy-2H-phthalazin-1-one with phosphoryl chloride.
m.p.=199° C. (Mettler FP62)
LC/MS: MH⁺=305 (Rt=8.05 minutes)
¹H NMR δ in ppm (DMSO d 6): 4.07 (s, 3H); 7.62 (d, J=2.5 Hz, 1H); 7.67-7.77 (m, 5H); 7.96 (d, J=9 Hz, 1H).

23.4. 4-(4-Chlorophenyl)-7-methoxy-N-[1-(naphthalen-2-ylmethyl)piperidin-4-yl]phthalazin-1-amine This compound is obtained according to the procedure described in 1.4. by reacting 1-chloro-4-(4-chlorophenyl)-7-methoxyphthalazine with 4-amino-1-(naphthalen-2-ylmethyl)piperidine.

EXAMPLE 24

Compound 45

7-Methoxy-4)-N-[1-(naphthalen-2-ylmethyl)piperidin-4-yl]-(4-trifluoromethyl-phenylphthalazin-1-amine

24.1. 5-methoxy-2-(4-trifluoromethylbenzoyl)benzoic acid

This compound is synthesized according to the method described in 3.2. by reacting 2-bromo-5-methoxybenzoic acid pretreated with n-butyllithium with N-methoxy-N-methyl-4-trifluoromethylbenzamide. It is used in crude form in the following reaction.

24.2. 7-Methoxy-4-(4-trifluoromethylphenyl)-2H-phthalazin-1-one

This compound is obtained according to the procedure described in 1.2. by reacting 5-methoxy-2-(4-trifluoromethylbenzoyl)benzoic acid unpurified with hydrazine hydrate.
m.p.=264° C. (Köfler)
LC/MS: MH⁺=321 (Rt=8.14 minutes)
¹H NMR δ in ppm (DMSO d 6): 3.96 (s, 3H); 7.46 (dd, J₁=9 Hz, J₂=2.7 Hz, 1H); 7.62 (d, J=9 Hz, 1H); 7.74 (d, J=2.7 Hz, 1H); 7.82 (d, J=8.2, 2H); 7.92 (d, J=8.2, 2H); 12.87 (s, 1H, NH).

24.3. 1-Chloro-7-methoxy-4-(4-trifluoromethylphenyl)phthalazine

This compound is obtained according to the procedure described in 1.3. by reacting 7-methoxy-4-(4-trifluoromethylphenyl)-2H-phthalazin-1-one with phosphoryl chloride.
LC/MS: MH⁺=338 (Rt=8.68 minutes)
¹H NMR δ in ppm (DMSO d 6): 4.07 (s, 3H); 7.63 (d, J=2.5 Hz, 1H); 7.71 (dd, J₁=9 Hz, J₂=2.5 Hz, 1H); 7.91-8.01 (m, 5H).

24.4. 7-Methoxy-4)-N-[1-(naphthalen-2-ylmethyl)piperidin-4-yl]-(4-trifluoro-methylphenylphthalazin-1-amine This compound is obtained according to the procedure described in 1.4. by reacting 1-chloro-7-methoxy-4-(4-trifluoromethylphenyl)phthalazine with 4-amino-1-(naphthalen-2-ylmethyl)piperidine.

EXAMPLE 25

Compound 51

4-cyclopentyl-7-methoxy-N-[1-(naphthalen-2-ylmethyl)piperidin-4-yl]phthalazin-1-amine dihydrochloride

25.1. 2-cyclopentanecarbonyl-5-methoxybenzoic acid

This compound is synthesized according to the method described in 3.2. by reacting 2-bromo-5-methoxybenzoic acid pretreated with n-butyllithium with cyclopentyl-N-methoxy-N-methylcarboxamide. It is used in crude form in the following reaction.

25.2. 4-Cyclopentyl-7-methoxy-2H-phthalazin-1-one

This compound is obtained according to the procedure described in 1.2. by reacting unpurified 2-cyclopentanecarbonyl-5-methoxybenzoic acid with hydrazine hydrate.
m.p.=232° C. (Mettler FP62)
$^1$H NMR δ in ppm (DMSO d 6): 1.65-1.95 (m, 6H); 1.95-2.10 (m, 2H); 3.55-3.70 (m, 1H); 3.95 (s, 3H); 7.50 (dd, $J_1$=9 Hz, $J_2$=2.7 Hz, 1H); 7.67 (d, J=2.7 Hz, 1H); 8.03 (d, J=9 Hz, 1H); 12.37 (s, 1H, NH).

25.3. 1-Chloro-4-cyclopentyl-7-methoxyphthalazine

This compound is obtained according to the procedure described in 1.3. by reacting 4-cyclopentyl-7-methoxy-2H-phthalazin-1-one with phosphoryl chloride. The product is too impure for a description by NMR. It is used as obtained in the following amination reaction.
LC/MS: MH$^+$=263 (Rt=9.04 minutes)

25.4. 4-cyclopentyl-7-methoxy-N-[1-(naphthalen-2-ylmethyl)piperidin-4-yl]phthalazin-1-amine dihydrochloride This compound is obtained according to the procedure described in 1.4. by reacting impure 1-chloro-4-cyclopentyl-7-methoxyphthalazine with 4-amino-1-(naphthalen-2-ylmethyl)piperidine. The dihydrochloride is obtained after treatment with a solution of hydrogen chloride in isopropanol, followed by crystallization from diisopropyl ether.

EXAMPLE 26

Compound 66

7-Methoxy-4-(4-methylphenyl)-N-[(-(naphthalen-2-ylmethyl)piperidin-4-yl]phthalazin-1-amine

26.1. 5-methoxy-2-(4-methylbenzoyl)benzoic acid

This compound is synthesized according to the method described in 3.2. by reacting 2-bromo-5-methoxybenzoic acid pretreated with n-butyllithium with N-methoxy-N-methyl-4-methylbenzamide. It is used in crude form in the following reaction.

26.2. 7-Methoxy-4-(4-methylphenyl)-2H-phthalazin-1-one

This compound is obtained according to the procedure described in 1.2. by reacting unpurified 5-methoxy-2-(4-methylbenzoyl)benzoic acid with hydrazine hydrate.
m.p.=223° C. (Mettler FP62)
LC/MS: MH$^+$=267 (Rt=8.07 minutes)
$^1$H NMR δ in ppm (DMSO d 6): 2.40 (s, 3H); 3.95 (s, 3H); 7.35 (d, J=7.8 Hz, 2H); 7.44-7.48 (m, 3H); 7.63 (d, J=9 Hz, 1H); 7.72 (d, J=2.7 Hz, 1H); 12.71 (s, 1H, NH).

26.3. 1-Chloro-7-methoxy-4-(4-methylphenyl)phthalazine

This compound is obtained according to the procedure described in 1.3. by reacting 7-methoxy-4-(4-methylphenyl)-2H-phthalazin-1-one with phosphoryl chloride.
m.p.=183° C. (Mettler FP62)
LC/MS: MH$^+$=285 (Rt=7.76 minutes)
$^1$H NMR δ in ppm (DMSO d 6): 2.46 (s, 3H); 4.06 (s, 3H); 7.43 (d, J=8.5 Hz, 2H); 7.58-7.63 (m, 3H); 7.70 (dd, $J_1$=9 Hz, $J_2$=2.5 Hz, 1H); 7.97 (d, J=9 Hz, 1H).

26.4. 7-Methoxy-4-(4-methylphenyl)-N-[1-(naphthalen-2-ylmethyl)piperidin-4-yl]phthalazin-1-amine This compound is obtained according to the procedure described in 1.4. by reacting 1-chloro-7-methoxy-4-(4-methylphenyl)phthalazine with 4-amino-1-(naphthalen-2-ylmethyl)piperidine.

EXAMPLE 27

Compound 67

4-Butyl-7-methoxy-N-[1-(naphthalen-2-ylmethyl)piperidin-4-yl]phthalazin-1-amine

27.1. 5-methoxy-2-pentanoylbenzoic acid

This compound is synthesized according to the method described in 3.2. by reacting 2-bromo-5-methoxybenzoic acid pretreated with n-butyllithium with butyl-N-methoxy-N-methylcarboxamide. It is used in crude form in the following reaction.

27.2. 4-Butyl-7-methoxy-2H-phthalazin-1-one

This compound is obtained according to the procedure described in 1.2. by reacting unpurified 5-methoxy-2-pentanoylbenzoic acid with hydrazine hydrate.
m.p.=175° C. (Mettler FP62)
LC/MS: MH$^+$=233 (Rt=7.75 minutes)
$^1$H NMR δ in ppm (DMSO d 6): 0.92 (t, J=7.3 Hz, 3H); 1.32-1.47 (m, 2H); 1.59-1.72 (m, 2H); 2.85-2.92 (m, 2H); 3.94 (s, 3H); 7.49 (dd, $J_1$=9 Hz, $J_2$=2.7 Hz, 1H); 7.66 (d, J=2.7 Hz, 1H); 7.93 (d, J=9 Hz, 1H); 12.37 (s, 1H, NH).

27.3. 4-Butyl-1-chloro-7-methoxyphthalazine

This compound is obtained according to the procedure described in 1.3. by reacting 4-butyl-7-methoxy-2H-phthalazin-1-one with phosphoryl chloride.
LC/MS: MH$^+$=251 (Rt=7.10 minutes)
$^1$H NMR δ in ppm (DMSO d 6): 0.94 (t, J=7.3 Hz, 3H); 1.35-1.50 (m, 2H); 1.70-1.82 (m, 2H); 3.24-3.32 (m, 2H); 4.04 (s, 3H); 7.51 (d, J=2.5 Hz, 1H); 7.72 (dd, $J_1$=9 Hz, $J_2$=2.5 Hz, 1H); 8.31 (d, J=9 Hz, 1H).

27.4. 4-Butyl-7-methoxy-N-[1-(naphthalen-2-ylmethyl)piperidin-4-yl]phthalazin-1-amine This compound is obtained according to the procedure described in 1.4. by reacting 4-butyl-1-chloro-7-methoxyphthalazine with 4-amino-1-(naphthalen-2-ylmethyl)piperidine.

EXAMPLE 28

Compound 71

4-Cyclopropylmethyl-7-methoxy-N-[1-(naphthalen-2-ylmethyl)piperidin-4-yl]phthalazin-1-amine

28.1. 2-(2-cyclopropylacetyl)-5-methoxybenzoic acid

This compound is synthesized according to the method described in 3.2. by reacting 2-bromo-5-methoxybenzoic acid pretreated with n-butyllithium with 2-cyclopropyl-N-methoxy-N-methylacetamide. It is used in crude form in the following reaction.

28.2. 4-Cyclopropylmethyl-7-methoxy-2H-phthalazin-1-one

This compound is obtained according to the procedure described in 1.2. by reacting unpurified 2-(2-cyclopropylacetyl)-5-methoxybenzoic acid with hydrazine hydrate.
$^1$H NMR δ in ppm (DMSO d 6): 0.23-0.28 (m, 2H); 0.46-0.52 (m, 2H); 1.09-1.13 (m, 1H); 2.83 (d, J=6.7 Hz, 2H); 3.96 (s, 3H); 7.52 (dd, J$_1$=8.7 Hz, J$_2$=2.7 Hz, 1H); 7.68 (d, J=2.7 Hz, 1H); 7.99 (d, J=8.7 Hz, 1H); 12.41 (s, 1H, NH).

28.3. 1-Chloro-4-cyclopropylmethyl-7-methoxyphthalazine

This compound is obtained according to the procedure described in 1.3. by reacting 4-cyclopropylmethyl-7-methoxy-2H-phthalazin-1-one with phosphoryl chloride.
LC/MS: MH$^+$=249 (Rt=6.91 minutes)

28.4. 4-Cyclopropylmethyl-7-methoxy-N-[1-(naphthalen-2-ylmethyl)piperidin-4-yl]phthalazin-1-amine This compound is obtained according to the procedure described in 1.4. by reacting 1-chloro-4-cyclopropylmethyl-7-methoxyphthalazine with 4-amino-1-(naphthalen-2-ylmethyl)piperidine.
LC/MS: MH$^+$=453 (Rt=5.45 minutes)
$^1$H NMR δ in ppm (DMSO d 6): 0.23-0.26 (m, 2H); 0.43-0.47 (m, 2H); 1.08-1.16 (m, 1H); 1.60-1.80 (m, 2H); 2.03-2.30 (m, 4H); 2.90-3.0 (m, 2H); 2.95 (d, J=6.6 Hz, 2H); 3.74 (s, 2H); 3.96 (s, 3H); 4.15-4.25 (m, 1H); 6.88 (d, J=7 Hz, 1H, NH); 7.42-7.58 (m, 4H); 7.73 (d, J=2.5 Hz, 1H); 7.83-7.94 (m, 4H); 8.03 (d, J=9 Hz, 1H).

EXAMPLE 29

Compound 82

4-(4-Fluorophenyl)-7-methoxy-N-[1-(naphthalen-2-ylmethyl)piperidin-4-yl]phthalazin-1-amine

29.1. 2-(4-fluorobenzoyl)-5-methoxybenzoic acid

This compound is synthesized according to the method described in 3.2. by reacting 2-bromo-5-methoxybenzoic acid pretreated with n-butyllithium with 4-fluoro-N-methoxy-N-methylbenzamide. It is used in crude form in the following reaction.

29.2. 4-(4-Fluorophenyl)-7-methoxy-2H-phthalazin-1-one

This compound is obtained according to the procedure described in 1.2. by reacting unpurified 2-(4-fluorobenzoyl)-5-methoxybenzoic acid with hydrazine hydrate.
m.p.=256° C. (Mettler FP62)
LC/MS: MH$^+$=271 (Rt=6.51 minutes)
$^1$H NMR δ in ppm (DMSO d 6): 3.97 (s, 3H); 7.35-7.43 (m, 2H), 7.48 (dd, J$_1$=9 Hz, J$_2$=2.7 Hz, 1H); 7.59-7.67 (m, 3H); 7.74 (d, J=2.7 Hz, 1H); 12.80 (s, 1H, NH).

29.3. 1-Chloro-4-(4-fluorophenyl)-7-methoxyphthalazine

This compound is obtained according to the procedure described in 1.3. by reacting 4-(4-fluorophenyl)-7-methoxy-2H-phthalazin-1-one with phosphoryl chloride.

LC/MS: MH$^+$=289 (Rt=8.58 minutes)
$^1$H NMR δ in ppm (DMSO d 6): 4.06 (s, 3H); 7.42-7.51 (m, 2H), 7.60 (d, J=2.5 Hz, 1H); 7.69-7.80 (m, 3H); 7.95 (d, J=9 Hz, 1H).

29.4. 4-(4-Fluorophenyl)-7-methoxy-N-[1-(naphthalen-2-ylmethyl)piperidin-4-yl]phthalazin-1-amine This compound is obtained according to the procedure described in 1.4. by reacting 1-chloro-4-(4-fluorophenyl)-7-methoxyphthalazine with 4-amino-1-(naphthalen-2-ylmethyl)piperidine.

EXAMPLE 30

Compound 88

7-Methoxy-4-(4-methoxymethylphenyl)-N-[1-(naphthalen-2-ylmethyl)piperidin-4-yl]phthalazin-1-amine

30.1. 5-methoxy-2-(4-methoxymethylbenzoyl)benzoic acid

This compound is synthesized according to the method described in 3.2. by reacting 2-bromo-5-methoxybenzoic acid pretreated with n-butyllithium with N-methoxy-4-methoxymethyl-N-methylbenzamide. The product is crystallized from diisopropyl ether.
LC/MS: MH$^+$=301 (Rt=6.60 minutes)
$^1$H NMR δ in ppm (DMSO d 6): 3.32 (s, 3H); 3.89 (s, 3H); 4.49 (s, 2H); 7.26 (dd, J$_1$=8.5 Hz, J$_2$=2.5 Hz, 1H); 7.40-7.45 (m, 4H); 7.63 (d, J=8.2 Hz, 2H); 13.1 (s, 1H, COOH).

30.2. 7-Methoxy-4-(4-methoxymethylphenyl)-2H-phthalazin-1-one

This compound is obtained according to the procedure described in 1.2. by reacting 5-methoxy-2-(4-methoxymethylbenzoyl)benzoic acid with hydrazine hydrate.
m.p.=201° C. (Mettler FP62)
LC/MS: MH$^+$=297 (Rt=6.54 minutes)
$^1$H NMR δ in ppm (DMSO d 6): 3.36 (s, 3H); 3.96 (s, 3H); 4.52 (s, 2H); 7.45-7.58 (m, 5H); 7.64 (d, J=9 Hz, 1H); 7.74 (d, J=2.7 Hz, 1H); 12.78 (s, 1H, NH).

30.3. 1-Chloro-7-methoxy-4-(4-methoxymethylphenyl)phthalazine

This compound is obtained according to the procedure described in 1.3. by reacting 7-methoxy-4-(4-methoxymethylphenyl)-2H-phthalazin-1-one with phosphoryl chloride.
LC/MS: MH$^+$=315 (Rt=8.26 minutes)
$^1$H NMR δ in ppm (DMSO d 6): 3.38 (s, 3H); 4.06 (s, 3H); 4.56 (s, 2H); 7.56 (d, J=8.4 Hz, 2H); 7.62 (d, J=2.7 Hz, 1H); 7.68-7.74 (m, 3H); 7.97 (d, J=9 Hz, 1H).

In this reaction, the predominant product is 1-chloro-4-(4-chloromethylphenyl)-7-methoxyphthalazine.
LC/MS: MH$^+$=319 (Rt=9.06 minutes) dichloro
$^1$H NMR δ in ppm (DMSO d 6): 4.06 (s, 3H); 4.90 (s, 2H); 7.61 (d, J=2.7 Hz, 1H); 7.71-7.75 (m, 5H); 7.95 (d, J=9 Hz, 1H).

30.4. 7-Methoxy-4-(4-methoxymethylphenyl)-N-[1-(naphthalen-2-ylmethyl)piperidin-4-yl]phthalazin-1-amine This compound is obtained according to the procedure described in 1.4. by reacting 1-chloro-7-methoxy-4-(4-methoxymethylphenyl)phthalazine with 4-amino-1-(naphthalen-2-ylmethyl)piperidine.

EXAMPLE 31

Compound 105

4-[(4-diethylaminomethyl)phenyl]-7-methoxy-N-[1-(naphthalen-2-ylmethyl)piperidin-4-yl]phthalazin-1-amine trihydrochloride

31.1. 1-Chloro-4-(4-diethylaminomethylphenyl)-7-methoxyphthalazine 280 mg (2 mmol) of potassium carbonate and 0.3 mL of diethylamine are added to a solution of 319 mg (1 mmol) of 1-chloro-4-(4-chloromethylphenyl)-7-methoxyphthalazine (synthesized in 30.3) in 3 mL of ethanol. The mixture is stirred at 85° C. for 4 hours. The ethanol is evaporated off and the residue is taken up in water and extracted with dichloromethane. The organic extracts are washed with brine, dried over anhydrous sodium sulfate and then evaporated under reduced pressure. The residue obtained is purified by chromatography on a column of silica gel (solvent: 95/5 to 85/15 (v/v) dichloromethane/methanol). 287 mg of product are obtained (80% yield).

LC/MS: MH$^+$=356 (Rt=5.38 minutes)

31.2. 4-(4-diethylaminomethylphenyl)-7-methoxy-N-[1-(naphthalen-2-ylmethyl)piperidin-4-yl]phthalazin-1-amine trihydrochloride This compound is obtained according to the procedure described in 1.4. by reacting 1-chloro-4-(4-diethylaminomethylphenyl)-7-methoxyphthalazine with 4-amino-1-(naphthalen-2-ylmethyl)piperidine. The trihydrochloride is obtained after treatment with a solution of hydrogen chloride in diethyl ether, concentration and then crystallization.

EXAMPLE 32

Compound 95

7-Methoxy-4-methyl-N-[1-(naphthalen-2-ylmethyl)piperidin-4-yl]phthalazin-1-amine

32.1. 2-acetyl-5-methoxybenzoic acid

This compound is synthesized according to the method described in 3.2. by reacting 2-bromo-5-methoxybenzoic acid pretreated with n-butyllithium with N-methoxy-N-methylacetamide. It is used in crude form in the following reaction.

32.2. 7-Methoxy-4-methyl-2H-phthalazin-1-one

This compound is obtained according to the procedure described in 1.2. by reacting unpurified 2-acetyl-5-methoxybenzoic acid with hydrazine hydrate.

m.p.=202° C. (Mettler FP62)
LC/MS: MH$^+$=191 (Rt=5.73 minutes)
$^1$H NMR δ in ppm (DMSO d 6): 2.50 (s, 3H); 3.96 (s, 3H); 7.52 (dd, J$_1$=8.8 Hz, J$_2$=2.7 Hz, 1H); 7.66 (d, J=2.7 Hz, 1H); 7.90 (d, J=8.8 Hz, 1H); 12.35 (s, 1H, NH).

32.3. 1-Chloro-7-methoxy-4-methylphthalazine

This compound is obtained according to the procedure described in 1.3. by reacting 7-methoxy-4-methyl-2H-phthalazin-1-one with phosphoryl chloride.

LC/MS: MH$^+$=209 (Rt=6.26 minutes)
$^1$H NMR δ in ppm (DMSO d 6): 2.92 (s, 3H); 4.06 (s, 3H); 7.54 (d, J=2.5 Hz, 1H); 7.77 (dd, J$_1$=9.2 Hz, J$_2$=2.5 Hz, 1H); 8.31 (d, J=9.2 Hz, 1H).

32.4. 7-Methoxy-4-methyl-N-[1-(naphthalen-2-ylmethyl)piperidin-4-yl]phthalazin-1-amine This compound is obtained according to the procedure described in 1.4. by reacting 1-chloro-7-methoxy-4-methylphthalazine with 4-amino-1-(naphthalen-2-yl-methyl)piperidine.

EXAMPLE 33

Compound 97

4-(2,5-dimethoxyphenyl)-7-methoxy-N-[1-(naphthalen-2-ylmethyl)piperidin-4-yl]phthalazin-1-amine dihydrochloride

33.1. 2-(2,5-dimethoxybenzoyl)-5-methoxybenzoic acid

This compound is synthesized according to the method described in 3.2. by reacting 2-bromo-5-methoxybenzoic acid pretreated with n-butyllithium with 2,5-dimethoxy-N-methoxy-N-methylbenzamide. It is crystallized from diisopropyl ether.

m.p.=122° C. (Mettler FP62)
LC/MS: MNa$^+$=339 (Rt=7.40 minutes)
$^1$H NMR δ in ppm (DMSO d 6): 3.50 (s, 3H); 3.73 (s, 3H); 3.86 (s, 3H); 7.02-7.14 (m, 4H); 7.22 (d, J=2.4 Hz, 1H); 7.29 (d, J=8.4 Hz, 1H); 12.96 (s, 1H, COOH).

33.2. 4-(2,5-Dimethoxyphenyl)-7-methoxy-2H-phthalazin-1-one

This compound is obtained according to the procedure described in 1.2. by reacting 2-(2,5-dimethoxybenzoyl)-5-methoxybenzoic acid with hydrazine hydrate.

m.p.=208° C. (Mettler FP62)
LC/MS: MH$^+$=313 (Rt=7.42 minutes)
$^1$H NMR δ in ppm (DMSO d 6): 3.62 (s, 3H); 3.74 (s, 3H); 3.94 (s, 3H); 6.91 (d, J=3 Hz, 1H); 7.05-7.15 (m, 2H); 7.22 (d, J=9 Hz, 1H); 7.40 (dd, J$_1$=9 Hz, J$_2$=2.7 Hz, 1H); 7.67 (d, J=2.7 Hz, 1H); 12.67 (s, 1H, NH).

33.3. 1-Chloro-4-(2,5-dimethoxyphenyl)-7-methoxyphthalazine

This compound is obtained according to the procedure described in 1.3. by reacting 4-(2,5-dimethoxyphenyl)-7-methoxy-2H-phthalazin-1-one with phosphoryl chloride.

m.p.=140° C. (Mettler FP62)
LC/MS: MH$^+$=331 (Rt=8.36 minutes)
$^1$H NMR δ in ppm (DMSO d 6): 3.61 (s, 3H); 3.77 (s, 3H); 4.05 (s, 3H); 7.0 (d, J=2.7 Hz, 1H); 7.13-7.21 (m, 2H); 7.55-7.59 (m, 2H); 7.65 (dd, J$_1$=9 Hz, J$_2$=2.7 Hz, 1H).

33.4. 4-(2,5-dimethoxyphenyl)-7-methoxy-N-[1-(naphthalen-2-ylmethyl)piperidin-4-yl]phthalazin-1-amine dihydrochloride This compound is obtained according to the procedure described in 1.4. by reacting 1-chloro-4-(2,5-dimethoxyphenyl)-7-methoxyphthalazine with 4-amino-1-(naphthalen-2-ylmethyl)piperidine. The dihydrochloride is obtained after treatment with a solution of hydrogen chloride in diethyl ether.

EXAMPLE 34

Compound 102

4-(2,4-dimethoxyphenyl)-7-methoxy-N-[1-(naphthalen-2-ylmethyl)piperidin-4-yl]phthalazin-1-amine dihydrochloride

34.1. 2-(2,4-dimethoxybenzoyl)-5-methoxybenzoic acid

This compound is synthesized according to the method described in 3.2. by reacting 2-bromo-5-methoxybenzoic acid pretreated with n-butyllithium with 2,4-dimethoxy-N-methoxy-N-methylbenzamide. It is used in crude form in the following reaction.

34.2. 4-(2,4-Dimethoxyphenyl)-7-methoxy-2H-phthalazin-1-one

This compound is obtained according to the procedure described in 1.2. by reacting 2-(2,4-dimethoxybenzoyl)-5-methoxybenzoic acid with hydrazine hydrate.

m.p.=256° C. (Mettler FP62)
LC/MS: MH$^+$=313 (Rt=7.49 minutes)
$^1$H NMR δ in ppm (DMSO d 6): 3.69 (s, 3H); 3.86 (s, 3H); 3.94 (s, 3H); 6.65-6.75 (m, 2H); 7.21-7.26 (m, 2H); 7.37-7.43 (m, 1H); 7.66-7.68 (m, 1H); 12.64 (s, 1H, NH).

34.3. 1-Chloro-4-(2,4-dimethoxyphenyl)-7-methoxyphthalazine

This compound is obtained according to the procedure described in 1.3. by reacting 4-(2,4-dimethoxyphenyl)-7-methoxy-2H-phthalazin-1-one with phosphoryl chloride.

m.p.=177° C. (Mettler FP62)
LC/MS: MH$^+$=331 (Rt=8.31 minutes)
NMR $^1H$ δ in ppm (DMSO d 6): 3.68 (s, 3H); 3.89 (s, 3H); 4.05 (s, 3H); 6.75 (dd, J$_1$=8.3 Hz, J$_2$=2.5 Hz, 1H, 6.80 (d, J=2.5 Hz, 1H); 7.35 (d, J=8.3 Hz, 1H); 7.54-7.64 (m, 3H).

34.4. 4-(2,4-dimethoxyphenyl)-7-methoxy-N-[1-(naphthalen-2-ylmethyl)piperidin-4-yl]phthalazin-1-amine dihydrochloride This compound is obtained according to the procedure described in 1.4. by reacting 1-chloro-4-(2,4-dimethoxyphenyl)-7-methoxyphthalazine with 4-amino-1-(naphthalen-2-ylmethyl)piperidine. The dihydrochloride is obtained after treatment with a solution of hydrogen chloride in diethyl ether.

EXAMPLE 35

Compound 103

4-(3,5-dimethoxyphenyl)-7-methoxy-N-[1-(naphthalen-2-ylmethyl)piperidin-4-yl]phthalazin-1-amine dihydrochloride

35.1. 2-(3,5-dimethoxybenzoyl)-5-methoxybenzoic acid

This compound is synthesized according to the method described in 3.2. by reacting 2-bromo-5-methoxybenzoic acid pretreated with n-butyllithium with 3,5-dimethoxy-N-methoxy-N-methylbenzamide. It is crystallized from diisopropyl ether.

m.p.=171° C. (Mettler FP62)
LC/MS: MH$^+$=317 (Rt=7.91 minutes)
$^1$H NMR δ in ppm (DMSO d 6): 3.76 (s, 6H); 3.89 (s, 3H); 6.71-6.77 (m, 3H); 7.25 (dd, J$_1$=8.5 Hz, J$_2$=2.5 Hz, 1H); 7.38-7.46 (m, 2H); 13.18 (s, 1H, COOH).

35.2. 4-(3,5-Dimethoxyphenyl)-7-methoxy-2H-phthalazin-1-one

This compound is obtained according to the procedure described in 1.2. by reacting 2-(3,5-dimethoxybenzoyl)-5-methoxybenzoic acid with hydrazine hydrate.

m.p.=237° C. (Mettler FP62)
LC/MS: MH$^+$=313 (Rt=7.74 minutes)
$^1$H NMR δ in ppm (DMSO d 6): 3.81 (s, 6H); 3.97 (s, 3H); 6.65-6.70 (m, 3H); 7.47 (dd, J$_1$=8.8 Hz, J$_2$=2.7 Hz, 1H); 7.68-7.74 (m, 2H); 12.74 (s, 1H, NH).

35.3. 1-Chloro-4-(3,5-dimethoxyphenyl)-7-methoxyphthalazine

This compound is obtained according to the procedure described in 1.3. by reacting 4-(3,5-dimethoxyphenyl)-7-methoxy-2H-phthalazin-1-one with phosphoryl chloride.

m.p.=189° C. (Mettler FP62)
LC/MS: MH$^+$=331 (Rt=8.73 minutes)
$^1$H NMR δ in ppm (DMSO d 6): 3.84 (s, 6H); 4.07 (s, 3H); 6.75 (m, 1H); 6.82 (m, 2H); 7.61 (d, J=2.5 Hz, 1H); 7.72 (dd, J$_1$=9 Hz, J$_2$=2.5 Hz, 1H); 8.02 (d, J=9 Hz, 1H).

35.4. 4-(3,5-dimethoxyphenyl)-7-methoxy-N-[1-(naphthalen-2-ylmethyl)piperidin-4-yl]phthalazin-1-amine dihydrochloride This compound is obtained according to the procedure described in 1.4. by reacting 1-chloro-4-(3,5-dimethoxyphenyl)-7-methoxyphthalazine with 4-amino-1-(naphthalen-2-ylmethyl)piperidine. The dihydrochloride is obtained after treatment with a solution of hydrogen chloride in diethyl ether.

EXAMPLE 36

Compound 104

7-methoxy-4-N-[1-(naphthalen-2-ylmethyl)piperidin-4-yl]-(2-phenylethyl)phthalazin-1-amine dihydrochloride

36.1. 5-methoxy-2-(2-phenylpropionyl)benzoic acid

This compound is synthesized according to the method described in 3.2. by reacting 2-bromo-5-methoxybenzoic acid pretreated with n-butyllithium with N-methoxy-N-methyl-2-phenylpropionamide. It is used in crude form in the following reaction.

36.2. 7-Methoxy-4-(2-phenylethyl)-2H-phthalazin-1-one

This compound is obtained according to the procedure described in 1.2. by reacting unpurified 5-methoxy-2-(2-phenylpropionyl)benzoic acid with hydrazine hydrate.

m.p.=189° C. (Mettler FP62)
LC/MS: MH$^+$=281 (Rt=6.62 minutes)

¹H NMR δ in ppm (DMSO d 6): 2.98-3.04 (m, 2H); 3.16-3.22 (m, 2H); 3.94 (s, 3H); 7.14-7.30 (m, 5H); 7.48 (dd, $J_1$=9 Hz, $J_2$=2.7 Hz, 1H); 7.66 (d, J=2.7 Hz, 1H); 7.99 (d, J=9 Hz, 1H); 12.40 (s, 1H, NH).

36.3. 1-Chloro-7-methoxy-4-(2-phenylethyl)phthalazine

This compound is obtained according to the procedure described in 1.3. by reacting 7-methoxy-4-(2-phenylethyl)-2H-phthalazin-1-one with phosphoryl chloride.

LC/MS: MH⁺=299 (Rt=8.94 minutes)

¹H NMR δ in ppm (DMSO d 6): 3.10-3.15 (m, 2H); 3.54-3.60 (m, 2H); 4.03 (s, 3H); 7.17-7.31 (m, 5H); 7.49 (d, J=2.5 Hz, 1H); 7.67 (dd, $J_1$=9 Hz, $J_2$=2.5 Hz, 1H); 8.31 (d, J=9 Hz, 1H).

36.4. 7-methoxy-4-N-[1-(naphthalen-2-ylmethyl)piperidin-4-yl]-(2-phenyl-ethyl)phthalazin-1-amine dihydrochloride This compound is obtained according to the procedure described in 1.4. by reacting 1-chloro-7-methoxy-4-(2-phenylethyl)phthalazine with 4-amino-1-(naphthalen-2-ylmethyl)piperidine. The dihydrochloride is obtained after treatment with a solution of hydrogen chloride in diethyl ether.

EXAMPLE 37

Compound 106

7-Fluoro-4-(4-fluorophenyl)-N-[1-(naphthalen-2-ylmethyl)piperidin-4-yl]phthalazin-1-amine

37.1. 7-Fluoro-4-(4-fluorophenyl)-2H-phthalazin-1-one

This compound is obtained according to the procedure described in 1.2. by reacting 5-fluoro-2-(4-fluorobenzoyl)benzoic acid with hydrazine hydrate.

m.p.=206° C. (Mettler FP62)
LC/MS: MH⁺=259 (Rt=7.64 minutes)

37.2. 1-Chloro-7-fluoro-4-(4-fluorophenyl)phthalazine

This compound is obtained according to the procedure described in 1.3. by reacting 7-fluoro-4-(4-fluorophenyl)-2H-phthalazin-1-one with phosphoryl chloride.

m.p.=195° C. (Mettler FP62)
LC/MS: MH⁺=277 (Rt=7.90 minutes)

¹H NMR δ in ppm (DMSO d 6): 7.45-7.52 (m, 2H), 7.78-7.84 (m, 2H); 8.03-8.19 (m, 3H).

37.3. 7-Fluoro-4-(4-fluorophenyl)-N-[1-(naphthalen-2-ylmethyl)piperidin-4-yl]phthalazin-1-amine This compound is obtained according to the procedure described in 1.4. by reacting 1-chloro-7-fluoro-4-(4-fluorophenyl)phthalazine with 4-amino-1-(naphthalen-2-ylmethyl)piperidine.

EXAMPLE 38

Compound 109

7-methoxy-N-[1-(naphthalen-2-ylmethyl)piperidin-4-yl]-4-(pyridin-3-yl)phthalazin-1-amine trihydrochloride

38.1. 5-methoxy-2-pyridin-3-ylbenzoic acid

This compound is synthesized according to the method described in 3.2. by reacting 2-bromo-5-methoxybenzoic acid pretreated with n-butyllithium with N-methoxy-N-methylnicotinamide. After precipitation in aqueous phase at pH 4, followed by filtration and drying, a beige-coloured powder is obtained.

m.p.=178° C. (Mettler FP62)
LC/MS: MH⁺=258 (Rt=5.59 minutes)

¹H NMR δ in ppm (DMSO d 6): 3.90 (s, 3H); 7.29 (dd, $J_1$=9 Hz, $J_2$=2.7 Hz, 1H); 7.43-7.56 (m, 3H); 7.97 (m, 1H); 8.73-8.77 (m, 2H); 13.31 (s, 1H, COOH).

38.2. 7-Methoxy-4-(pyridin-3-yl)-2H-phthalazin-1-one

This compound is obtained according to the procedure described in 1.2. by reacting 5-methoxy-2-pyridin-3-ylbenzoic acid with hydrazine hydrate.

m.p.=260° C. (Köfler)
LC/MS: MH⁺=254 (Rt=5.43 minutes)

¹H NMR δ in ppm (DMSO d 6): 3.97 (s, 3H); 7.49 (dd, $J_1$=9 Hz, $J_2$=2.7 Hz, 1H); 7.59-7.64 (m, 2H); 7.76 (d, J=2.7 Hz, 1H); 8.02-8.06 (m, 1H); 8.72-8.80 (m, 2H); 12.90 (s, 1H, NH).

38.3. 1-Chloro-7-methoxy-4-(pyridin-3-yl)phthalazine

This compound is obtained according to the procedure described in 1.3. by reacting 7-methoxy-4-(pyridin-3-yl)-2H-phthalazin-1-one with phosphoryl chloride.

m.p.=180° C. (Mettler FP62)
LC/MS: MH⁺=272 (Rt=6.26 minutes)

¹H NMR δ in ppm (DMSO d 6): 4.08 (s, 3H); 7.51-7.76 (m, 3H); 7.96 (d, J=9 Hz, 1H); 8.15-8.20 (m, 1H); 8.80-9.0 (m, 2H).

38.4. 7-methoxy-N-[1-(naphthalen-2-ylmethyl)piperidin-4-yl]-4-(pyridin-3-yl)phthalazin-1-amine trihydrochloride This compound is obtained according to the procedure described in 1.4. by reacting 1-chloro-7-methoxy-4-(pyridin-3-yl)phthalazine with 4-amino-1-(naphthalen-2-ylmethyl)piperidine. The trihydrochloride is obtained after treatment with a solution of hydrogen chloride in isopropyl alcohol.

EXAMPLE 39

Compound 111

4-(biphenyl-4-yl)-7-methoxy-N-[1-(naphthalen-2-ylmethyl)piperidin-4-yl]phthalazin-1-amine dihydrochloride

39.1. 2-(biphenyl-4-carbonyl)-5-methoxybenzoic acid

This compound is synthesized according to the method described in 3.2. by reacting 2-bromo-5-methoxybenzoic acid pretreated with n-butyllithium with 4-phenyl-N-methoxy-N-methylbenzamide.

m.p.=200° C. (Mettler FP62)
LC/MS: MH⁺=333 (Rt=9.16 minutes)

¹H NMR δ in ppm (DMSO d 6): 3.90 (s, 3H); 7.28 (dd, $J_1$=8.5 Hz, $J_2$=2.5 Hz, 1H); 7.41-7.54 (m, 5H); 7.69-7.82 (m, 6H); 13.2 (s, 1H, COOH).

39.2. 4-(Biphenyl-4-yl)-7-methoxy-2N-phthalazin-1-one

This compound is obtained according to the procedure described in 1.2. by reacting 2-(biphenyl-4-carbonyl)-5-methoxybenzoic acid with hydrazine hydrate.

LC/MS: MH$^+$=329 (Rt=9.31 minutes)

$^1$H NMR δ in ppm (DMSO d 6): 3.98 (s, 3H); 7.42-7.56 (m, 4H), 7.66-7.88 (m, 8H); 12.81 (s, 1H, NH).

39.3. 4-(Biphenyl-4-yl)-1-chloro-7-methoxyphthalazine

This compound is obtained according to the procedure described in 1.3. by reacting 4-(biphenyl-4-yl)-7-methoxy-2H-phthalazin-1-one with phosphoryl chloride.

m.p.=177° C. (Mettler FP62)

LC/MS: MH$^+$=347 (Rt=10.25 minutes)

$^1$H NMR δ in ppm (DMSO d 6): 4.08 (s, 3H); 7.44-7.58 (m, 3H), 7.63 (d, J=2.5 Hz, 1H); 7.73 (dd, J$_1$=9 Hz, J$_2$=2.5 Hz, 1H); 7.79-7.95 (m, 6H); 8.05 (d, J=9 Hz, 1H).

39.4. 7-methoxy-4-(4-phenylphenyl)-N-[1-(naphthalen-2-ylmethyl)piperidin-4-yl]phthalazin-1-amine dihydrochloride This compound is obtained according to the procedure described in 1.4. by reacting 4-(biphenyl-4-yl)-1-chloro-7-methoxyphthalazine with 4-amino-1-(naphthalen-2-ylmethyl)piperidine. The dihydrochloride is obtained after treatment with a solution of hydrogen chloride in diethyl ether.

EXAMPLE 40

Compound 117

4-(3,4-dimethylphenyl)-7-methoxy-N-[1-(naphthalen-2-ylmethyl)piperidin-4-yl]phthalazin-1-amine dihydrochloride

40.1. 2-(3,4-dimethylbenzoyl)-5-methoxybenzoic acid

This compound is synthesized according to the method described in 3.2. by reacting 2-bromo-5-methoxybenzoic acid pretreated with n-butyllithium with 3,4-dimethyl-N-methoxy-N-methylbenzamide.

m.p.=173° C. (Mettler FP62)

LC/MS: MH$^+$=285 (Rt=8.37 minutes)

$^1$H NMR δ in ppm (DMSO d 6): 2.24 (s, 3H); 2.28 (s, 3H); 3.88 (s, 3H); 7.18-7.55 (m, 6H); 13.07 (s, 1H, COOH).

40.2. 4-(3,4-Dimethylphenyl)-7-methoxy-2H-phthalazin-1-one

This compound is obtained according to the procedure described in 1.2. by reacting 2-(3,4-dimethylbenzoyl)-5-methoxybenzoic acid with hydrazine hydrate.

m.p.=241° C. (Mettler FP62)

LC/MS: MH$^+$=281 (Rt=8.54 minutes)

$^1$H NMR δ in ppm (DMSO d 6): 2.32 (s, 3H); 2.33 (s, 3H); 3.97 (s, 3H); 7.26-7.35 (m, 3H); 7.47 (dd, J$_1$=9 Hz, J$_2$=2.7 Hz, 1H); 7.66 (d, J=9 Hz, 1H); 7.74 (d, J=2.7 Hz, 1H); 12.73 (s, 1H, NH).

40.3. 1-Chloro-4-(3,4-dimethylphenyl)-7-methoxyphthalazine

This compound is obtained according to the procedure described in 1.3. by reacting 4-(3,4-dimethylphenyl)-7-methoxy-2H-phthalazin-1-one with phosphoryl chloride.

m.p.=204° C. (Mettler FP62)

LC/MS: MH$^+$=299 (Rt=9.47 minutes)

$^1$H NMR δ in ppm (DMSO d 6): 2.35 (s, 3H); 2.36 (s, 3H); 4.06 (s, 3H); 7.35-7.48 (m, 3H); 7.59 (d, J=2.5 Hz, 1H); 7.70 (dd, J=9 Hz, J$_2$=2.5 Hz, 1H); 7.98 (d, J=9 Hz, 1H).

40.4. 4-(3,4-dimethylphenyl)-7-methoxy-N-[1-(naphthalen-2-ylmethyl)piperidin-4-yl]phthalazin-1-amine dihydrochloride This compound is obtained according to the procedure described in 1.4. by reacting 1-chloro-4-(3,4-dimethylphenyl)-7-methoxyphthalazine with 4-amino-1-(naphthalen-2-ylmethyl)piperidine. The dihydrochloride is obtained after treatment with a solution of hydrogen chloride in isopropanol, followed by crystallization from ethyl acetate.

EXAMPLE 41

Compound 136

7-methoxy-4-phenoxymethyl-N-[1-(naphthalen-2-ylmethyl)piperidin-4-yl]phthalazin-1-amine dihydrochloride

41.1. 5-methoxy-2-(2-phenoxyacetyl)benzoic acid

This compound is synthesized according to the method described in 3.2. by reacting 2-bromo-5-methoxybenzoic acid pretreated with n-butyllithium with N-methoxy-N-methyl-2-phenoxyacetamide. The product is used in crude form in the following reaction.

41.2. 7-Methoxy-4-phenoxymethyl-2H-phthalazin-1-one

This compound is obtained according to the procedure described in 1.2. by reacting 5-methoxy-2-(2-phenoxyacetyl)benzoic acid with hydrazine hydrate.

m.p.=192° C. (Mettler FP62)

LC/MS: MH$^+$=283 (Rt=7.91 minutes)

$^1$H NMR δ in ppm (DMSO d 6): 3.96 (s, 3H); 5.31 (s, 2H); 6.96-7.10 (m, 3H); 7.29-7.36 (m, 2H); 7.55 (dd, J$_1$=9 Hz, J$_2$=2.7 Hz, 1H); 7.68 (d, J=2.7 Hz, 1H); 7.98 (d, J=9 Hz, 1H); 12.69 (s, 1H, NH).

41.3. 1-Chloro-7-methoxy-4-phenoxymethylphthalazine

This compound is obtained according to the procedure described in 1.3. by reacting 7-methoxy-4-phenoxymethyl-2H-phthalazin-1-one with phosphoryl chloride.

LC/MS: MH$^+$=301 (Rt=8.90 minutes)

$^1$H NMR δ in ppm (DMSO d 6): 4.06 (s, 3H); 5.73 (s, 2H); 6.96-7.03 (m, 1H); 7.09-7.13 (m, 2H); 7.29-7.36 (m, 2H); 7.58 (d, J=2.5 Hz, 1H); 7.81 (dd, J$_1$=9 Hz, J$_2$=2.5 Hz, 1H); 8.37 (d, J=9 Hz, 1H).

41.4. 7-methoxy-4-phenoxymethyl-N-[1-(naphthalen-2-ylmethyl)piperidin-4-yl]phthalazin-1-amine dihydrochloride This compound is obtained according to the procedure described in 1.4. by reacting 1-chloro-7-methoxy-4-phenoxymethylphthalazine with 4-amino-1-(naphthalen-2-ylmethyl)piperidine. The dihydrochloride is obtained after treatment with a solution of hydrogen chloride in diethyl ether, followed by crystallization from diisopropyl ether.

EXAMPLE 42

Compound 137

4,7-diphenyl-N-[1-(naphthalen-2-ylmethyl)piperidin-4-yl]-phthalazin-1-amine dihydrochloride

42.1. 7-Hydroxy-N-[1-(naphthalen-2-ylmethyl)piperidin-4-yl]-4-phenylphthalazin-1-amine A mixture of 597 mg (1.25 mmol) of 7-methoxy-N-[1-(naphthalen-2-ylmethyl)piperidin-4-yl]-4-phenylphthalazin-1-amine (compound 1) and pyridinium hydrochloride is heated at 210° C. for 45 minutes. The reaction medium is cooled and 1N sodium hydroxide solution is then added. A precipitate forms, which is washed with water and with dichloromethane, and then dried under reduced pressure. 500 mg of a beige-coloured powder are obtained.

LC/MS: MH$^+$=461 (Rt=5.30 minutes)

$^1$H NMR δ in ppm (DMSO d 6): 1.64-1.73 (m, 2H); 1.90-2.03 (m, 2H); 2.10-2.22 (m, 2H); 2.85-2.95 (m, 2H); 3.66 (s, 2H); 4.10-4.18 (m, 1H); 5.90-6.0 (m, 1H, OH); 6.60-6.64 (m, 2H); 7.20-7.24 (d,J=9.7 Hz, 1H, NH); 7.39-7.57 (m, 9H); 7.82-7.94 (m, 4H).

42.2. 1-[1-(naphthalen-2-ylmethyl)piperidin-4-yl-amino]-4-phenyl-7-trifluoromethanesulfonyloxyphthalazin-6-yl 558 mg (1.5 mmol) of N-phenyltrifluoromethanesulfonimide ((CF$_3$SO$_2$)$_2$NC$_6$H$_5$) and 0.17 mL of triethylamine are added to a solution of 480 mg (1.04 mmol) of 7-hydroxy-N-[1-(naphthalen-2-ylmethyl)piperidin-4-yl]-4-phenylphthalazin-1-amine in 6 mL of dichloromethane. The mixture is stirred at room temperature under argon for 2 days. It is hydrolysed with aqueous ammonium chloride solution and then extracted with dichloromethane. The organic phase is dried over anhydrous sodium sulfate, filtered and evaporated under reduced pressure. A brown oil is obtained, which is used as obtained in the following reaction.

42.3. 4,7-diphenyl-N-[1-(naphthalen-2-ylmethyl)piperidin-4-yl]-phthalazin-1-amine dihydrochloride 0.5 mL of aqueous 2N sodium carbonate solution, 70 mg (0.57 mmol) of phenylboronic acid and 18 mg of tetrakis palladium are added to a solution of 0.5 mmol of 1-[1-(naphthalen-2-ylmethyl)piperidin-4-yl-amino]-4-phenyl-7-trifluoromethanesulfonyloxyphthalazin-6-yl in 4 ml of toluene. The mixture is stirred at 100° C. for 6 hours in a stoppered tube under argon. 1N sodium hydroxide solution is added to the cooled reaction medium, and the mixture is extracted with ethyl acetate. The organic phase is dried over anhydrous sodium sulfate, filtered and evaporated under reduced pressure. After purification by column chromatography (100/0 to 90/10 (v/v) dichloromethane/methanol), 150 mg of product are obtained.

LC/MS: MH$^+$=521 (Rt=6.48 minutes)

$^1$H NMR δ in ppm (DMSO d 6): 1.70-1.90 (m, 2H); 2.08-2.30 (m, 4H); 2.90-3.05 (m, 2H); 3.72 (s, 2H); 4.30-4.40 (m, 1H); 7.40 (d, 1H, NH); 7.48-7.70 (m, 11H); 7.82-7.97 (m, 7H); 8.18 (d, J=9 Hz, 1H); 8.25 (s, 1H).

The dihydrochloride is obtained after treatment with a solution of hydrogen chloride in diethyl ether.

EXAMPLE 43

Compound 142

4-(4-methoxyphenyl)-6-methyl-N-[1-(naphthalen-2-ylmethyl)piperidin-4-yl]phthalazin-1-amine

43.1. 2-(4-methoxybenzoyl)-4-methylbenzoic acid

This compound is synthesized according to the method described in 3.2. by reacting 2-bromo-4-methylbenzoic acid pretreated with n-butyllithium with 4-methoxy-N-methoxy-N-methyl-4-benzamide. It is used in crude form in the following reaction.

43.2. 4-(4-Methoxyphenyl)-6-methyl-2H-phthalazin-1-one

This compound is obtained according to the procedure described in 1.2. by reacting unpurified 2-(4-methoxybenzoyl)-4-methylbenzoic acid with hydrazine hydrate.

m.p.=245° C. (Mettler FP62)

LC/MS: MH$^+$=267 (Rt=7.63 minutes)

$^1$H NMR δ in ppm (DMSO d 6): 2.33 (s, 3H); 3.86 (s, 3H); 7.10-7.13 (m, 2H); 7.48-7.55 (m, 3H); 7.70 (d, J=8 Hz, 1H); 8.24 (d, J=8 Hz, 1H); (NH not detected).

43.3. 1-Chloro-4-(4-methoxyphenyl)-6-methylphthalazine

This compound is obtained according to the procedure described in 1.3. by reacting 4-(4-methoxyphenyl)-6-methyl-2H-phthalazin-1-one with phosphoryl chloride.

LC/MS: MH$^+$=285 (Rt=8.70 minutes)

$^1$H NMR δ in ppm (DMSO d 6): 2.58 (s, 3H); 3.90 (s, 3H); 7.16-7.23 (m, 2H); 7.66-7.73 (m, 2H); 7.85 (d, J=1.5 Hz, 1H); 8.03 (dd, J$_1$=8.5 Hz, J$_2$=1.5 Hz, 1H); 8.28 (d, J=8.5 Hz, 1H).

43.4. 4-(4-methoxyphenyl)-6-methyl-N-[1-(naphthalen-2-ylmethyl)piperidin-4-yl]phthalazin-1-amine This compound is obtained according to the procedure described in 1.4. by reacting 1-chloro-4-(4-methoxyphenyl)-6-methylphthalazine with 4-amino-1-(naphthalen-2-ylmethyl)piperidine.

EXAMPLE 44

Compound 143

7-chloro-4-(4-methoxyphenyl)-N-[1-(naphthalen-2-ylmethyl)piperidin-4-yl]phthalazin-1-amine dihydrochloride

44.1. 5-chloro-2-(4-methoxybenzoyl)benzoic acid

This compound is synthesized according to the method described in 3.2. by reacting 2-bromo-5-chlorobenzoic acid pretreated with n-butyllithium with 4-methoxy-N-methoxy-N-methyl-benzamide. It is used in crude form in the following reaction.

44.2. 7-Chloro-4-(4-methoxyphenyl)-2H-phthalazin-1-one

This compound is obtained according to the procedure described in 1.2. by reacting unpurified 5-chloro-2-(4-methoxybenzoyl)benzoic acid with hydrazine hydrate.

m.p.=220° C. (Mettler FP62)
LC/MS: MH$^+$=286 (Rt=8.12 minutes)
$^1$H NMR δ in ppm (DMSO d 6): 3.86 (s, 3H); 7.09-7.15 (m, 2H); 7.50-7.57 (m, 2H); 7.74 (d, J=8.7 Hz, 1H); 7.96 (dd, J$_1$=8.7 Hz, J$_2$=2.2 Hz, 1H); 8.28 (d, J=2.2 Hz, 1H); 13.0 (s, 1H, NH).

44.3. 1,7-Dichloro-4-(4-methoxyphenyl)phthalazine

This compound is obtained according to the procedure described in 1.3. by reacting 7-chloro-4-(4-methoxyphenyl)-2H-phthalazin-1-one with phosphoryl chloride.

LC/MS: MH$^+$=305 (Rt=9.34 minutes)
$^1$H NMR δ in ppm (DMSO d 6): 3.90 (s, 3H); 7.17-7.23 (m, 2H); 7.68-7.74 (m, 2H); 8.10 (d, J=9 Hz, 1H); 8.17 (dd, J$_1$=9 Hz, J$_2$=2 Hz, 1H); 8.39 (d, J=2 Hz, 1H).

44.4. 7-chloro-4-(4-methoxyphenyl)-N-[1-(naphthalen-2-ylmethyl)piperidin-4-yl]phthalazin-1-amine dihydrochloride This compound is obtained according to the procedure described in 1.4. by reacting 1,7-dichloro-4-(4-methoxyphenyl)phthalazine with 4-amino-1-(naphthalen-2-ylmethyl)piperidine. The dihydrochloride is obtained after treatment with a solution of hydrogen chloride in diethyl ether, followed by crystallization from diisopropyl ether.

EXAMPLE 45

Compound 145

4-(4-bromophenyl)-7-methoxy-N-[1-(naphthalen-2-ylmethyl)piperidin-4-yl]phthalazin-1-amine dihydrochloride

45.1. 2-(4-Bromobenzoyl)-5-methoxybenzoic acid

This compound is synthesized according to the method described in 3.2. by reacting 2-bromo-5-methoxybenzoic acid pretreated with n-butyllithium with 4-bromo-N-methoxy-N-methylbenzamide. It is used in crude form in the following reaction.

45.2. 4-(4-Bromophenyl)-7-methoxy-2H-phthalazin-1-one

This compound is obtained according to the procedure described in 1.2. by reacting unpurified 2-(4-bromobenzoyl)-5-methoxybenzoic acid with hydrazine hydrate.

m.p.=275° C. (Mettler FP62)
LC/MS: MH$^+$=333 (Rt=8.47 minutes)
$^1$H NMR δ in ppm (DMSO d 6): 3.97 (s, 3H); 7.48 (dd, J$_1$=9 Hz, J$_2$=2.7 Hz, 1H); 7.52-7.58 (m, 2H); 7.64 (d, J=9 Hz, 1H); 7.74-7.79 (m, 3H); 12.83 (s, 1H, NH).

45.3. 4-(4-Bromophenyl)-1-chloro-7-methoxyphthalazine

This compound is obtained according to the procedure described in 1.3. by reacting 4-(4-bromophenyl)-7-methoxy-2H-phthalazin-1-one with phosphoryl chloride.

m.p.=205° C. (Mettler FP62)
LC/MS: MH$^+$=351 (Rt=9.38 minutes)
$^1$H NMR δ in ppm (DMSO d 6): 4.07 (s, 3H); 7.63 (d, J=2.5 Hz, 1H); 7.65-7.69 (m, 2H); 7.72 (dd, J$_1$=9 Hz, J$_2$=2.5 Hz, 1H); 7.81-7.87 (m, 2H); 7.96 (d, J=9 Hz, 1H).

45.4. 4-(4-Bromophenyl)-7-methoxy-N-[1-(naphthalen-2-ylmethyl)piperidin-4-yl]phthalazin-1-amine dihydrochloride This compound is obtained according to the procedure described in 1.4. by reacting 4-(4-bromophenyl)-1-chloro-7-methoxyphthalazine with 4-amino-1-(naphthalen-2-ylmethyl)piperidine. The dihydrochloride is obtained after treatment with a solution of hydrogen chloride in diethyl ether.

EXAMPLE 46

Compound 17

7-methoxy-N-[1-(naphthalen-2-ylmethyl)piperidin-4-yl]-5-phenylphthalazin-1-amine dihydrochloride

46.1. Methyl 2-formyl-3-hydroxy-5-methoxybenzoate

A solution of 5.1 g (0.3 mmol) of methyl 2-formyl-3,5-methoxybenzoate in 50 mL of dichloromethane is stirred at −10° C., followed by dropwise addition of 23 mL of a solution of boron tribromide in dichloromethane. The mixture is stirred at −10° C. for 1 hour and is then hydrolysed with 100 mL of water. The organic phase is washed with water, dried over anhydrous sodium sulfate, filtered and evaporated under reduced pressure. The residue is purified on a column of silica (eluent: 7/3 v/v cyclohexane/ethyl acetate). 4 g of a beige-coloured product are obtained.

$^1$H NMR δ in ppm (DMSO d 6): 3.83 (s, 3H); 3.86 (s, 3H); 6.66 (d, J=2.5 Hz, 1H); 6.73 (d, J=2.5 Hz, 1H); 10.20 (s, 1H, CHO); 11.8 (s, 1H, OH).

46.2. Methyl 2-formyl-5-methoxy-3-trifluoromethanesulfonyloxybenzoate

A solution of 1 g (4.7 mmol) of methyl 2-formyl-3-hydroxy-5-methoxybenzoate in 20 mL of tetrahydrofuran is stirred at room temperature under nitrogen, followed by addition of 200 mg of sodium hydride as a 60% suspension in oil. The mixture is stirred for 30 minutes and 1.7 g (4.8 mmol) of N-phenyltrifluoromethanesulfonimide (($CF_3SO_2$)$_2$NC$_6$H$_5$) are then added portionwise. The reaction medium is stirred for 24 hours and then hydrolysed with aqueous ammonium chloride solution and extracted with ethyl acetate. The organic phase is washed with water and with brine, dried over anhydrous sodium sulfate, filtered and evaporated under reduced pressure. The product, in the form of a brown oil, is used without purification in the following reaction.

LC/MS: MH$^+$=343 (Rt=9.07 minutes)

46.3. 2-Formyl-5-methoxy-3-phenylbenzoic acid

A solution of about 2.3 mmol of methyl 2-formyl-5-methoxy-3-trifluoromethanesulfonyloxybenzoate in 10 mL of toluene is stirred under argon, and 330 mg (2.7 mmol) of phenylboronic acid, 84 mg of tetrakis palladium and 2.5 mL of aqueous 2N sodium carbonate solution are added. The mixture is stirred at 110° C. for 6 hours in a stoppered tube under argon. Water is added to the cooled reaction medium, and the mixture is washed with ethyl acetate and, after acidification (1N HCl), is then extracted with dichloromethane.

The organic phase is dried over anhydrous sodium sulfate, filtered and evaporated under reduced pressure. The product, in the form of a brown solid, is used without purification in the following reaction.

LC/MS: MH$^+$=257 (Rt=7.76 minutes)

46.4. 7-Methoxy-5-phenyl-2H-phthalazin-1-one

This compound is obtained according to the procedure described in 1.2. by reacting 2-formyl-5-methoxy-3-phenylbenzoic acid with hydrazine hydrate.

m.p.=139° C. (Mettler FP62)
LC/MS: MH$^+$=253 (Rt=7.62 minutes)
$^1$H NMR δ in ppm (DMSO d 6): 3.99 (s, 3H); 7.41 (d, J=2.5 Hz, 1H); 7.48-7.61 (m, 5H); 7.70 (d, J=2.5 Hz, 1H); 7.96 (s, 1H); 12.69 (s, 1H, NH).

46.5. 1-Chloro-7-methoxy-5-phenylphthalazine

This compound is obtained according to the procedure described in 1.3. by reacting 7-methoxy-5-phenyl-2H-phthalazin-1-one with phosphoryl chloride.

m.p.=146° C. (Mettler FP62)
LC/MS: MH$^+$=271 (Rt=8.58 minutes)
$^1$H NMR δ in ppm (DMSO d 6): 4.08 (s, 3H); 7.54-7.62 (m, 6H); 7.67 (d, J=2.7 Hz, 1H); 9.20 (s, 1H).

46.6. 7-Methoxy-N-[1-(naphthalen-2-ylmethyl)piperidin-4-yl]-5-phenylphthalazin-1-amine dihydrochloride This compound is obtained according to the procedure described in 2.4. by reacting 1-chloro-7-methoxy-5-phenylphthalazine with 4-amino-1-(naphthalen-2-yl-methyl)piperidine.

LC/MS: MH$^+$=475 (Rt=5.69 minutes)
$^1$H NMR δ in ppm (DMSO d 6): 1.65-1.80 (m, 2H); 2.03-2.25 (m, 4H); 2.90-3.03 (m, 2H); 3.70 (s, 2H); 4.0 (s, 3H); 4.20-4.30 (m, 1H); 7.03 (d, 1H, NH); 7.36 (d, J=2.5 Hz, 1H); 7.48-7.58 (m, 8H); 7.76 (d, J=2.5 Hz, 1H); 7.84-7.92 (m, 4H); 8.52 (s, 1H).

The dihydrochloride is obtained after treatment with a solution of hydrogen chloride in diethyl ether.

EXAMPLE 47

Compound 147

4-benzyloxymethyl-7-methoxy-N-[1-(naphthalen-2-ylmethyl)piperidin-4-yl]phthalazin-1-amine dihydrochloride 47.1. 2-(2-Benzyloxyacetyl)-5-methoxybenzoic acid This compound is synthesized according to the method described in 3.2. by reacting 2-bromo-5-methoxybenzoic acid pretreated with n-butyllithium with 2-benzyloxy-N-methoxy-N-methylacetamide. The product is used in crude form in the following reaction.

47.2. 4-Benzyloxymethyl-7-methoxy-2H-phthalazin-1-one

This compound is obtained according to the procedure described in 1.2. by reacting 2-(2-benzyloxyacetyl)-5-methoxybenzoic acid with hydrazine hydrate.

m.p.=140° C. (Mettler FP62)
LC/MS: MH$^+$=297 (Rt=7.80 minutes)
$^1$H NMR δ in ppm (DMSO d 6): 3.95 (s, 3H); 4.58 (s, 2H); 4.73 (s, 2H); 7.25-7.37 (m, 5H); 7.53 (dd, J$_1$=9 Hz, J$_2$=2.7 Hz, 1H); 7.66 (d, J=2.7 Hz, 1H); 8.04 (d, J=9 Hz, 1H); 12.59 (s, 1H, NH).

47.3. 4-Benzyloxymethyl-1-chloro-7-methoxyphthalazine

This compound is obtained according to the procedure described in 1.3. by reacting 4-benzyloxymethyl-7-methoxy-2H-phthalazin-1-one with phosphoryl chloride. This oily compound is used as obtained in the following reaction.

47.4. 4-Benzyloxymethyl-7-methoxy-N-[1-(naphthalen-2-ylmethyl)piperidin-4-yl]phthalazin-1-amine dihydrochloride This compound is obtained according to the procedure described in 1.4. by reacting 4-benzyloxymethyl-1-chloro-7-methoxyphthalazine with 4-amino-1-(naphthalen-2-ylmethyl)piperidine.

$^1$H NMR δ in ppm (DMSO d 6): 1.65-1.75 (m, 2H); 2.0-2.25 (m, 4H); 2.90-3.0 (m, 2H); 3.70 (s, 2H); 3.97 (s, 3H); 4.20-4.30 (m, 1H); 4.55 (s, 2H); 4.90 (s, 2H); 7.02 (d, 1H, NH); 7.30-7.36 (m, 5H); 7.45-7.56 (m, 4H); 7.73 (d, J=2.2 Hz, 1H); 7.84-7.92 (m, 4H); 8.06 (d, J=9 Hz, 1H).

The dihydrochloride is obtained after treatment with a solution of hydrogen chloride in diethyl ether.

EXAMPLE 48

Compound 148

4-Hydroxymethyl-7-methoxy-N-[1-(naphthalen-2-ylmethyl)piperidin-4-yl]phthalazin-1-amine A solution of 120 mg of 4-benzyloxymethyl-7-methoxy-N-[1-(naphthalen-2-ylmethyl)piperidin-4-yl]phthalazin-1-amine in 4 mL of dichloromethane is stirred under nitrogen at 0° C., followed by dropwise addition of 2.3 mL of a molar solution of boron trichloride in dichloromethane. The reaction medium is stirred for 1 hour at 0° C. and then for 30 minutes at room temperature. It is hydrolysed with aqueous sodium bicarbonate solution and extracted with dichloromethane. The organic phase is washed with water, dried over anhydrous sodium sulfate, filtered and evaporated under reduced pressure. The residue is purified on a column of silica (eluent: 100/0 to 85/15 v/v dichloromethane/methanol). 58 mg of product are obtained in the form of a beige-coloured powder.

m.p.=102° C. (Köfler)
LC/MS: MH$^+$=429 (Rt=4.78 minutes)
$^1$H NMR δ in ppm (DMSO d 6): 1.60-1.80 (m, 2H); 2.0-2.30 (m, 4H); 2.90-3.0 (m, 2H); 3.72 (s, 2H); 3.97 (s, 3H); 4.18-4.30 (m, 1H); 4.84 (d, J=5.5 Hz, 2H); 5.29 (t, J=5.5 Hz, 1H); 6.95 (d, J=7.5 Hz, 1H, NH); 7.45-7.60 (m, 4H); 7.71(d, J=2.5 Hz, 1H); 7.84-7.93 (m, 4H); 8.05 (d, J=9.2 Hz, 1H).

The dihydrochloride is obtained after treatment with a solution of hydrogen chloride in diethyl ether.

EXAMPLE 49

Compound 18

N-[1-(3-cyanophenylmethyl)-piperidin-4-yl]-7-methoxy-4-(4-methoxyphenyl)phthalazin-1-amine 49.1. 7-Methoxy-4-(4-methoxyphenyl)-N-(piperidin-4-yl)-phthalazin-1-amine The manipulation is performed under an inert atmosphere (nitrogen).

1 g of 10% palladium-on-charcoal and 100 mL of water are introduced into a 500 mL three-necked flask. A solution, prepared beforehand, of 13.3 g of N-(1-benzylpiperidin-4-yl)-7-methoxy-4-(4-methoxyphenyl)phthalazin-1-amine (compound 7) in 50 mL of ethanol and 4.4 mL of formic acid is added dropwise over 1 hour, to this mixture with stirring at 85° C. The reaction mixture is stirred at reflux for 2 hours. After cooling to room temperature, the ethanol is evaporated off under reduced pressure. The mixture is then basified to pH 12 with 2N sodium hydroxide solution and is then extracted with dichloromethane. The organic phase is washed with saturated aqueous sodium chloride solution, dried over anhydrous sodium sulfate and then evaporated under reduced pressure. The yellow oil obtained is concreted in diisopropyl ether to give a white solid. After filtration and drying under vacuum in the presence of phosphorus pentoxide, 10.29 g of 7-methoxy-4-(4-methoxyphenyl)-N-(piperidin-4-yl)-phthalazin-1-amine are obtained (97% yield).

m.p.=143° C. (Mettler FP62)
LC/MS: MH$^+$=365 (Rt=4.88 minutes)
$^1$H NMR δ in ppm (DMSO d 6): 1.5-1.65 (m, 2H); 2.0-2.1 (m, 2H); 2.6-2.7 (m, 2H); 3.0-3.1 (m, 2H); 3.3 (s, 1H, NH); 3.85 (s, 3H); 3.98 (s, 3H); 4.2-4.3 (m, 1H); 7.0 (d, J=7.5 Hz, 1H); 7.10 (d, J=8.5 Hz, 2H); 7.42 (dd, J$_1$=9.2 Hz, J$_2$=2.5 Hz, 1H); 7.52 (d, J=8.5 Hz, 2H); 7.75 (d, J=9.2 Hz, 1H); 7.78 (d, J=2.5 Hz, 1H).

49.2. N-[1-(3-Cyanobenz)-piperidin-4-yl)-7-methoxy-4-(4-methoxyphenyl)phthalazin-1-amine 183 mg (1.4 mmol) of 3-cyanobenzaldehyde are added to a solution of 500 mg (1.4 mmol) of 7-methoxy-4-(4-methoxyphenyl)-N-(piperidin-4-yl)phthalazin-1-amine in 5 mL of 1,2-dichloroethane. The mixture is stirred for 30 minutes under nitrogen, and 378 mg (1.8 mmol) of sodium triacetoxyborohydride are then added. The reaction medium is stirred for 16 hours at room temperature and then hydrolysed with water and 1N sodium hydroxide solution. The dichloromethane extract is washed with saturated aqueous sodium chloride solution, dried over anhydrous sodium sulfate and evaporated under reduced pressure. The residue is purified on a column of silica (eluent: 95/5 (v/v) dichloromethane/methanol). After crystallization from diisopropyl ether, 300 mg of a white powder are obtained.

m.p.=115° C. (Mettler FP62)
LC/MS: MH$^+$=480 (Rt=4.24 minutes)
$^1$H NMR δ in ppm (DMSO d 6): 1.64-1.80 (m, 2H); 2.03-2.28 (m, 4H); 2.85-2.95 (m, 2H); 3.62 (s, 2H); 3.86 (s, 3H); 3.99 (s, 3H); 4.20-4.33 (m, 1H); 7.0 (d, 1H, NH); 7.10 (d, J=8.5 Hz, 2H); 7.44 (dd, J=9.2 Hz, J$_2$=2.5 Hz, 1H); 7.54 (d, J=8.5 Hz, 2H); 7.60 (d, J=9.2 Hz, 1H); 7.70-8.80 (m, 5H).

This reductive amination method was used with several commercially available aldehydes or aldehydes already described in the literature. The synthesized compounds are described in the table.

EXAMPLE 50

Compounds 56, 149 and 150

7-methoxy-4-(4-methoxyphenyl)-N-1-[1-(naphthalen-2-yl-ethyl)piperidin-4yl]phthalazin-1-amine (racemic and enantiomers)

232 mg (1.4 mmol) of 1-naphthalen-2-ylethanone and 0.5 mL of titanium tetraisopropoxide are added to a solution of 500 mg (1.4 mmol) of 7-methoxy-4-(4-methoxyphenyl)-N-(piperidin-4-yl)phthalazin-1-amine in 5 mL of ethanol. The mixture is stirred for 18 hours under nitrogen at room temperature, followed by addition of 58 mg (0.9 mmol) of sodium cyanoborohydride as a solution in 2 mL of ethanol. The reaction medium is stirred for 18 hours at room temperature and then filtered. The filtrate is evaporated to dryness and then purified by chromatography on a column of silica (eluent: 100/0 to 90/10 v/v dichloromethane/methanol). After crystallization from diisopropyl ether, 480 mg of a white powder are obtained.

The dihydrochloride is obtained after treatment with a solution of hydrogen chloride in diethyl ether followed by crystallization from diisopropyl ether.

The enantiomers are separated by liquid chromatography on a Chiralpak AD chiral phase (eluent: 60/40 (v/v) isohexane/ethanol). Their absolute configurations were not determined. These products contain a small amount of residual isohexane.

(−)-7-Methoxy-4-(4-methoxyphenyl)-N-1-1-[(naphthalen-2-ylethyl)piperidin-4-yl]phthalazin-1-amine $[\alpha]_D^{20}$=−24 (c=0.15, dichloromethane)
m.p.=136° C. (Mettler FP62)
LC/MS: MH$^+$=519 (Rt=5.76 minutes)
$^1$H NMR δ in ppm (CDCl$_3$): 1.45 (d, J=6.7 Hz, 3H); 1.64-1.79 (m, 2H); 2.10-2.35 (m, 4H); 2.80-2.90 (m, 1H); 3.08-3.15 (m, 1H); 3.65-3.75 (m, 1H, CH); 3.84 (s, 3H); 3.94 (s, 3H); 4.30-4.40 (m, 1H); 5.13 (d, J=7.2, 1H, NH); 6.98 (d, J=8.7 Hz, 2H); 7.11 (d, J=2.2 Hz, 1H, H-1 naphthyl); 7.27 (dd, J$_1$=9.2 Hz, J$_2$=2.5 Hz, 1H); 7.40-7.45 (m, 2H); 7.52-7.60 (m, 3H); 7.71-7.80 (m, 4H); 7.87 (d, J=9.2 Hz, 1H).

(+)-7-Methoxy-4-(4-methoxyphenyl)-N-1-[1-(naphthalen-2-ylethyl)piperidin-4-yl]phthalazin-1-amine $[\alpha]_D^{20}$=+17 (c=0.18, dichloromethane)
m.p.=132° C. (Mettler FP62)
LC/MS: MH$^+$=519 (Rt=5.76 minutes)
$^1$H NMR δ in ppm (CDCl$_3$): 1.53 (d, J=6.7 Hz, 3H); 1.63-1.80 (m, 2H); 2.15-2.42 (m, 4H); 2.90-3.0 (m, 1H); 3.17-3.27 (m, 1H); 3.65-3.75 (m, 1H, CH); 3.90 (s, 3H); 4.02 (s, 3H); 4.34-4.44 (m, 1H); 4.76 (d, J=7.2, 1H, NH); 7.01 (d, J=2.2 Hz, 1H, H-1 naphthyl); 7.05 (d, J=8.7 Hz, 2H); 7.34 (dd, J$_1$=9.2 Hz, J$_2$=2.5 Hz, 1H); 7.46-7.52 (m, 2H); 7.58-7.66 (m, 3H); 7.74-7.88 (m, 4H); 7.96 (d, J=9.2 Hz, 1H).

EXAMPLE 51

Compound 112

N-[1-(4-hydroxymethylbenzyl)piperidin-4-yl]-7-methoxy-4-(4-methoxyphenyl)phthalazin-1-amine dihydrochloride This product is obtained by reduction of the corresponding methyl ester (compound 107), which was prepared by the reductive amination method described in 49.2, using methyl 4-formylbenzoate.

A solution of 400 mg (0.78 mmol) of methyl {4-[(4-{[7-methoxy-4-(4-methoxyphenyl)phthalazin-1-yl]amino}piperidin-1-yl)methyl]phenyl}carboxylate compound 107) in 6 mL of tetrahydrofuran is added slowly to a suspension of 59 mg (1.6 mmol) of lithium aluminium hydride in 6 mL of tetrahydrofuran, stirred at 0° C. The reaction medium is stirred at 0° C. for 1 hour and then hydrolysed with 0.1 mL of 1N sodium hydroxide solution, 2 mL of water and 0.1 mL of 1N sodium hydroxide solution. It is extracted with dichloromethane. The organic phase is washed with saturated aqueous sodium chloride solution, dried over anhydrous sodium sulfate and then evaporated under reduced pressure. The residue is purified on a column of silica (eluent: 85/15 (v/v) dichloromethane/methanol). After crystallization from diisopropyl ether, 220 mg of a white powder are obtained.

m.p.=139° C. (Mettler FP62)
LC/MS: MH$^+$=485 (Rt=4.99 minutes)
$^1$H NMR δ in ppm (DMSO d 6): 1.60-1.80 (m, 2H); 2.03-2.20 (m, 4H); 2.85-2.96 (m, 2H); 3.51 (s, 2H); 3.85 (s, 3H); 3.97 (s, 3H); 4.20-4.30 (m, 1H); 4.49 (d, J=5.7 Hz, 2H); 5.13 (t, J=5.7 Hz, 1H); 6.98 (d, J=7.5 Hz, 1H, NH); 7.10 (d, J=8.7 Hz, 2H); 7.30 (s, 4H); 7.42 (dd, J$_1$=9.2 Hz, J$_2$=2.5 Hz, 1H); 7.50 (d, J=8.7 Hz, 2H); 7.72-7.77 (m, 2H).

The dihydrochloride is obtained after treatment with a solution of hydrogen chloride in diethyl ether.

EXAMPLE 52

Compound 113

N-[1-(4-aminomethylbenzyl)piperidin-4-yl]-7-methoxy-4-(4-methoxyphenyl)phthalazin-1-amine trihydrochloride This product is obtained by reduction of N-[1-(4-cyanobenzyl)piperidin-4-yl)-7-methoxy-4-(4-methoxyphenyl) phthalazin-1-amine (compound 108), which was prepared via the reductive amination method described in 49.2, using 4-cyanobenzaldehyde.

8 mL of tetrahydrofuran are stirred at 10° C. and 394 mg (10 mmol) of sodium borohydride are added. Next, 0.8 mL (10 mmol) of trifluoroacetic acid is added dropwise. The reaction medium is stirred for 10 minutes, and a solution of 1 g (2 mmol) of N-[1-(4-cyanobenzyl)piperidin-4-yl)-7-methoxy-4-(4-methoxyphenyl)phthalazin-1-amine in 8 mL of tetrahydrofuran is then introduced. The reaction medium is stirred overnight at room temperature and is then concentrated under reduced pressure. 10 mL of 10% hydrochloric acid are added and the solution is refluxed for 1 hour 30 minutes. After cooling, the reaction medium is washed with diethyl ether and then basified with 1N sodium hydroxide solution and extracted with ethyl acetate. The organic phase is washed with saturated aqueous sodium chloride solution, dried over anhydrous sodium sulfate and then evaporated under reduced pressure. After crystallization from diisopropyl ether, 850 mg of a white powder are obtained.

m.p.=203° C. (Mettler FP62)
LC/MS: MH$^+$=484 (Rt=4.42 minutes)
$^1$H NMR δ in ppm (DMSO d 6): 1.60-1.80 (m, 2H); 2.0-2.20 (m, 4H); 2.85-2.96 (m, 2H); 3.20-3.40 (s, NH$_2$)3.50 (s, 2H); 3.70 (s, 2H); 3.85 (s, 3H); 3.98 (s, 3H); 4.20-4.30 (m, 1H); 6.98 (d, J=7.5 Hz, 1H, NH); 7.10 (d, J=8.7 Hz, 2H); 7.20-7.35 (m, 4H); 7.42 (dd, J$_1$=9.2 Hz, J$_2$=2.5 Hz, 1H); 7.52 (d, J=8.7 Hz, 2H); 7.74-7.77 (m, 2H).

The dihydrochloride is obtained after treatment with a solution of hydrogen chloride in diethyl ether.

EXAMPLE 53

Compounds 123

53.1 {4-[(4-{[7-Methoxy-4-(4-methoxyphenyl)phthalazin-1-yl]amino}piperidin-1-yl)methyl] phenyl}carboxylic acid (dihydrochloride)

3.1 mL of 2N sodium hydroxide and 5 mL of dichloromethane are added to a solution of 1.6 g (3.1 mmol) of methyl N-{4-[(4-{[7-methoxy-4-(4-methoxyphenyl)phthalazin-1-yl]amino}piperidin-1-yl)methyl] phenyl}carboxylate in 20 mL of methanol. The mixture is stirred at room temperature for 20 hours and then acidified with 1N hydrochloric acid. It is evaporated under reduced pressure and the residue is taken up in dichloromethane and ethanol. A white precipitate forms, which is washed with diisopropyl ether and then dried. 1.27 g of a white powder are obtained (72% yield).

m.p.=295° C. (Mettler FP62)
LC/MS: MH$^+$=499 (Rt=5.12 minutes)
$^1$H NMR δ in ppm (DMSO d 6): 2.15-2.50 (m, 4H); 3.0-3.20 (m, 2H); 3.40-3.60 (m, 2H); 3.89 (s, 3H); 4.09 (s, 3H); 4.20-4.30 (m, 1H); 4.40 (s, 2H); 7.21 (d, J=8.5 Hz, 2H); 7.63 (d, J=8.5 Hz, 2H); 7.72 (dd, J$_1$=9 Hz, J$_2$=2.2 Hz, 1H); 7.83 (d, J=8.2 Hz, 2H); 7.93 (d, J=9 Hz, 1H); 8.04 (d, J=8.2 Hz, 2H); 8.46 (s, 1H); 11.16 (s, 1H, COOH); 13.17 (s, 1H, NH).

53.2 N-{4-[(4-{[7-Methoxy-4-(4-methoxyphenyl) phthalazin-1-yl]amino}piperidin-1-yl)methyl] phenyl}carboxamide dihydrochloride 0.29 mL (2.3 mmol) of N-ethylmorpholine is added to a stirred suspension of 400 mg (0.7 mmol) of {4-[(4-{[7-methoxy-4-(4-methoxyphenyl)phthalazin-1-yl]amino}piperidin-1-yl)methyl]phenyl}carboxylic acid (dihydrochloride) in 10 mL of tetrahydrofuran at 0° C., followed by dropwise addition of 0.074 mL (0.77 mmol) of ethyl chloroformate. The mixture is stirred for 1 hour at 0° C., and 0.6 mL (3.5 mmol) of a 20% aqueous ammonia solution is then added slowly. The reaction medium is stirred for 20 hours at room temperature and is then concentrated under reduced pressure. 1N sodium hydroxide is added to the residue and the mixture is then extracted with dichloromethane. The organic phase is washed with saturated aqueous sodium chloride solution, dried over anhydrous sodium sulfate and then evaporated under reduced pressure. The residue is purified on a column of silica (eluent: 85/15 (v/v) dichloromethane/methanol). 150 mg of a colourless oil are obtained.

LC/MS: MH$^+$=498 (Rt=4.88 minutes)
$^1$H NMR δ in ppm (DMSO d 6): 1.65-1.80 (m, 2H); 2.05-2.25 (m, 4H); 2.85-2.95 (m, 2H); 3.58 (s, 2H); 3.85 (s, 3H); 3.98 (s, 3H); 4.20-4.30 (m, 1H); 6.99 (d, J=7.3 Hz, 1H, NH); 7.09 (d, J=6.7 Hz, 2H); 7.30 (s, 1H); 7.40-7.45 (m, 3H); 7.51 (d, J=6.7 Hz, 2H); 7.72-7.76 (m, 2H); 7.86 (d, J=8.2 Hz, 2H); 7.93 (s, 1H).

The dihydrochloride is obtained after treatment with a solution of hydrogen chloride in diethyl ether.

EXAMPLE 54

Compounds 139

1-{4-[(4-{[7-Methoxy-4-(4-methoxyphenyl)phthalazin-1-yl]amino}piperidin-1-yl)methyl] phenyl}ethanol dihydrochloride 56 mg (1.2 mmol) of sodium borohydride are added to a suspension of 300 mg (0.6 mmol) of 1-{4-[(4-{[7-methoxy-4-(4-methoxyphenyl)phthalazin-1-yl]amino}piperidin-1-yl) methyl]phenyl}ethanone (compound 121) in 6 mL of methanol. The mixture is stirred for 24 hours at room temperature and then for 30 minutes at reflux. After cooling the reaction medium to 10° C., 1 mL of acetone is added and the mixture is then evaporated under reduced pressure. The residue is purified on a column of silica (eluent: 100/0 to 85/15 (v/v) dichloromethane/methanol). 300 mg of a white powder are obtained.

LC/MS: MH+=499 (Rt=5.06 minutes)

¹H NMR δ in ppm (DMSO d 6): 1.07 (d, J=7 Hz, 3H); 1.65-1.80 (m, 2H); 2.05-2.25 (m, 4H); 2.85-2.95 (m, 2H); 3.51 (s, 2H); 3.85 (s, 3H); 3.98 (s, 3H); 4.20-4.30 (m, 1H); 4.68-4.77 (m, 1H); 5.10 (d, J=4.2 Hz, 1H, OH); 6.99 (d, J=7.5 Hz, 1H, NH); 7.09 (d, J=8.7 Hz, 2H); 7.26-7.34 (m, 4H); 7.43 (dd, J₁=9 Hz, J₂=2.5 Hz, 1H); 7.52 (d, J=8.7 Hz, 2H); 7.73-7.77 (m, 2H).

The dihydrochloride is obtained after treatment with a solution of hydrogen chloride in diethyl ether.

EXAMPLE 55

Compounds 140

7-Methoxy-4-(4-methoxyphenyl)-N-{1-[4-(pyrrolidin-1-ylmethyl)benzyl]-piperidin-4-yl}phthalazin-1-amine trihydrochloride A solution of 360 mg (0.65 mmol) of 7-methoxy-4-(4-methoxyphenyl)-N-{1-[4-(pyrrolidin-1-yl-carboxy)benzyl]piperidin-4-yl}phthalazin-1-amine in 6 mL of tetrahydrofuran is stirred at 0° C., and 50 mg (1.3 mmol) of lithium aluminium hydride are added. The mixture is refluxed for 3 hours and then cooled and successively hydrolysed with 0.25 mL of water, 0.25 mL of 6N sodium hydroxide and 0.75 mL of water. The suspension obtained is filtered and evaporated under reduced pressure. The residue is purified on a column of silica (eluent: from 100/0 to 80/20 (v/v) dichloromethane/methanol). 40 mg of a white gummy product are obtained.

LC/MS: MH+=538 (Rt=4.50 minutes)

The dihydrochloride is obtained after treatment with a solution of hydrogen chloride in diethyl ether.

EXAMPLE 56

Compounds 151

N-[1-(4-Dimethylaminomethylbenzyl)piperidin-4-yl]-7-methoxy-4-(4-methoxyphenyl)phthalazin-1-amine trihydrochloride A mixture of 400 mg (0.82 mmol) of N-[1-(4-aminomethylbenzyl)piperidin-4-yl]-7-methoxy-4-(4-methoxyphenyl) phthalazin-1-amine and 0.2 mL (5 mmol) of formic acid is stirred at 0° C., and 0.32 mL (4.2 mmol) of aqueous 37% formaldehyde solution and 0.5 mL of water are added. The reaction medium is stirred at 90° C. for 8 hours and then at room temperature for 16 hours. 1N sodium hydroxide is added and the mixture is then extracted with dichloromethane. The organic phase is washed with saturated aqueous sodium chloride solution, dried over anhydrous sodium sulfate and then evaporated under reduced pressure. The residue is purified using a resin of methyl isocyanate grafted onto polystyrene. 300 mg of product are obtained in the form of a yellow oil.

LC/MS: MH+=512 (Rt=4.43 minutes)

¹H NMR δ in ppm (DMSO d 6): 1.65-1.80 (m, 2H); 2.00-2.15 (m, 4H); 2.15 (s, 6H); 2.85-2.95 (m, 2H); 3.37 (s, 2H); 3.51 (s, 2H); 3.85 (s, 3H); 3.98 (s, 3H); 4.20-4.30 (m, 1H); 6.99 (d, J=7.6 Hz, 1H, NH); 7.09 (d, J=8.5 Hz, 2H); 7.20-7.34 (m, 4H); 7.43 (dd, J₁=9 Hz, J₂=2.3 Hz, 1H); 7.52 (d, J=8.5 Hz, 2H); 7.73-7.77 (m, 2H).

The trihydrochloride is obtained after treatment with a solution of hydrogen chloride in diethyl ether.

EXAMPLE 57

Compounds 94

4-(4-Methoxyphenyl)-7-methoxy-N-[(3R)-1-(naphthalen-2-ylmethyl)pyrrolidin-3-yl]phthalazin-1-amine dihydrochloride

57.1 (3R)-1-(Naphthalen-2-ylmethyl)-3-tert-butyloxycarbonylaminopyrrolidine This compound was prepared via the reductive amination method described in 49.2, by reaction of (R)-3-tert-butyloxycarbonylaminopyrrolidine with 2-naphthaldehyde. The residue is purified on a column of silica (eluent: from 100/0 to 90/10 (v/v) dichloromethane/methanol).

LC/MS: MH+=327 (Rt=6.34 minutes)

¹H NMR δ in ppm (DMSO d 6): 1.37 (m, 10H); 1.50-1.65 (m, 1H); 1.95-2.15 (m, 1H); 2.25-2.35 (m, 1H); 2.52 (m, 1H); 2.70-2.80 (m, 1H); 3.71 (s, 2H); 3.85-3.95 (m, 1H); 6.95 (d, 1H, NH); 7.45-7.55 (m, 3H); 7.80 (s, 1H); 7.85-7.95 (m, 3H).

57.2. (3R)-1-(Naphthalen-2-ylmethyl)pyrrolidin-3-ylamine

A solution of 2.5 g (7.66 mmol) of compound 57-1 in 25 mL of 2.5M HCl-EtOAc is heated at 80° C. for 6 hours and then at room temperature for 16 hours. The reaction medium is filtered. The precipitate is washed with ethyl acetate and then oven-dried. It is taken up in a mixture of dichloromethane and 1N sodium hydroxide, and then extracted with dichloromethane. The organic phase is washed with saturated aqueous sodium chloride solution, dried over anhydrous sodium sulfate and then evaporated under reduced pressure.

LC/MS: MH+=227 (Rt=2.71 minutes)

¹H NMR δ in ppm (DMSO d 6): 1.35-1.45 (m, 1H); 1.50-1.85 (m, 1H); 1.95-2.15 (m, 1H); 2.15-2.20 (m, 1H); 2.45-2.75 (m, 4H); 3.30-3.40 (m, 1H); 3.65-3.8 (m, 2H); 7.4-7.55 (m, 3H); 7.80 (s, 1H); 7.85-7.95 (m, 3H).

57.3. 4-(4-Methoxyphenyl)-7-methoxy-N-[(3R)-1-(naphthalen-2-ylmethyl)pyrrolidin-3-yl]phthalazin-1-amine This compound is obtained according to the method described in step 1.4 of Example 1, by reaction of (3R)-1-(naphthalen-2-ylmethyl)pyrrolidin-3-ylamine with 1-chloro-7-methoxy-4-(4-methoxyphenyl)phthalazine. The residue is purified on a column of silica (eluent: from 100/0 to 85/15 (v/v) dichloromethane/methanol).

LC/MS: MH+=491 (Rt=5.93 minutes)

The dihydrochloride is obtained after treatment with a solution of hydrogen chloride in diethyl ether $[\alpha]_D^{20}$=−50 (c=1, MeOH)

EXAMPLE 58

Compounds 96

4-(4-Methoxyphenyl)-7-methoxy-N-[(3S)-1-(naphthalen-2-ylmethyl)pyrrolidin-3-yl]phthalazin-1-amine

58.1. (3S)-1-(Naphthalen-2-ylmethyl)-3-tert-butyloxycarbonylamino-pyrrolidine This compound was obtained via the reductive amination method described in 49.2, by reaction of (S)-3-tert-butyloxycarbonylaminopyrrolidine with 2-naphthaldehyde. The residue is purified on a column of silica (eluent: from 100/0 to 90/10 (v/v) dichloromethane/methanol).

LC/MS: MH⁺=327 (Rt=6.40 minutes)

¹H NMR δ in ppm (DMSO d 6): 1.37 (m, 10H); 1.50-1.65 (m, 1H); 1.95-2.15 (m, 1H); 2.25-2.35 (m, 1H); 2.52 (m, 1H); 2.70-2.80 (m, 1H); 3.71 (s, 2H); 3.85-3.95 (m, 1H); 6.95 (d, 1H, NH); 7.45-7.55 (m, 3H); 7.80 (s, 1H); 7.85-7.95 (m, 3H).

58.2. (3S)-1-(Naphthalen-2-ylmethyl)pyrrolidin-3-ylamine

The deprotection of the amine was performed according to the method described in 57.2.

LC/MS: MH⁺=227 (Rt=2.89 minutes)

¹H NMR δ in ppm (DMSO d 6): 1.35-1.45 (m, 1H); 1.50-1.85 (m, 1H); 1.95-2.15 (m, 1H); 2.15-2.20 (m, 1H); 2.45-2.75 (m, 4H); 3.30-3.40 (m, 1H); 3.65-3.8 (m, 2H); 7.40-7.55 (m, 3H); 7.80 (s, 1H); 7.85-7.95 (m, 3H).

58.3. 4-(4-Methoxyphenyl)-7-methoxy-N-[(3S)-1-(naphthalen-2-ylmethyl)pyrrolidin-3-yl]phthalazin-1-amine This compound is obtained according to the method described in step 1.4 of Example 1, by reacting (3S)-1-(naphthalen-2-ylmethyl)pyrrolidin-3-ylamine with 1-chloro-7-methoxy-4-(4-methoxyphenyl)phthalazine. The residue is purified on a column of silica (eluent: from 100/0 to 85/15 (v/v) dichloromethane/methanol).

LC/MS: MH⁺=491 (Rt=5.93 minutes)

The dihydrochloride is obtained after treatment with a solution of hydrogen chloride in diethyl ether.

[α]$_D^{20}$=+47 (c=1, MeOH)

TABLE (I)

| No. | A-N-B | R₃R₂/L-R₁ | R₄ | R₅ | R₆ | R₇ | R₈ | Salt and/or Solvates | m.p. (°C.) | LC/MS (M + H)+; Rt (minutes) |
|---|---|---|---|---|---|---|---|---|---|---|
| 1 | 4-methylpiperidinyl | 2-naphthylmethyl | phenyl | H | H | OMe | H | H₂O (0.25/1) | 121 (K) | 475; Rt = 5.15 |
| 2 | 4-methylpiperidinyl | 2-naphthylmethyl | 2-methoxyphenyl | H | H | OMe | H | H₂O (0.75/1) | 158 (M) | 505; Rt = 5.16 |
| 3 | 4-methylpiperidinyl | 2-naphthylmethyl | 4-methoxyphenyl | H | H | OMe | H | H₂O (0.25/1) iPr₂O (0.2/1) | 195 (M) | 505; Rt = 5.28 |
| 4 | azabicyclic | 2-naphthylmethyl | 4-methoxyphenyl | H | H | OMe | H | H₂O (0.25/1) | 176 (M) | 531; Rt = 5.43 |

TABLE-continued (I)

| No. | A—N B | R₃ R₂ L R₁ | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 5 | 4-methylpiperidine | naphthalen-2-ylmethyl | 3-methoxyphenyl | H | H | OMe | H | H₂O (0.5/1) | 154 (M) | 505; Rt = 5.28 |
| 6 | 4-methylpiperidine | benzyl | 3-methoxyphenyl | H | H | OMe | H | H₂O (0.25/1) | 176 (M) | 455; Rt = 4.80 |
| 7 | 4-methylpiperidine | benzyl | 4-methoxyphenyl | H | H | OMe | H | H₂O (0.25/1) iPr₂O (0.15/1) | 150 (M) | 455; Rt = 4.71 |
| 8 | 4-methylpiperidine | benzyl | thiophen-2-yl | H | H | OMe | H | H₂O (0.3/1) iPr₂O (0.2/1) | 115 (M) | 431; Rt = 4.72 |
| 9 | 4-methylpiperidine | naphthalen-2-ylmethyl | 4-methoxyphenyl | H | H | Me | H | H₂O (0.3/1) | 198 (M) | 489; Rt = 5.27 |
| 10 | 4-methylpiperidine | naphthalen-2-ylmethyl | 3,4-dimethoxyphenyl | H | H | OMe | H | H₂O (0.5/1) | 131 (K) | 535; Rt = 5.13 |

TABLE-continued (I)

| No. | A—N / B (with substituent) | R₃, R₂, R₁, L group | R₄ | R₅ | R₆ | R₇ | R₈ | Salt and/or Solvates | m.p. (°C.) | LC/MS (M + H)+; Rt (minutes) |
|---|---|---|---|---|---|---|---|---|---|---|
| 11 | 4-methylpiperidine | benzyl (CH₂-Ph) | 4-methoxyphenyl | OMe | H | OMe | H | — | 168 (K) | 485; Rt = 4.82 |
| 12 | N-methyl tropane | benzyl | 2-thienyl | H | H | OMe | H | H₂O (0.5/1) | 209 (M) | 457; Rt = 7.93 |
| 13 | 4-methylpiperidine | benzyl | H | OMe | H | OMe | H | H₂O (0.5/1) | 169 (M) | 379; Rt = 4.05 |
| 14 | 4-methylpiperidine | 2-naphthylmethyl | H | OMe | H | OMe | H | H₂O (0.5/1) | 206 (M) | 429; Rt = 4.60 |
| 15 | 4-methylpiperidine | 2-naphthylmethyl | 4-methoxyphenyl | OMe | H | OMe | H | HCl (2/1) H₂O (1.5/1) | 212 (K) | 535; Rt = 5.26 |
| 16 | 4-methylpiperidine | benzyl | 2,5-dimethylthienyl | H | H | OMe | H | H₂O (0.7/1) iPr₂O (0.1/1) | 155 (M) | 445; Rt = 5.02 |
| 17 | 4-methylpiperidine | 2-naphthylmethyl | phenyl | H | H | OMe | H | H₂O (2/1) Et₂O (0.23/1) | 199 (M) | 475; Rt = 5.70 |

TABLE-continued
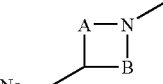
(I)
| No. | A-B / N-Me ring | R₃R₂/L/R₁ | R₄ | R₅ | R₆ | R₇ | R₈ | Salt and/or Solvates | m.p. (°C.) | LC/MS (M + H)+; Rt (minutes) |
|---|---|---|---|---|---|---|---|---|---|---|
| 18 | 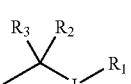 | 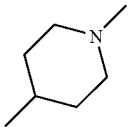 | 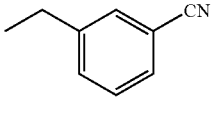 | H | H | OMe | H | H₂O (0.5/1) iPr₂O (0.15/1) | 115 (M) | 480; Rt = 4.24 |
| 19 | 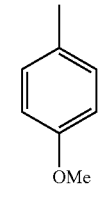 | 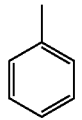 | 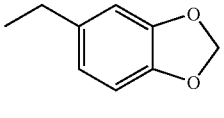 | H | H | OMe | H | HCl (2/1) H₂O (1/1) | 235 (B) | 499; Rt = 5.31 |
| 20 | 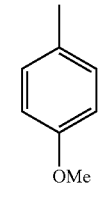 | 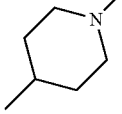 | Et | H | H | OMe | H | H₂O (0.85/1) | 135 (M) | 427; Rt = 5.16 |
| 21 | 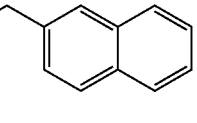 | 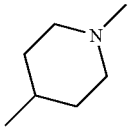 | 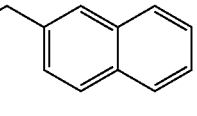 | H | H | OMe | H | H₂O (0.7/1) | 104 (M) | 489; Rt = 5.71 |
| 22 | 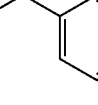 | 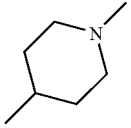 | 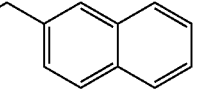 | OMe | H | OMe | H | — | 163 (M) | 519; Rt = 5.92 |
| 23 | 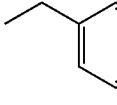 | 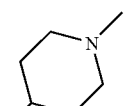 | Et | OMe | H | OMe | H | H₂O (0.6/1) | 250 (M) | 457; Rt = 4.48 |
| 24 | 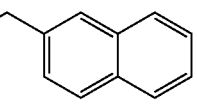 | 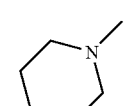 | —CH₂—O—CH₃ | H | H | OMe | H | HCl (1/1) H₂O (1.2/1) | 176 (M) | 443; Rt = 4.01 |

TABLE-continued
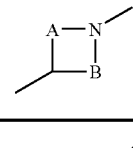
(I)
| No. | A—N B | R3 R2 L R1 | R4 | R5 | R6 | R7 | R8 | Salt and/or Solvates | m.p. (° C.) | LC/MS (M + H)+; Rt (minutes) |
|---|---|---|---|---|---|---|---|---|---|---|
| 25 | 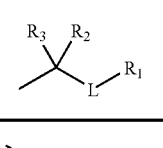 | 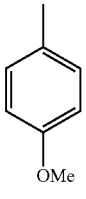 | 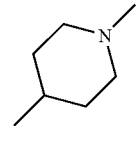 | H | H | OMe | H | $H_2O$ (0.25/1) | 223 (M) | 505; Rt = 4.77 |
| 26 | 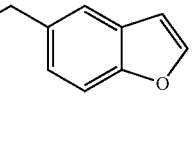 | 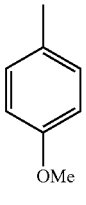 | 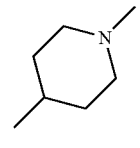 | H | H | OMe | H | $H_2O$ (0.8/1) | 160 (M) | 495; Rt = 4.53 |
| 27 | 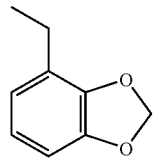 | 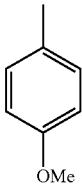 | 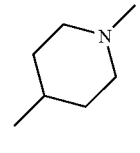 | H | H | OMe | H | $H_2O$ (0.5/1) | 180 (M) | 499; Rt = 4.39 |
| 28 | 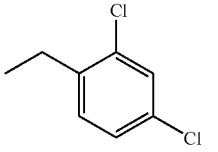 | 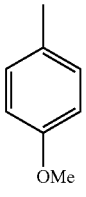 | 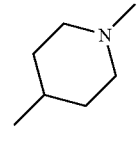 | H | H | OMe | H | $H_2O$ (0.5/1) | 212 (K) | 523; Rt = 4.56 |
| 29 | 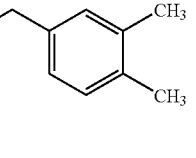 | 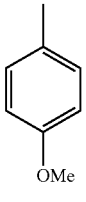 | | H | H | OMe | H | $H_2O$ (0.5/1) | 130 (K) | 483; Rt = 4.53 |

TABLE-continued (I)

| No. | A-N-B (ring) | R₃R₂/L/R₁ group | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 30 | 4-methyl-piperidin-1-yl | 3,4-dichlorobenzyl | 4-methoxyphenyl | H | H | OMe | H | H₂O (0.5/1) | 208 (K) | 523; Rt = 4.83 |
| 31 | 4-methyl-piperidin-1-yl | (1-methyl-1H-indol-2-yl)methyl | 4-methoxyphenyl | H | H | OMe | H | H₂O (0.75/1) | 122 (K) | 508; Rt = 4.91 |
| 32 | 4-methyl-piperidin-1-yl | 3,4-dimethoxybenzyl | 4-methoxyphenyl | H | H | OMe | H | H₂O (0.75/1) | 110 (K) | 515; Rt = 4.44 |
| 33 | 4-methyl-piperidin-1-yl | naphthalen-2-ylmethyl | cyclopropyl | H | H | OMe | H | H₂O (0.1/1) | 154 (K) | 439; Rt = 4.52 |
| 34 | 4-methyl-piperidin-1-yl | 4-(trifluoromethyl)benzyl | 4-methoxyphenyl | H | H | OMe | H | H₂O (0.8/1) | 214 (K) | 523; Rt = 10.08 |
| 35 | 4-methyl-piperidin-1-yl | (6-methoxynaphthalen-2-yl)methyl | 4-methoxyphenyl | H | H | OMe | H | H₂O (1/1) iPr₂O (0.3/1) | 119 (K) | 535; Rt = 4.90 |

TABLE-continued
(I)
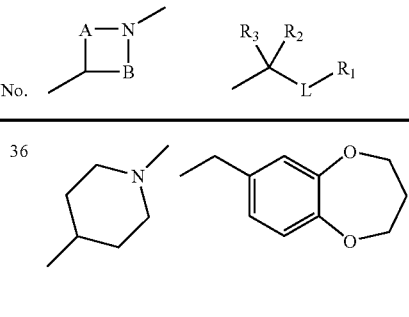
| No. | 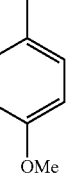 | R₃ R₂<br>R₁<br>L | R₄ | R₅ | R₆ | R₇ | R₈ | Salt and/or Solvates | m.p. (°C.) | LC/MS (M + H)+; Rt (minutes) |
|---|---|---|---|---|---|---|---|---|---|---|
| 36 | 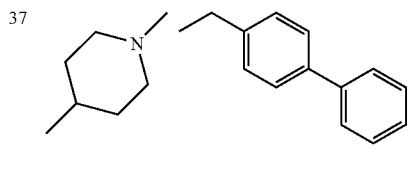 | 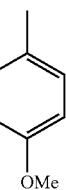 | 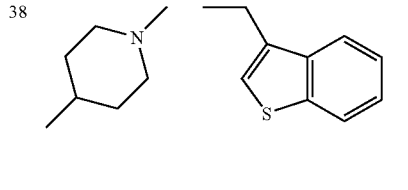 | H | H | OMe | H | H₂O (1.1/1) | 130 (K) | 527; Rt = 4.71 |
| 37 | 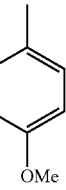 | 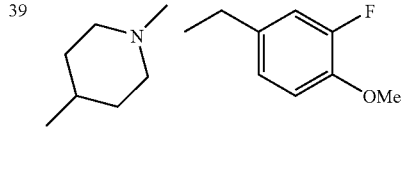 | 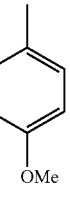 | H | H | OMe | H | iPr₂O (0.15/1) | 228 (K) | 531; Rt = 5.17 |
| 38 | 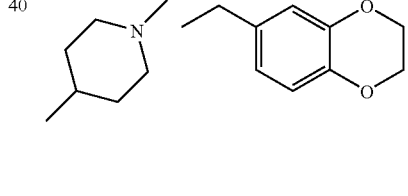 | 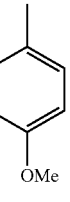 | (p-methoxyphenyl) | H | H | OMe | H | — | 236 (K) | 511; Rt = 4.51 |
| 39 | (4-methylpiperidin-1-yl) | (3-fluoro-4-methoxybenzyl) | (p-methoxyphenyl) | H | H | OMe | H | H₂O (0.5/1) | 280 (M) | 503; Rt = 4.68 |
| 40 | (4-methylpiperidin-1-yl) | (2,3-dihydro-1,4-benzodioxin-6-ylmethyl) | (p-methoxyphenyl) | H | H | OMe | H | H₂O (0.6/1) | 228 (K) | 513; Rt = 4.22 |

TABLE-continued
(I)
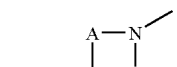
| No. | 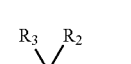 | R₃, R₂, R₁, L | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 41 |  |  |  | H | H | OMe | H | H₂O (0.6/1) | 190 (K) | 506; Rt = 4.20 |
| 42 |  |  |  | H | H | OMe | H | HCl (2/1) H₂O (3.5/1) | 272 (M) | 519; Rt = 4.66 |
| 43 |  |  | 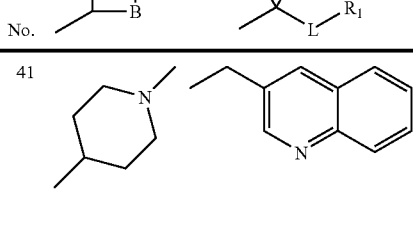 | H | H | OMe | H | H₂O (1.5/1) | 181 (M) | 509; Rt = 5.22 |
| 44 | 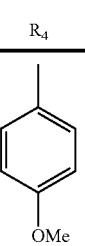 | 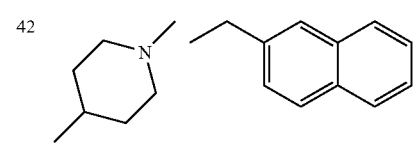 | 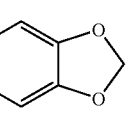 | H | H | OMe | H | H₂O (0.25/1) | 265 (M) | 535; Rt = 4.98 |
| 45 | 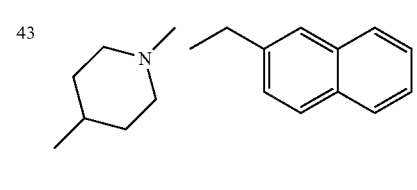 | 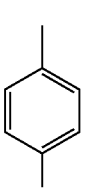 | 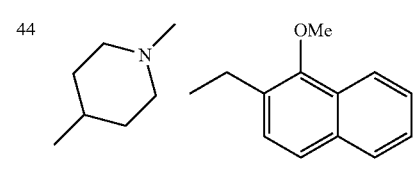 | H | H | OMe | H | H₂O (0.75/1) | 230 (K) | 543; Rt = 5.27 |
| 46 | 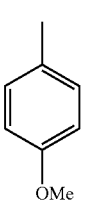 | 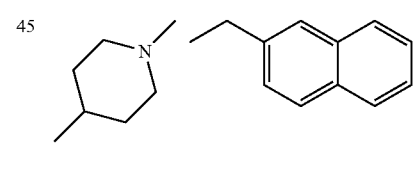 | 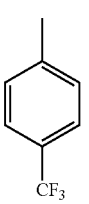 | H | H | OMe | H | H₂O (0.5/1) | 201 (M) | 497; Rt = 4.64 |

TABLE-continued (I)

| No. | ![A-N-B with methyl] | ![R3,R2,R1,L group] | R4 | R5 | R6 | R7 | R8 | Salt and/or Solvates | m.p. (° C.) | LC/MS (M + H)+; Rt (minutes) |
|---|---|---|---|---|---|---|---|---|---|---|
| 47 | 4-methylpiperidin-1-yl | 3-methoxynaphthalen-2-yl ethyl | 4-OMe-phenyl | H | H | OMe | H | H₂O (1/1) | 200 (M) | 535; Rt = 4.97 |
| 48 | 4-methylpiperidin-1-yl | benzothiophen-2-yl ethyl | 4-OMe-phenyl | H | H | OMe | H | H₂O (0.25/1) | 196 (M) | 511; Rt = 4.84 |
| 49 | 4-methylpiperidin-1-yl | 1-phenylprop-2-yl | 4-OMe-phenyl | H | H | OMe | H | H₂O (0.35/1) iPr₂O (0.2/1) | 149 (M) | 483; Rt = 4.69 |
| 50 | 4-methylpiperidin-1-yl | tetrahydronaphthalen-2-yl ethyl | 4-OMe-phenyl | H | H | OMe | H | H₂O (0.55/1) | 266 (M) | 509; Rt = 4.82 |
| 51 | 4-methylpiperidin-1-yl | naphthalen-2-yl ethyl | cyclopentyl | H | H | OMe | H | HCl (2/1) H₂O (2.2/1) | 244 (K) | 467; Rt = 4.84 |
| 52 | 4-methylpiperidin-1-yl | phenethyl | 4-OMe-phenyl | H | H | OMe | H | H₂O (0.5/1) iPr₂O (0.15/1) | 152 (M) | 469; Rt = 4.23 |

TABLE-continued
(I)
| No. | A-N B | R3 R2 R1 L | R4 | R5 | R6 | R7 | R8 | Salt and/or Solvates | m.p. (° C.) | LC/MS (M + H)+; Rt (minutes) |
|---|---|---|---|---|---|---|---|---|---|---|
| 53 | 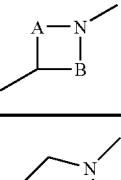 | 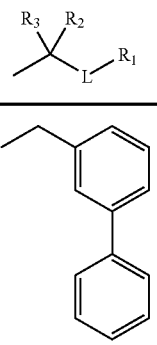 | 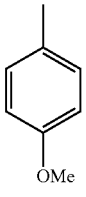 | H | H | OMe | H | H₂O (1.5/1) | 212 (M) | 531; Rt = 6.14 |
| 54 | 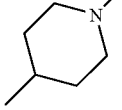 | 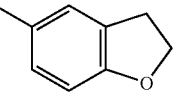 | 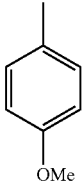 | H | H | OMe | H | H₂O (0.9/1) | 142 (M) | 497; Rt = 5.41 |
| 55 | 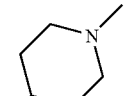 | 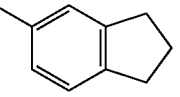 | 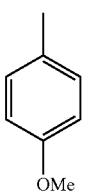 | H | H | OMe | H | H₂O (0.3/1) | 162 (M) | 495; Rt = 5.71 |
| 56 | 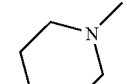 | 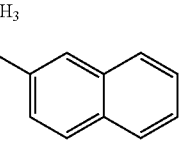 | 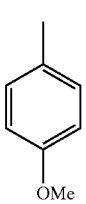 | H | H | OMe | H | HCl (2/1) H₂O (3.6/1) | 274 (M) | 519; Rt = 5.87 |
| 57 | 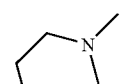 | 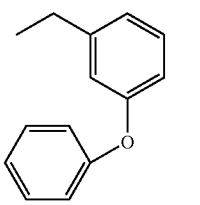 | 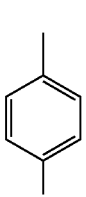 | H | H | OMe | H | H₂O (0.4/1) iPr₂O (0.2/1) | 98 (M) | 547; Rt = 5.34 |

TABLE-continued
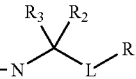
(I)
| No. | ![A-N-B ring] | ![R3 R2 L R1] | R4 | R5 | R6 | R7 | R8 | Salt and/or Solvates | m.p. (° C.) | LC/MS (M + H)+; Rt (minutes) |
|---|---|---|---|---|---|---|---|---|---|---|
| 58 | 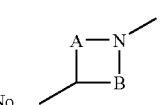 | 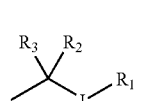 | 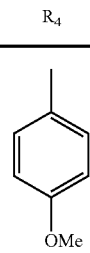 | H | H | OMe | H | H$_2$O (0.4/1) iPr$_2$O (0.04/1) | 186 (M) | 495; Rt = 4.74 |
| 59 | 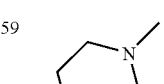 | 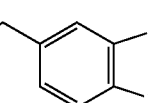 | 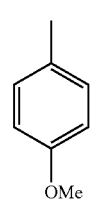 | H | H | OMe | H | H$_2$O (0.6/1) iPr$_2$O (0.02/1) | 180 (K) | 512; Rt = 5.24 |
| 60 | 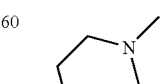 | 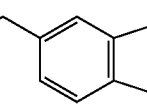 | 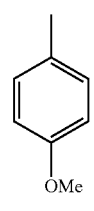 | H | H | OMe | H | H$_2$O (0.25/1) iPr$_2$O (0.04/1) | 176 (K) | 511; Rt = 5.69 |
| 61 | 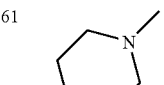 | 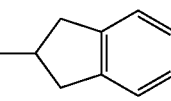 | 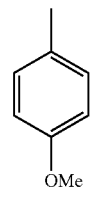 | H | H | OMe | H | H$_2$O (1.8/1) iPr$_2$O (0.1/1) | 118 (K) | 495; Rt = 4.40 |
| 62 | 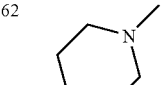 |  | 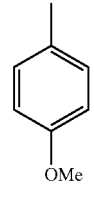 | H | H | OMe | H | H$_2$O (1.3/1) iPr$_2$O (0.13/1) | 114 (K) | 495; Rt = 4.45 |

TABLE-continued (I)

| No. | [A-N-B ring] | [R3,R2,R1,L group] | R4 | R5 | R6 | R7 | R8 | Salt and/or Solvates | m.p. (°C.) | LC/MS (M + H)+; Rt (minutes) |
|---|---|---|---|---|---|---|---|---|---|---|
| 63 | 4-methylpiperidine | 2-ethyl-4-methoxyquinoline | 4-OMe-phenyl | H | H | OMe | H | H₂O (0.7/1) iPr₂O (0.03/1) | 172 (M) | 536; Rt = 5.71 |
| 64 | 4-methylpiperidine | 3-SMe-phenethyl | 4-OMe-phenyl | H | H | OMe | H | H₂O (0.2/1) iPr₂O (0.05/1) | 176 (M) | 501; Rt = 5.53 |
| 65 | 4-methylpiperidine | 3-indolyl-ethyl | 4-OMe-phenyl | H | H | OMe | H | H₂O (0.5/1) iPr₂O (0.07/1) | 257 (M) | 494; Rt = 4.82 |
| 66 | 4-methylpiperidine | 2-naphthyl-ethyl | 4-CH₃-phenyl | H | H | OMe | H | H₂O (0.5/1) iPr₂O (0.01/1) | 135 (M) | 489; Rt = 5.16 |
| 67 | 4-methylpiperidine | 2-naphthyl-ethyl | nBut | H | H | OMe | H | H₂O (0.5/1) | 101 (M) | 455; Rt = 5.59 |
| 68 | 4-methylpiperidine | 3-phenyl-propyl | 4-OMe-phenyl | H | H | OMe | H | H₂O (0.5/1) | 196 (M) | 483; Rt = 5.50 |

TABLE-continued (I)

| No. | A-N B (with methyl) | R3 R2 / L R1 | R4 | R5 | R6 | R7 | R8 | Salt and/or Solvates | m.p. (°C.) | LC/MS (M + H)+; Rt (minutes) |
|---|---|---|---|---|---|---|---|---|---|---|
| 69 | 4-methylpiperidin-1-yl | CH2-CH2-CH=CH-Ph | 4-OMe-C6H4 | H | H | OMe | H | HCl (2/1) H2O (2.8/1) | 210 (K) | 481; Rt = 5.67 |
| 70 | 4-methylpiperidin-1-yl | CH2-naphthalen-2-yl | H | H | H | OMe | H | HCl (0.75/1) H2O (0.2/1) | 189 (M) | 399; Rt = 3.78 |
| 71 | 4-methylpiperidin-1-yl | CH2-naphthalen-2-yl | CH2-cyclopropyl | H | H | OMe | H | — | n.d. | 453; Rt = 4.45 |
| 72 | 4-methylpiperidin-1-yl | CH2-(3-CF3-4-F-C6H3) | 4-OMe-C6H4 | H | H | OMe | H | — | 172 (M) | 541; Rt = 5.79 |
| 73 | 4-methylpiperidin-1-yl | CH2-(3-CF3-4-Cl-C6H3) | 4-OMe-C6H4 | H | H | OMe | H | — | 190 (K) | 557; Rt = 5.96 |
| 74 | 4-methylpiperidin-1-yl | CH2-(3-F-4-CH3-C6H3) | 4-OMe-C6H4 | H | H | OMe | H | — | 210 (M) | 487; Rt = 5.53 |

TABLE-continued
(I)
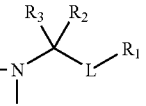
| No. | A-N-B (with R) | R₃R₂L-R₁ | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 75 | 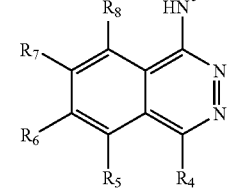 | 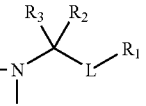 | 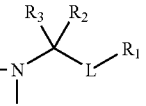 | H | H | OMe | H | HCl (0.75/1) iPr₂O (0.3/1) | 148 (M) | 469; Rt = 5.44 |
| 76 | 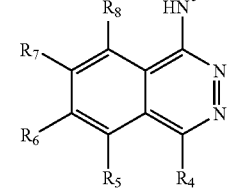 | 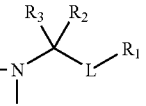 | 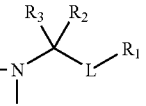 | H | H | OMe | H | H₂O (0.5/1) | 210 (M) | 543; Rt = 6.07 |
| 77 | 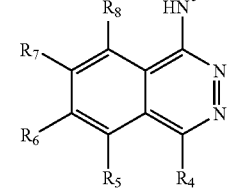 | 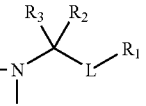 | 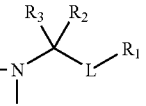 | H | H | OMe | H | H₂O (0.65/1) iPr₂O (0.01/1) | 124 (K) | 506; Rt = 5.50 |
| 78 | 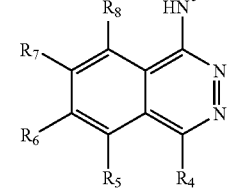 | 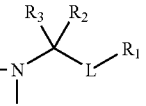 | 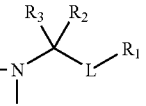 | H | H | OMe | H | — | 192 (M) | 535; Rt = 5.72 |
| 79 | 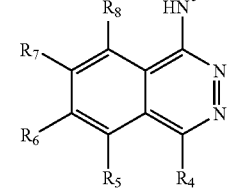 | 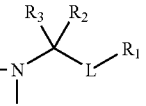 | 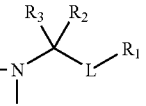 | H | H | OMe | H | — | 168 (M) | 507; Rt = 5.55 |

TABLE-continued (I)

| No. | A-N-B ring (R₃R₂L R₁) | R₄ substituent | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 80 | N-methyl-4-methylpiperidine | 4-F, 3-OMe benzyl (ethyl linker) | 4-OMe phenyl | H | H | OMe | H | H₂O (0.4/1) | 144 (M) | 503; Rt = 5.41 |
| 81 | N-methyl-4-methylpiperidine | 2,4-diMe benzyl (ethyl linker) | 4-OMe phenyl | H | H | OMe | H | HCl (2/1) H₂O (2.3/1) | 290 (M) | 483; Rt = 5.55 |
| 82 | N-methyl-4-methylpiperidine | 2-naphthyl (ethyl linker) | 4-F phenyl | H | H | OMe | H | H₂O (0.65/1) | 175 (M) | 493; Rt = 5.77 |
| 83 | N-methyl-4-methylpiperidine | 3-Me, 4-F benzyl (ethyl linker) | 4-OMe phenyl | H | H | OMe | H | — | 157 (M) | 487; Rt = 5.51 |
| 84 | N-methyl-4-methylpiperidine | 3-F, 4-CF₃ benzyl (ethyl linker) | 4-OMe phenyl | H | H | OMe | H | — | 186 (M) | 541; Rt = 5.85 |

TABLE-continued (I)

| No. | A-N-B (with N-Me) | R₃R₂/L/R₁ | R₄ | R₅ | R₆ | R₇ | R₈ | Salt and/or Solvates | m.p. (°C.) | LC/MS (M + H)+; Rt (minutes) |
|---|---|---|---|---|---|---|---|---|---|---|
| 85 | 4-methylpiperidine | -CH₂-(1-methyl-1H-benzotriazol-5-yl) | 4-methoxyphenyl | H | H | OMe | H | H₂O (1/1) | 163 (M) | 510; Rt = 5.07 |
| 86 | 4-methylpiperidine | -CH₂-(3-fluoro-4-chlorophenyl) | 4-methoxyphenyl | H | H | OMe | H | — | 194 (M) | 507; Rt = 5.58 |
| 87 | 4-methylpiperidine | -CH₂-(1H-indol-5-yl) | 4-methoxyphenyl | H | H | OMe | H | H₂O (1.4/1) iPr₂O (0.3/1) | 281 (M) | 494; Rt = 5.32 |
| 88 | 4-methylpiperidine | -CH₂-(naphthalen-2-yl) | 4-(methoxymethyl)phenyl | H | H | OMe | H | H₂O (0.8/1) iPr₂O (0.3/1) | 155 (M) | 519; Rt = 5.68 |
| 89 | 4-methylpiperidine | -CH₂-(3-methyl-4-methoxyphenyl) | 4-methoxyphenyl | H | H | OMe | H | H₂O (2/1) | 270 (M) | 499; Rt = 5.55 |

TABLE-continued (I)

| No. | A—N—B (with methyl on N) | R3, R2, L, R1 group | R4 | R5 | R6 | R7 | R8 | Salt and/or Solvates | m.p. (°C.) | LC/MS (M + H)+; Rt (minutes) |
|---|---|---|---|---|---|---|---|---|---|---|
| 90 | 1,4-dimethylpiperidine | 3,5-dimethylbenzyl (ethyl linker) | 4-OMe-phenyl | H | H | OMe | H | H₂O (1.3/1) iPr₂O (0.2/1) | 277 (M) | 483; Rt = 5.63 |
| 91 | 1,4-dimethylpiperidine | 4-methyl-3,4-dihydro-2H-benzo[1,4]oxazin-7-yl (ethyl linker) | 4-OMe-phenyl | H | H | OMe | H | H₂O (1.5/1) iPr₂O (0.2/1) | 251 (M) | 526; Rt = 5.41 |
| 92 | 1,4-dimethylpiperidine | 3-chloro-4-methoxybenzyl (ethyl linker) | 4-OMe-phenyl | H | H | OMe | H | H₂O (0.15/1) | 277 (M) | 518; Rt = 5.54 |
| 93 | 1,4-dimethylpiperidine | 3,4-difluorobenzyl (ethyl linker) | 4-OMe-phenyl | H | H | OMe | H | H₂O (0.2/1) | 175 (M) | 491; Rt = 5.40 |
| 94 (R) | (R)-1,3-dimethylpyrrolidine | naphthalen-2-ylmethyl | 4-OMe-phenyl | H | H | OMe | H | HCl (2/1) H₂O (3/1) | 254 (M) | 491; Rt = 5.96 |
| 95 | 1,4-dimethylpiperidine | naphthalen-2-ylmethyl | Me | H | H | OMe | H | — | 188 (M) | 413; Rt = 4.96 |

TABLE-continued
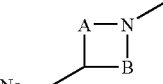
(I)
| No. | ![A-N-B structure] | R3 R2 L R1 | R4 | R5 | R6 | R7 | R8 | Salt and/or Solvates | m.p. (° C.) | LC/MS (M + H)+; Rt (minutes) |
|---|---|---|---|---|---|---|---|---|---|---|
| 96 (S) | 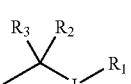 | 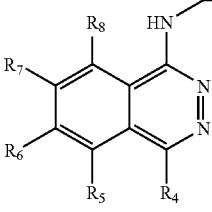 | 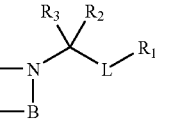 | H | H | OMe | H | HCl (2/1) H2O (2.5/1) | 280 (M) | 491; Rt = 5.96 |
| 97 |  | 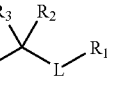 | 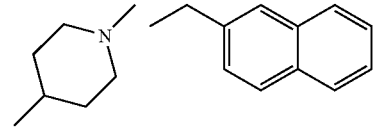 | H | H | OMe | H | HCl (2/1) H2O (2.7/1) Et2O (0.08/1) | 240 (B) | 535; Rt = 5.77 |
| 98 | 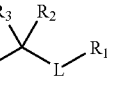 | 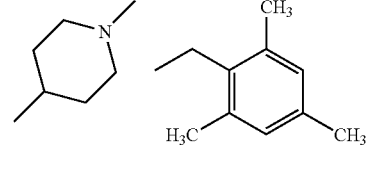 | 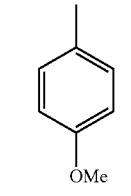 | H | H | OMe | H | H2O (0.5/1) | 145 (M) | 497; Rt = 5.66 |
| 99 | 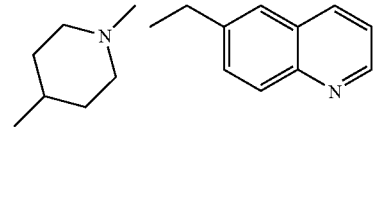 | 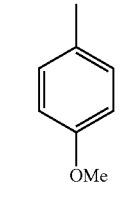 |  | H | H | OMe | H | H2O (0.5/1) | 249 (M) | 506; Rt = 4.00 |
| 100 | 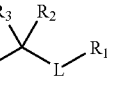 | 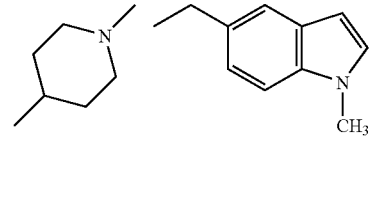 | 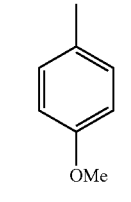 | H | H | OMe | H | H2O (1.5/1) | 161 (M) | 508; Rt = 4.47 |
| 101 | 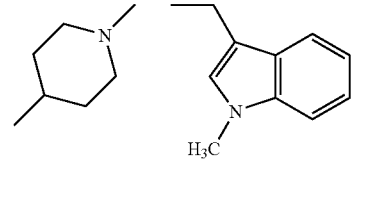 | 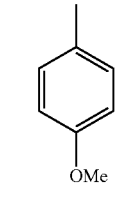 |  | H | H | OMe | H | HCl (2/1) H2O (3.5/1) | 280 (M) | 508; Rt = 5.64 |

TABLE-continued (I)

| No. | A—N B | R₃ R₂ L R₁ | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 102 | 4-methylpiperidinyl | naphthalen-2-ylmethyl | 2,4-dimethoxyphenyl | H | H | OMe | H | HCl (2/1) H₂O (3/1) | 228 (K) | 535; Rt = 5.80 |
| 103 | 4-methylpiperidinyl | naphthalen-2-ylmethyl | 3,5-dimethoxyphenyl | H | H | OMe | H | HCl (2/1) H₂O (2.7/1) Et₂O (0.06/1) | 240 (B) | 535; Rt = 5.93 |
| 104 | 4-methylpiperidinyl | naphthalen-2-ylmethyl | 3-phenylpropyl | H | H | OMe | H | HCl (2/1) H₂O (2.6/1) | 264 (M) | 503; Rt = 5.87 |
| 105 | 4-methylpiperidinyl | naphthalen-2-ylmethyl | 4-(diethylaminomethyl)phenyl | H | H | OMe | H | HCl (3/1) H₂O (2.5/1) | 260 (K) | 560; Rt = 4.87 |
| 106 | 4-methylpiperidinyl | naphthalen-2-ylmethyl | 4-fluorophenyl | H | H | F | H | — | 207 (M) | 481; Rt = 6.04 |

TABLE-continued
(I)
| No. | 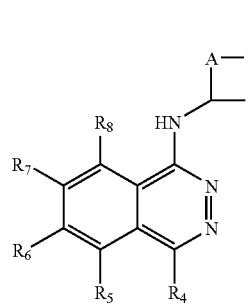 | 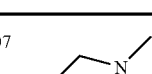 | R_4 | R_5 | R_6 | R_7 | R_8 | Salt and/or Solvates | m.p. (° C.) | LC/MS (M + H)+; Rt (minutes) |
|---|---|---|---|---|---|---|---|---|---|---|
| 107 | 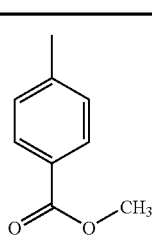 | 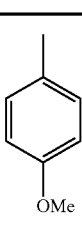 | 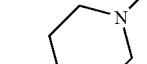 | H | H | OMe | H | HCl (2/1) H$_2$O (2.6/1) | 241 (M) | 513; Rt = 5.36 |
| 108 | 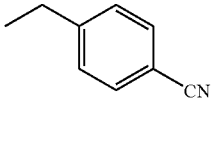 | 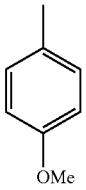 | 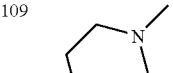 | H | H | OMe | H | HCl (2/1) H$_2$O (2.5/1) | 270 (M) | 480; Rt = 5.23 |
| 109 | 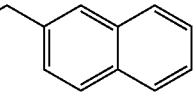 | 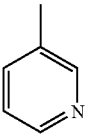 | 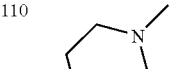 | H | H | OMe | H | HCl (2.6/1) H$_2$O (2.1/1) | 225 (B) | 476; Rt = 5.25 |
| 110 | 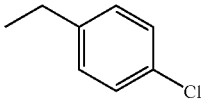 | 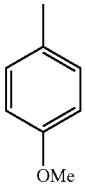 | 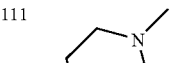 | H | H | OMe | H | HCl (2/1) H$_2$O (2/1) | 277 (M) | 489; Rt = 5.51 |
| 111 | 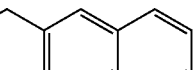 | 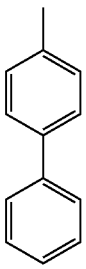 | | H | H | OMe | H | HCl (2/1) H$_2$O (2.3/1) | 292 (M) | 551; Rt = 6.53 |

TABLE-continued

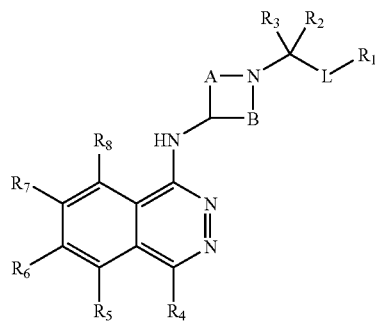

(I)

| No. | A-N-B (with R) | R₃R₂ / L / R₁ | R₄ | R₅ | R₆ | R₇ | R₈ | Salt and/or Solvates | m.p. (°C.) | LC/MS (M + H)+; Rt (minutes) |
|---|---|---|---|---|---|---|---|---|---|---|
| 112 | N-methyl-4-methylpiperidine | 4-(hydroxymethyl)benzyl | 4-OMe-phenyl | H | H | OMe | H | HCl (2/1) H₂O (2.5/1) Et₂O (0.25/1) | 294 (M) | 485; Rt = 4.98 |
| 113 | N-methyl-4-methylpiperidine | 4-(aminomethyl)benzyl | 4-OMe-phenyl | H | H | OMe | H | HCl (3/1) H₂O (3.5/1) | 284 (B) | 484; Rt = 4.38 |
| 114 | N-methyl-4-methylpiperidine | 4-(acetamido)benzyl | 4-OMe-phenyl | H | H | OMe | H | HCl (2/1) H₂O (2.5/1) | 255 (B) | 512; Rt = 5.04 |
| 115 | N-methyl-4-methylpiperidine | 2-methyl-3-phenyl-2-butenyl | 4-OMe-phenyl | H | H | OMe | H | H₂O (2/1) | 104 (M) | 495; Rt = 5.74 |
| 116 | N-methyl-4-methylpiperidine | 3-phenyl-2-propynyl | 4-OMe-phenyl | H | H | OMe | H | H₂O (0.35/1) | 151 (M) | 479; Rt = 5.68 |

TABLE-continued
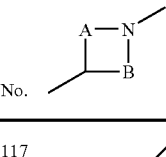
(I)
| No. | A—N B | R3 R2 L R1 | R4 | R5 | R6 | R7 | R8 | Salt and/or Solvates | m.p. (° C.) | LC/MS (M + H)+; Rt (minutes) |
|---|---|---|---|---|---|---|---|---|---|---|
| 117 | 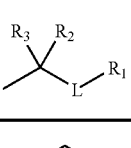 | 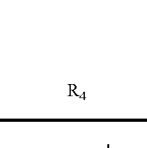 | 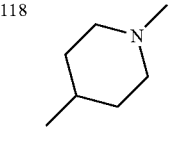 | H | H | OMe | H | HCl (2/1) H2O (2/1) | 210 (B) | 503; Rt = 6.04 |
| 118 | 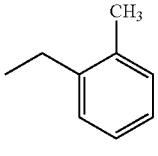 | 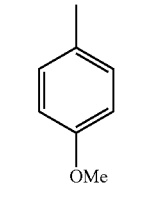 | 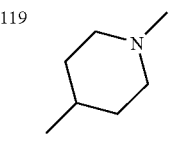 | H | H | OMe | H | HCl (2/1) H2O (1.7/1) | 195 (M) | 469; Rt = 5.44 |
| 119 | 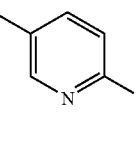 | 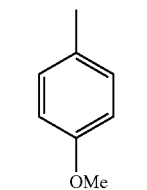 | 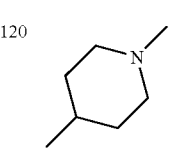 | H | H | OMe | H | HCl (0.6/1) iPr2O (0.1/1) | 228 (M) | 486; Rt = 5.14 |
| 120 | 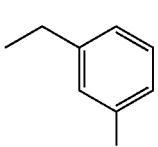 | 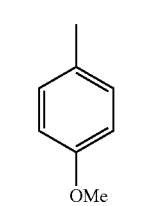 | 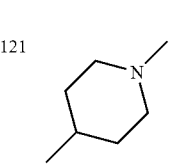 | H | H | OMe | H | HCl (2/1) H2O (1.6/1) | 210 (B) | 469; Rt = 5.44 |
| 121 | 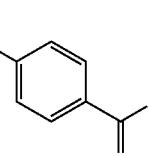 | 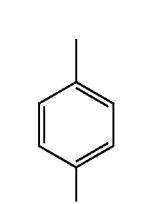 | | H | H | OMe | H | HCl (2/1) H2O (2.4/1) Et2O (0.15/1) | 241 (M) | 497; Rt = 5.21 |

TABLE-continued (I)

| No. | A—N<br>\|   \|<br>B | R₃ R₂<br>\ /<br>C<br>/ \<br>L' R₁ | R₄ | R₅ | R₆ | R₇ | R₈ | Salt and/or Solvates | m.p. (° C.) | LC/MS (M + H)+;<br>Rt (minutes) |
|---|---|---|---|---|---|---|---|---|---|---|
| 122 | 4-methylpiperidinyl | 2,4-dimethyl-5-ethylthiophene | 4-methoxyphenyl | H | H | OMe | H | HCl (2/1) H₂O (1.2/1) | 296 (M) | 489; Rt = 5.56 |
| 123 | 4-methylpiperidinyl | 4-(carboxamido)benzyl | 4-methoxyphenyl | H | H | OMe | H | HCl (2/1) H₂O (4/1) Et₂O (0.3/1) | 293 (M) | 498; Rt = 4.88 |
| 124 | 4-methylpiperidinyl | 5-ethylbenzofuran | 2,5-dimethoxyphenyl | H | H | OMe | H | HCl (2/1) H₂O (2/1) | 250 (M) | 525; Rt = 5.50 |
| 125 | 4-methylpiperidinyl | 5-ethyl-1,3-benzodioxole | 2,5-dimethoxyphenyl | H | H | OMe | H | HCl (2/1) H₂O (2.3/1) iPr₂O (0.2/1) | 272 (M) | 529; Rt = 5.33 |
| 126 | 4-methylpiperidinyl | 6-ethyltetralin | 4-methoxyphenyl | H | H | OMe | H | HCl (2/1) H₂O (2.3/1) | 224 (M) | 509; Rt = 5.91 |
| 127 | 4-methylpiperidinyl | 6-methylcoumarin | 4-methoxyphenyl | H | H | OMe | H | HCl (2/1) H₂O (2.5/1) | 293 (M) | 523; Rt = 5.21 |

TABLE-continued (I)

| No. | A—N—B (ring) | R₃R₂/L/R₁ | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 128 | 4-methylpiperidine | ethyl-quinolin-7-yl | 4-OMe-phenyl | H | H | OMe | H | HCl (3/1) H₂O (4.3/1) Et₂O (0.4/1) | 272 (M) | 506; Rt = 5.17 |
| 129 | 4-methylpiperidine | ethyl-indol-6-yl | 4-OMe-phenyl | H | H | OMe | H | H₂O (0.25/1) | 278 (M) | 494; Rt = 5.49 |
| 130 | 4-methylpiperidine | (4-OMe-benzyl) | 4-OMe-phenyl | H | H | OMe | H | HCl (2/1) H₂O (2.5/1) Et₂O (0.15/1) | 216 (K) | 485; Rt = 5.34 |
| 131 | 4-methylpiperidine | (3-Cl-4-CH₃-benzyl) | 4-OMe-phenyl | H | H | OMe | H | HCl (2/1) H₂O (2/1) | 291 (M) | 503; Rt = 5.71 |
| 132 | 4-methylpiperidine | (4-CH₃-benzyl) | 4-OMe-phenyl | H | H | OMe | H | HCl (1.7/1) H₂O (1/1) | 245 (M) | 483; Rt = 5.64 |

TABLE-continued (I)

| No. | A―N―B structure | R₃R₂/L/R₁ group | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 133 | 4-methylpiperidinyl | 4-(pyrrolidin-1-ylcarbonyl)phenylethyl | 4-MeO-phenyl | H | H | OMe | H | HCl (2/1) H₂O (2.7/1) | 290 (M) | 552; Rt = 5.21 |
| 134 | 4-methylpiperidinyl | 4-chloro-3-methylphenylethyl | 4-MeO-phenyl | H | H | OMe | H | HCl (2/1) H₂O (1.5/1) iPr₂O (0.4/1) | 280 (M) | 503; Rt = 5.71 |
| 135 | 4-methylpiperidinyl | benzothiazol-6-ylethyl | 2,5-dimethoxyphenyl | H | H | OMe | H | H₂O (1/1) | 193 (M) | 542; Rt = 5.21 |
| 136 | 4-methylpiperidinyl | naphthalen-2-ylethyl | 4-ethoxyphenyl | H | H | OMe | H | HCl (2/1) H₂O (1.3/1) | 239 (M) | 505; Rt = 6.06 |
| 137 | 4-methylpiperidinyl | naphthalen-2-ylethyl | phenyl | H | H | phenyl | H | HCl (2/1) H₂O (1.8/1) Et₂O (0.25/1) | 224 (M) | 521; Rt = 6.48 |
| 138 | 4-methylpiperidinyl | benzimidazol-5-ylethyl | 4-MeO-phenyl | H | H | OMe | H | — | 267 (M) | 495; Rt = 4.62 |

TABLE-continued
(I)
| No. | A-N/B | R₃R₂/L/R₁ | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 139 | 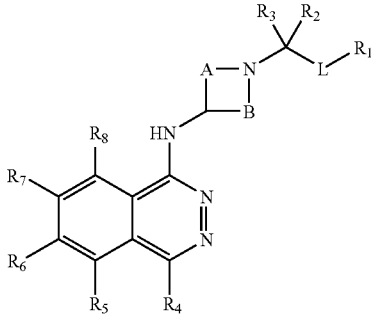 | 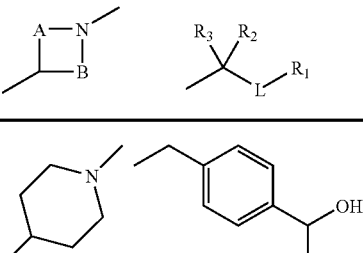 | 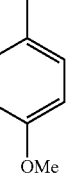 | H | H | OMe | H | HCl (2/1) H₂O (1.8/1) Et₂O (0.2/1) | 208 (K) | 499; Rt = 5.07 |
| 140 | 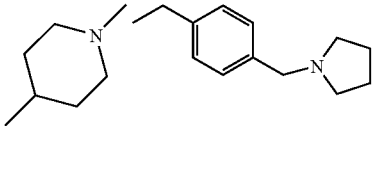 | 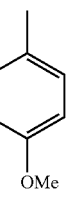 | 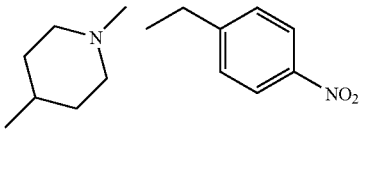 | H | H | OMe | H | HCl (3/1) H₂O (4.5/1) | 222 (K) | 538; Rt = 4.49 |
| 141 | 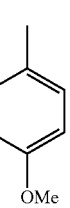 | 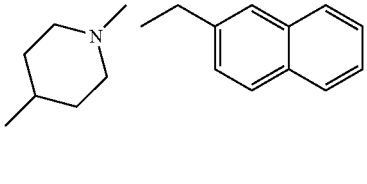 | 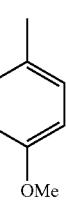 | H | H | OMe | H | H₂O (0.3/1) | 212 (M) | 500; Rt = 5.32 |
| 142 | 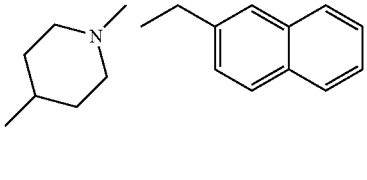 | 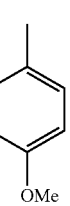 | (4-OMe-phenyl) | H | Me | H | H | H₂O (0.2/1) | 134 (M) | 489; Rt = 5.72 |
| 143 | | | (4-OMe-phenyl) | H | H | Cl | H | HCl (2/1) H₂O (1.15/1) | 230 (K) | 509; Rt = 6.13 |

TABLE-continued (I)

| No. | [A-N-B ring] | [R3,R2,R1,L group] | R4 | R5 | R6 | R7 | R8 | Salt and/or Solvates | m.p. (°C.) | LC/MS (M + H)+; Rt (minutes) |
|---|---|---|---|---|---|---|---|---|---|---|
| 144 | 4-methylpiperidine | 4-bromo-3-methylbenzyl | 4-methoxyphenyl | H | H | OMe | H | HCl (2/1) H$_2$O (1.3/1) | 289 (M) | 549; Rt = 5.76 |
| 145 | 4-methylpiperidine | 2-naphthylmethyl | 4-bromophenyl | H | H | OMe | H | HCl (2/1) H$_2$O (0.6/1) Et$_2$O (0.14/1) | 246 (M) | 555; Rt = 6.13 |
| 146 | 4-methylpiperidine | benzo[1,3]dioxol-5-ylmethyl | —CH$_2$—O—CH$_3$ | H | H | OMe | H | HCl (2/1) H$_2$O (1/1) | 284 (M) | 437; Rt = 4.48 |
| 147 | 4-methylpiperidine | 2-naphthylmethyl | benzyloxymethyl | H | H | OMe | H | HCl (2/1) Et$_2$O (0.23/1) | 284 (M) | 519; Rt = 5.87 |
| 148 | 4-methylpiperidine | 2-naphthylmethyl | —CH$_2$—OH | H | H | OMe | H | HCl (2/1) H$_2$O (2.8/1) | 186 (K) | 429; Rt = 4.76 |
| 149 (−) | 4-methylpiperidine | 2-naphthylmethyl | 4-methoxyphenyl | H | H | OMe | H | Isohexane (0.5/1) H$_2$O (1.7/1) | 136 (M) | 519; Rt = 5.76 |

TABLE-continued (I)

| No. | A—N⟨B | R₃,R₂,R₁,L | R₄ | R₅ | R₆ | R₇ | R₈ | Salt and/or Solvates | m.p. (° C.) | LC/MS (M + H)+; Rt (minutes) |
|---|---|---|---|---|---|---|---|---|---|---|
| 150 (+) | 4-methylpiperidinyl | 2-naphthylmethyl | 4-methoxybenzyl | H | H | OMe | H | Isohexane (0.4/1) H₂O (2.2/1) | 132 (M) | 519; Rt = 5.76 |
| 151 | 4-methylpiperidinyl | 4-(N,N-dimethylaminomethyl)benzyl | 4-methoxybenzyl | H | H | OMe | H | HCl (3/1) H₂O (4.5/1) Et₂O (0.3/1) | 218 (K) | 512; Rt = 4.40 |

The compounds according to the invention underwent pharmacological tests. Their affinity towards the receptor 1 of Melamin-Concentrating Hormone (MCH), $MCH_1$ was determined by these means.

The tests consisted in measuring the in vitro activity of the compounds of the invention on the $MCH_1$ receptors of MCH.

Binding Studies

The measurement of the affinity of the compounds of the invention for the MCH receptors was performed by studying the displacement of the binding of a radiolabelled derivative of MCH to the $MCH_1$ receptors. This study was performed on rat and/or mouse brain membrane preparations according to the protocol described below.

In anticipation of the binding studies, the brains are diluted in HEPES buffer 25 mM (pH: 7.4) containing $MgCl_2$ 5 mM, $CaCl_2$ 1 mM, homogenized using a Polytron blender for 3 times 20 seconds (speed 25), and are then ultracentrifuged at 22 000 rpm and at +4° C. for 30 minutes. The centrifugation pellet is taken up in the same buffer and the membranes are divided into aliquots and stored frozen at −80° C. until the time of use.

The membranes are warmed to room temperature and then incubated in the presence of the test compounds, and of 50 pM of an MCH-based radiolabelled molecule, $[^{125}I]$-Tyr-S36057 (8-amino-3,6-dioxyoctanoyl MCH 6-17 sold by Perkin-Elmer), in HEPES buffer 25 mM (pH: 7.4) containing $MgCl_2$ 5 mM, $CaCl_2$ 1 mM, bacitracin 140 mg/L, phenanthroline 1 mM and 0.2% bovine serum albumin. The incubation is performed at room temperature for 30 minutes, and then stopped by rapid addition of ice-cold HEPES buffer 25 mM (pH: 7.4) supplemented with 0.2% bovine serum albumin, and by filtration through GF/B glass fibre filters preincubated for 2 hours in an aqueous 0.1% polyethyleneimine solution. The radioactivity retained on the filters is measured using a Gamma scintillation counter. The non-specific binding is determined in the presence of 1 μM of non-radiolabelled S36057. The specific binding is obtained by difference between the total binding and the non-specific binding. The inhibitory activity of the compounds of the invention is expressed by means of the concentration that inhibits 50% of the specific binding ($IC_{50}$).

Within the scope of the invention, the $IC_{50}$ values of the compounds are generally less than 10 μM.

The compounds of formula (I) advantageously have $IC_{50}$ values of less than 1 μM, more advantageously less than or equal to 100 nM and even more advantageously less than or equal to 10 nM.

By way of example:

the compound according to Example 42 has an $IC_{50}$ of 360 nM;

the compound according to Example 2 has an $IC_{50}$ of 72 nM;

the compound according to Example 4 has an $IC_{50}$ of 3 nM.

The compounds according to the invention may be used for the preparation of medicinal products, in particular medicinal products that are antagonists of the $MCH_1$ receptor of MCH.

What is claimed is:

1. A compound corresponding to general formula (I)

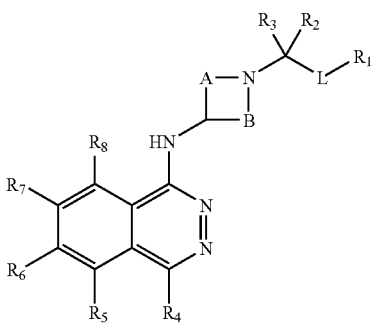

wherein:
- A represents a $C_{1-4}$-alkylene group optionally substituted with one or more groups $R_9$, which may be identical or different;
- B represents a $C_{1-4}$-alkylene group optionally substituted with one or more groups $R_{10}$, which may be identical or different;
- $R_9$ and $R_{10}$ each represent, independently of each other, a hydrogen atom or a $C_{1-5}$-alkyl group, or, alternatively, $R_9$ and $R_{10}$ together form a single bond or a $C_{1-4}$-alkylene group;
- L represents a single bond or a $C_{1-2}$-alkylene, —CH=CH— or —C≡C— group; the $C_{1-2}$-alkylene and —CH=CH— groups being optionally substituted with one or more $C_{1-2}$-alkyl substituents; or, alternatively, L represents a cycloprop-1,2-diyl group;
- $R_1$ represents an aryl or heteroaryl group; the aryl and heteroaryl groups being optionally substituted with one or more radicals Z, which may be identical or different;
- $R_2$ and $R_3$ represent, independently of each other, a hydrogen atom or a $C_{1-3}$-alkyl or $C_{1-3}$-fluoroalkyl group, or, alternatively, $R_2$ and $R_3$ form, together with the carbon atom that bears them, a cycloprop-1,1-diyl group;
- $R_4$ represents a hydrogen atom or a $C_{1-5}$-alkyl, $C_{1-3}$-fluoroalkyl, $C_{3-6}$-cycloalkyl, $C_{3-6}$-cycloalkyl-$C_{1-3}$-alkylene, $C_{1-3}$-alkyl-O—$C_{1-3}$-alkylene, HO—$C_{1-3}$-alkylene or $C_{1-3}$-alkyl-X—$C_{1-3}$-alkylene group in which X represents S, SO or $SO_2$,
  - or, alternatively, $R_4$ represents an $R_aR_bN$—$C_{1-3}$-alkylene, aryl, aryl-$C_{1-3}$-alkylene, aryl-O—, aryl-O—$C_{1-3}$-alkylene, aryl-$C_{1-3}$-alkylene-O—$C_{1-3}$-alkylene, heteroaryl or heteroaryl-$C_{1-3}$-alkylene group; the aryl, aryl-$C_{1-3}$-alkylene, aryl-O—, aryl-O—$C_{1-3}$-alkylene, heteroaryl and heteroaryl-$C_{1-3}$-alkylene groups being optionally substituted with one or more radicals Z, which may be identical or different;
- $R_5$ represents a hydrogen or halogen atom or a $C_{1-5}$-alkyl, $C_{1-3}$-fluoroalkyl, $C_{1-5}$-alkoxy, $C_{1-3}$-fluoroalkoxy, HO—$C_{1-3}$-alkylene, —CN or $C_{1-3}$-alkyl-X— group in which X represents S, SO or $SO_2$,
  - or, alternatively, $R_5$ represents an $R_aR_bN$—, $R_aR_bN$—$C_{1-3}$-alkylene, aryl, aryl-$C_{1-3}$-alkylene, aryl-O— or heteroaryl group; the aryl, aryl-$C_{1-3}$-alkylene, aryl-O— and heteroaryl groups being optionally substituted with one or more radicals Z, which may be identical or different;
- $R_6$ represents a hydrogen or halogen atom or a $C_{1-5}$-alkyl, $C_{1-3}$-fluoroalkyl, $C_{1-5}$-alkoxy, $C_{1-3}$-fluoroalkoxy, —CN, $R_aR_bN$—, $R_aR_bN$—$C_{1-3}$-alkylene, aryl or heteroaryl group; the aryl and heteroaryl groups being optionally substituted with one or more radicals Z, which may be identical or different;
- $R_7$ represents a hydrogen or halogen atom or a $C_{1-5}$-alkyl, $C_{1-3}$-fluoroalkyl, $C_{1-5}$-alkoxy, $C_{1-3}$-fluoroalkoxy, HO—$C_{1-3}$-alkylene, —CN or $C_{1-3}$-alkyl-X— group in which X represents S, SO or $SO_2$; or, alternatively, $R_7$ represents an $R_aR_bN$—, $R_aR_bN$—$C_{1-3}$-alkylene, $R_aR_bNC(O)$—, $C_{1-3}$-alkyl-C(O)—, aryl, aryl-O— or heteroaryl group; the aryl, aryl-O— and heteroaryl groups being optionally substituted with one or more radicals Z, which may be identical or different;
- $R_8$ represents a hydrogen or halogen atom or a $C_{1-5}$-alkyl, $C_{1-5}$-alkoxy or $C_{1-3}$-fluoroalkoxy group;
- Z represents a hydrogen or halogen atom or a $C_{1-5}$-alkyl, $C_{1-3}$-fluoroalkyl, $C_{3-6}$-cycloalkyl, $C_{3-6}$-cycloalkyl-$C_{1-3}$-alkylene, phenyl, $C_{1-5}$-alkoxy, $C_{1-3}$-fluoroalkoxy, $C_{1-3}$-alkyl-O—$C_{1-3}$-alkylene, HO—$C_{1-3}$-alkylene, $NO_2$, —CN, $C_{1-3}$-alkyl-X— or $C_{1-3}$-alkyl-X—$C_{1-3}$-alkylene group in which X represents S, SO or $SO_2$,
  - or, alternatively, Z represents an $R_aR_bN$—, $R_aR_bN$—$C_{1-3}$-alkylene, $R_aR_bNC(O)$—, $C_{1-3}$-alkyl-C(O)—, $C_{1-4}$-alkyl-$CO_2$— or $C_{3-6}$-cycloalkyl-C(O)— group,
  - or, alternatively, Z represents an oxo radical,
  - or, alternatively, two adjacent radicals Z together form a $C_{1-3}$-alkylenedioxy group; and
- $R_a$ and $R_b$ each represent, independently of each other, a hydrogen atom or a $C_{1-3}$-alkyl or $C_{1-3}$-alkyl-C(O)— group; or, alternatively, $R_a$ and $R_b$ form, together with the nitrogen atom that bears them, a heterocycle optionally substituted with one or more $C_{1-3}$-alkyl or oxo groups;

it being understood that when $R_2$, $R_3$, $R_5$, $R_6$, $R_7$ and $R_8$ all represent a hydrogen atom, A and B both represent an ethylenyl group (—$CH_2CH_2$—) and L is a single bond, and $R_1$ and $R_4$ cannot both represent an unsubstituted phenyl group; or an acid-addition salt thereof, or an enantiomer a diastereoisomer thereof, or a mixture thereof.

2. The compound of claim 1, wherein:
- A represents a $C_{1-4}$-alkylene group optionally substituted with one or more groups $R_9$, which may be identical or different;
- B represents a $C_{1-4}$-alkylene group optionally substituted with one or more groups $R_{10}$, which may be identical or different;
- $R_9$ and $R_{10}$ each represent a hydrogen atom, or, alternatively, $R_9$ and $R_{10}$ together form a $C_{1-4}$-alkylene group;
- L represents a single bond or —CH=CH—;
- $R_1$ represents an aryl or a heteroaryl group; the aryl and heteroaryl groups being optionally substituted with one or more radicals Z, which may be identical or different;
- $R_2$ and $R_3$ represent, independently of each other, a hydrogen atom or a $C_{1-3}$-alkyl group;
- $R_4$ represents a hydrogen atom or a $C_{1-5}$-alkyl, $C_{3-6}$-cycloalkyl, $C_{3-6}$-cycloalkyl-$C_{1-3}$-alkylene, $C_{1-3}$-alkyl-O—$C_{1-3}$-alkylene, aryl, aryl-$C_{1-3}$-alkylene, aryl-$C_{1-3}$-alkylene-O—$C_{1-3}$-alkylene, heteroaryl or heteroaryl-$C_{1-3}$-alkylene group; the aryl, aryl-$C_{1-3}$-alkylene, heteroaryl and heteroaryl-$C_{1-3}$-alkylene groups being optionally substituted with one or more radicals Z, which may be identical or different;
- $R_5$ represents a hydrogen atom or a $C_{1-5}$-alkyl, $C_{1-5}$-alkoxy or aryl group; the aryl group being optionally substituted with one or more radicals Z, which may be identical or different;
- $R_6$ represents a hydrogen atom;

$R_7$ represents a halogen atom or a $C_{1-5}$-alkyl or $C_{1-5}$-alkoxy group or an aryl;

$R_8$ represents a hydrogen atom;

Z represents a hydrogen or halogen atom or a $C_{1-5}$-alkyl, $C_{1-3}$-fluoroalkyl, $C_{3-6}$-cycloalkyl, $C_{3-6}$-cycloalkyl-$C_{1-3}$-alkylene, phenyl, $C_{1-5}$-alkoxy, $C_{1-3}$-fluoroalkoxy, $C_{1-3}$-alkyl-O—$C_{1-3}$-alkylene, HO—$C_{1-3}$-alkylene, $NO_2$, —CN, $C_{1-3}$-alkyl-X— or $C_{1-3}$-alkyl-X—$C_{1-3}$-alkylene group in which X represents S, SO or $SO_2$, or, alternatively, Z represents an $R_aR_bN$—, $R_aR_bN$—$C_{1-3}$-alkylene, $R_aR_bNC(O)$—, $C_{1-3}$-alkyl-C(O)— or $C_{3-6}$-cycloalkyl-C(O)— group, or, alternatively, Z represents an oxo radical, or, alternatively, two adjacent radicals Z together form a $C_{1-3}$-alkylenedioxy group;

$R_a$ and $R_b$ each represent, independently of each other, a hydrogen atom or a $C_{1-3}$-alkyl or $C_{1-3}$-alkyl-C(O)— group, or, alternatively, $R_a$ and $R_b$ form, together with the nitrogen atom that bears them, a heterocycle optionally substituted with one or more $C_{1-3}$-alkyl or oxo groups;

or an acid-addition salt thereof, or an enantiomer or a diastereoisomer thereof, or a mixture thereof.

3. The A compound of claim 1, wherein:

A represents a $C_{1-4}$-alkylene group optionally substituted with a group $R_9$;

B represents a $C_{1-4}$-alkylene group optionally substituted with a group $R_{10}$;

$R_9$ and $R_{10}$ each represent a hydrogen atom or $R_9$ and $R_{10}$ together form a $C_{1-4}$-alkylene group;

L represents a single bond or —CH═CH—;

$R_1$ represents an aryl optionally substituted with one or more radicals Z, which may be identical or different;

$R_2$ and $R_3$ represent, independently of each other, a hydrogen atom or a $C_{1-3}$-alkyl group;

$R_4$ represents a hydrogen atom or a $C_{1-5}$-alkyl, $C_{3-6}$-cycloalkyl, $C_{3-6}$-cycloalkyl-$C_{1-3}$-alkylene, $C_{1-3}$-alkyl-O—$C_{1-3}$-alkylene, aryl or heteroaryl group; the aryl and heteroaryl groups being optionally substituted with one or more radicals Z, which may be identical or different;

$R_5$ represents a hydrogen atom;

$R_6$ represents a hydrogen atom;

$R_7$ represents a halogen atom, a methyl or a methoxy;

$R_8$ represents a hydrogen atom;

Z represents a hydrogen atom, a halogen atom or a $C_{1-5}$-alkyl, $C_{1-5}$-alkoxy, $C_{1-3}$-alkyl-O—$C_{1-3}$-alkylene, phenyl, HO—$C_{1-3}$-alkylene, —CN or $C_{1-3}$-alkyl-X— group in which X represents a sulfur atom, or, alternatively, Z represents an $R_aR_bN$—, $R_aR_bN$—$C_{1-3}$-alkylene, $R_aR_bNC(O)$— or $C_{1-3}$-alkyl-C(O)— group, or, alternatively, Z represents an oxo radical, or, alternatively, two adjacent radicals Z together form a $C_{1-3}$-alkylenedioxy group; and $R_a$ and $R_b$ each represent, independently of each other, a hydrogen atom or a $C_{1-3}$-alkyl or $C_{1-3}$-alkyl-C(O)— group;

or an acid-addition salt thereof or an enantiomer or a diastereoisomer thereof, or a mixture thereof.

4. The compound of claim 1, selected from the group consisting of:

7-methoxy-4-(4-methoxyphenyl)-N-[8-(2-naphthylmethyl)-8-azabicyclo[3.2.1]oct-3-yl]phthalazin-1-amine;

7-methoxy-4-(4-methoxyphenyl)-N-[1-(2-naphthylmethyl)piperidin-4-yl]phthalazin-1-amine;

7-methoxy-4-(3-methoxyphenyl)-N-[1-(2-naphthylmethyl)piperidin-4-yl]phthalazin-1-amine;

7-methoxy-4-(2-methoxyphenyl)-N-[1-(2-naphthylmethyl)piperidin-4-yl]phthalazin-1-amine;

7-methoxy-N-[1-(2-naphthylmethyl)piperidin-4-yl]-4-phenylphthalazin-1-amine;

4-(4-methoxyphenyl)-7-methyl-N-[1-(2-naphthylmethyl)piperidin-4-yl]phthalazin-1-amine;

4-(3,4-dimethoxyphenyl)-7-methoxy-N-[1-(2-naphthylmethyl)piperidin-4-yl]phthalazin-1-amine;

N-[1-(1,3-benzodioxol-5-ylmethyl)piperidin-4-yl]-7-methoxy-4-(4-methoxyphenyl)phthalazin-1-amine dihydrochloride;

4-ethyl-7-methoxy-N-[1-(2-naphthylmethyl)piperidin-4-yl]phthalazin-1-amine;

4-benzyl-7-methoxy-N-[1-(2-naphthylmethyl)piperidin-4-yl]phthalazin-1-amine;

7-methoxy-4-(methoxymethyl)-N-[1-(2-naphthylmethyl)piperidin-4-yl]phthalazin-1-amine hydrochloride;

N-[1-(1-benzofuran-5-ylmethyl)piperidin-4-yl]-7-methoxy-4-(4-methoxyphenyl)phthalazin-1-amine;

N-[1-(3,4-dimethylbenzyl)piperidin-4-yl]-7-methoxy-4-(4-methoxyphenyl)phthalazin-1-amine;

7-methoxy-4-(4-methoxyphenyl)-N-{1-[(1-methyl-1H-indol-2-yl)methyl]piperidin-4-yl}phthalazin-1-amine;

4-cyclopropyl-7-methoxy-N-[1-(2-naphthylmethyl)piperidin-4-yl]phthalazin-1-amine;

N-[1-(3-fluoro-4-methoxybenzyl)piperidin-4-yl]-7-methoxy-4-(4-methoxyphenyl)phthalazin-1-amine;

N-[1-(2,3-dihydro-1,4-benzodioxin-6-ylmethyl)piperidin-4-yl]-7-methoxy-4-(4-methoxyphenyl)phthalazin-1-amine;

4-(1,3-benzodioxol-5-yl)-7-methoxy-N-[1-(2-naphthylmethyl)piperidin-4-yl]phthalazin-1-amine dihydrochloride;

4-(4-chlorophenyl)-7-methoxy-N-[1-(2-naphthylmethyl)piperidin-4-yl]phthalazin-1-amine;

7-methoxy-N-[1-(2-naphthylmethyl)piperidin-4-yl]-4-[4-(trifluoromethyl)phenyl]phthalazin-1-amine;

N-[1-(1-benzothien-2-ylmethyl)piperidin-4-yl]-7-methoxy-4-(4-methoxyphenyl)phthalazin-1-amine;

4-cyclopentyl-7-methoxy-N-[1-(2-naphthylmethyl)piperidin-4-yl]phthalazin-1-amine dihydrochloride;

N-[1-(2,3-dihydro-1-benzofuran-5-ylmethyl)piperidin-4-yl]-7-methoxy-4-(4-methoxyphenyl)phthalazin-1-amine;

N-[1-(2,3-dihydro-1H-inden-5-ylmethyl)piperidin-4-yl]-7-methoxy-4-(4-methoxyphenyl)phthalazin-1-amine;

7-methoxy-4-(4-methoxyphenyl)-N-{1-[1-(2-naphthyl)ethyl]piperidin-4-yl}phthaiazin-1-amine dihydrochloride;

N-[1-(1,3-benzothiazol-6-ylmethyl)piperidin-4-yl]-7-methoxy-4-(4-methoxyphenyl)phthaiazin-1-amine;

N-[1-(1-benzothien-5-ylmethyl)piperidin-4-yl]-7-methoxy-4-(4-methoxyphenyl)phthalazin-1-amine;

N-[1-(1H-indol-3-ylmethyl)piperidin-4-yl]-7-methoxy-4-(4-methoxyphenyl)phthalazin-1-amine;

7-methoxy-4-(4-methylphenyl)-N-[1-(2-naphthylmethyl)piperidin-4-yl]phthalazin-1-amine;

4-butyl-7-methoxy-N-[1-(2-naphthylmethyl)piperidin-4-yl]phthaiazin-1-amine;

7-methoxy-4-(4-methoxyphenyl)-N-{1-[(2E)-3-phenylprop-2-en-1-yl]piperidin-4-yl}phthalazin-1-amine dihydrochloride;

7-methoxy-N-[1-(2-naphthylmethyl)piperidin-4-yl]phthaiazin-1-amine;

4-(cyclopropylmethyl)-7-methoxy-N-[1-(2-naphthylmethyl)piperidin-4-yl]phthalazin-1-amine;

N-[1-(3-fluoro-4-methylbenzyl)piperidin-4-yl]-7-methoxy-4-(4-methoxyphenyl)phthaiazin-1-amine;
7-methoxy-4-(4-methoxyphenyl)-N-[1-(4-methylbenzyl)piperidin-4-yl]phthaiazin-1-amine;
4-(4-fluorophenyl)-7-methoxy-N-[1-(2-naphthylmethyl)piperidin-4-yl]phthalazin-1-amine;
N-[1-(1H-indol-5-ylmethyl)piperidin-4-yl]-7-methoxy-4-(4-methoxyphenyl)phthaiazin-1-amine;
7-methoxy-4-[4-(methoxymethyl)phenyl]-N-[1-(2-naphthylmethyl)piperidin-4-yl]phthalazin-1-amine;
7-methoxy-N-[1-(4-methoxy-3-methylbenzyl)piperidin-4-yl]-4-(4-methoxyphenyl)phthalazin-1-amine;
7-methoxy-4-methyl-N-[1-(2-naphthylmethyl)piperidin-4-yl]phthalazin-1-amine;
4-(2,5-dimethoxyphenyl)-7-methoxy-N-[1-(2-naphthylmethyl)piperidin-4-yl]phthalazin-1-amine dihydrochloride;
7-methoxy-4-(4-methoxyphenyl)-N-[1-(quinolin-6-ylmethyl)piperidin-4-yl]phthalazin-1-amine;
7-methoxy-4-(4-methoxyphenyl)-N-{1-[(1-methyl-1H-indol-5-yl)methyl]piperidin-4-yl}phthalazin-1-amine;
4-(2,4-dimethoxyphenyl)-7-methoxy-N-[1-(2-naphthylmethyl)piperidin-4-yl]phthalazin-1-amine dihydrochloride;
4-(3,5-dimethoxyphenyl)-7-methoxy-N-[1-(2-naphthylmethyl)piperidin-4-yl]phthalazin-1-amine dihydrochloride;
7-methoxy-N-[1-(2-naphthylmethyl)piperidin-4-yl]-4-(2-phenylethyl)phthalazin-1-amine dihydrochloride;
4-{4-[(diethylamino)methyl]phenyl}-7-methoxy-N-[1-(2-naphthylmethyl)piperidin-4-yl]phthalazin-1-amine trihydrochloride;
7-fluoro-4-(4-fluorophenyl)-N-[1-(2-naphthylmethyl)piperidin-4-yl]phthalazin-1-amine;
7-methoxy-N-[1-(2-naphthylmethyl)piperidin-4-yl]-4-pyridin-3-ylphthalazin-1-amine trihydrochloride;
N-[1-(4-chlorobenzyl)piperidin-4-yl]-7-methoxy-4-(4-methoxyphenyl)phthalazin-1-amine dihydrochloride;
{4-[(4-{[7-methoxy-4-(4-methoxyphenyl)phthalazin-1-yl]amino}piperidin-1-yl)methyl]phenyl}methanol dihydrochloride;
N-{1-[4-(aminomethyl)benzyl]piperidin-4-yl}-7-methoxy-4-(4-methoxyphenyl)phthalazin-1-amine trihydrochloride;
N-{4-[(4-{[7-methoxy-4-(4-methoxyphenyl)phthalazin-1-yl]amino}piperidin-1-yl)methyl]phenyl}acetamide dihydrochloride;
1-{4-[(4-{[7-methoxy-4-(4-methoxyphenyl)phthalazin-1-yl]amino}piperidin-1-yl)methyl]phenyl}ethanone dihydrochloride;
N-[1-(1-benzofuran-5-ylmethyl)piperidin-4-yl]-4-(2,5-dimethoxyphenyl)-7-methoxyphthalazin-1-amine dihydrochloride;
N-[1-(1,3-benzodioxol-5-ylmethyl)piperidin-4-yl]-4-(2,5-dimethoxyphenyl)-7-methoxyphthalazin-1-amine dihydrochloride;
6-[(4-{[7-methoxy-4-(4-methoxyphenyl)phthalazin-1-yl]amino}piperidin-1-yl)methyl]-2H-chromen-2-one dihydrochloride;
N-[1-(1H-indol-6-ylmethyl)piperidin-4-yl]-7-methoxy-4-(4-methoxyphenyl)phthalazin-1-amine;
7-methoxy-N-[1-(4-methoxybenzyl)piperidin-4-yl]-4-(4-methoxyphenyl)phthalazin-1-amine dihydrochloride;
N-[1-(4-ethylbenzyl)piperidin-4-yl]-7-methoxy-4-(4-methoxyphenyl)phthalazin-1-amine dihydrochloride;
N-[1-(1,3-benzothlazol-6-ylmethyl)piperidin-4-yl]-4-(2,5-dimethoxyphenyl)-7-methoxyphthalazin-1-amine;
7-methoxy-N-[1-(2-naphthylmethyl)piperidin-4-yl]-4-(phenoxymethyl)phthalazin-1-amine dihydrochloride;
N-[-(1H-benzimidazol-5-ylmethyl)piperidin-4-yl]-7-methoxy-4-(4-methoxyphenyl)phthalazin-1-amine;
7-chloro-4-(4-methoxyphenyl)-N-[1-(2-naphthyknethyl)piperidin-4-yl]phthalazin-1-amine dihydrochloride;
4-(4-bromophenyl)-7-methoxy-N-[1-(2-naphthylmethyl)piperidin-4-yl]phthalazin-1-amine dihydrochloride;
N-[1-(1,3-benzodioxol-5-ylmethyl)piperidin-4-yl]-7-methoxy-4-(methoxymethyl)phthalazin-1-amine dihydrochloride;
4-[(benzyloxy)methyl]-7-methoxy-N-[1-(2-naphthylmethyl)piperidin-4-yl]phthalazin-1-amine dihydrochloride;
7-methoxy-5-phenyl-N-[1-(2-naphthylmethyl)piperidin-4-yl]phthalazin-1-amine dihydrochloride;
4-(hydroxymethyl)-7-methoxy-N-[1-(2-naphthylmethyl)piperidin-4-yl]-4-(phenoxymethyl)phthalazin-1-amine;
(−)-7-methoxy-4-(4-methoxyphenyl)-N-{1-[1-(2-naphthyl)ethyl]piperidin-4-yl}phthalazin-1-amine;
(+)-7-methoxy-4-(4-methoxyphenyl)-N-{1-[1-(2-naphthyl)ethyl]piperidin-4-yl}phthalazin-1-amine; and
N-{1-[4-(dimethylaminomethyl)benzyl]piperidin-4-yl}-7-methoxy-4-(4-methoxyphenyl)phthalazin-1-amine trihydrochloride.

5. A process for preparing a compound of formula (I) according to claim 1,
wherein a compound of general formula (III)

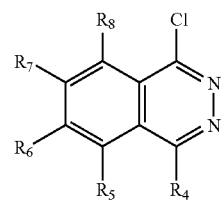

in which $R_4$, $R_5$, $R_6$, $R_7$ and $R_8$ are as defined in the general formula (I) according to claim 1,
is reacted with a compound of general formula (II)

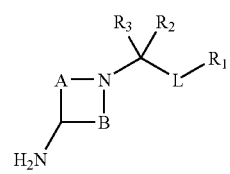

in which $R_1$, $R_2$, $R_3$, L, A and B are as defined in the general formula (I) according to claim 1.

6. A pharmaceutical composition which comprises at least one compound of formula (I) according to claim 1, or a pharmaceutically acceptable salt thereof in combination with at least one pharmaceutically acceptable excipient.

* * * * *